US012655344B2

(12) United States Patent
Bae et al.

(10) Patent No.: US 12,655,344 B2
(45) Date of Patent: Jun. 16, 2026

(54) ORGANIC COMPOUND AND ORGANIC LIGHT EMITTING DIODE AND ORGANIC LIGHT EMITTING DEVICE INCLUDING THE SAME

(71) Applicant: LG DISPLAY CO., LTD., Seoul (KR)

(72) Inventors: Suk Young Bae, Paju-si (KR); Young Ju Ryu, Paju-si (KR); Jun Yun Kim, Paju-si (KR)

(73) Assignee: LG Display Co., Ltd., Seoul (KR)

( * ) Notice: Subject to any disclaimer, the term of this patent is extended or adjusted under 35 U.S.C. 154(b) by 1098 days.

(21) Appl. No.: 17/769,378

(22) PCT Filed: Jul. 26, 2021

(86) PCT No.: PCT/KR2021/009622

§ 371 (c)(1),
(2) Date: Apr. 15, 2022

(87) PCT Pub. No.: WO2022/055123

PCT Pub. Date: Mar. 17, 2022

(65) Prior Publication Data

US 2024/0196743 A1 Jun. 13, 2024

(30) Foreign Application Priority Data

Sep. 11, 2020 (KR) ........................ 10-2020-0116972

(51) Int. Cl.
*H10K 85/60* (2023.01)
*C07D 493/06* (2006.01)
(Continued)

(52) U.S. Cl.
CPC ............ *C09K 11/06* (2013.01); *C07D 493/06* (2013.01); *H10K 85/631* (2023.02);
(Continued)

(58) Field of Classification Search
None
See application file for complete search history.

(56) References Cited

U.S. PATENT DOCUMENTS

| | | | | |
|---|---|---|---|---|
| 2010/0013381 | A1 | 1/2010 | Stoessel et al. | |
| 2010/0237334 | A1* | 9/2010 | Ma | H10K 85/6576 546/281.1 |

(Continued)

FOREIGN PATENT DOCUMENTS

| | | | |
|---|---|---|---|
| KR | 10-2017-0094332 | A | 8/2017 |
| WO | 2018-186462 | A1 | 10/2018 |

OTHER PUBLICATIONS

International Search Report dated Nov. 3, 2021, issued in International Patent Application No. PCT/KR2021/009622.

(Continued)

*Primary Examiner* — Jay Yang
(74) *Attorney, Agent, or Firm* — Morgan, Lewis & Bockius LLP

(57) ABSTRACT

The present disclosure relates to an organic compound of Formula 1, and an organic light emitting diode including the organic compound and an organic light emitting display device including the organic compound. The organic light emitting diode comprises a first electrode, a second electrode facing the first electrode, and a first emitting material layer positioned between the first and second electrodes, where the first emitting material layer includes the organic compound. The organic light emitting display device comprises a substrate, the above organic light emitting diode over the substrate, and an encapsulation film covering the organic light emitting diode.

(Continued)

D1

[Formula 1]

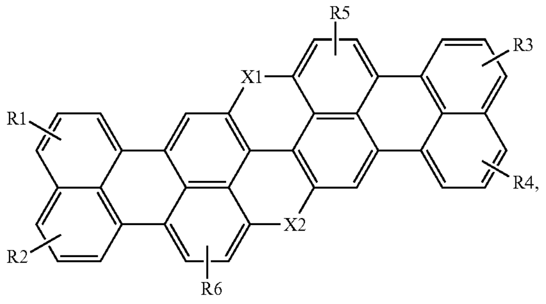

14 Claims, 12 Drawing Sheets

(51) Int. Cl.
*C09K 11/06* (2006.01)
*H10K 50/12* (2023.01)
*H10K 50/13* (2023.01)
*H10K 59/12* (2023.01)
*H10K 101/00* (2023.01)
*H10K 101/20* (2023.01)

(52) U.S. Cl.
CPC .. *H10K 85/6574* (2023.02); *C09K 2211/1018* (2013.01); *H10K 50/12* (2023.02); *H10K 50/13* (2023.02); *H10K 59/12* (2023.02); *H10K 2101/20* (2023.02); *H10K 2101/90* (2023.02)

(56) References Cited

U.S. PATENT DOCUMENTS

2015/0105564 A1* 4/2015 Adachi ................ C07D 209/08
548/440
2018/0013073 A1 1/2018 Duan et al.

OTHER PUBLICATIONS

Mileti T. et al., 2014 “Tailoring Colors by O Annulation of Polycyclic Aromatic Hydrocarbons” Chem. Eur. J., 2017, 23, 2363-2378, DOI: 10.1002/chem.201604866.
Papadakis L. et al. “An Experimental Study of the Structural Effect on the Nanosecond Nonlinear Optical Response of O-Doped Polycyclic Aromatic Hydrocarbons (PAHs)” Journal of Physical Chemistry A 122 (23) , pp. 5142-5152. 10.1021/acs.jpca.8b02737.

* cited by examiner

【Figure 1】
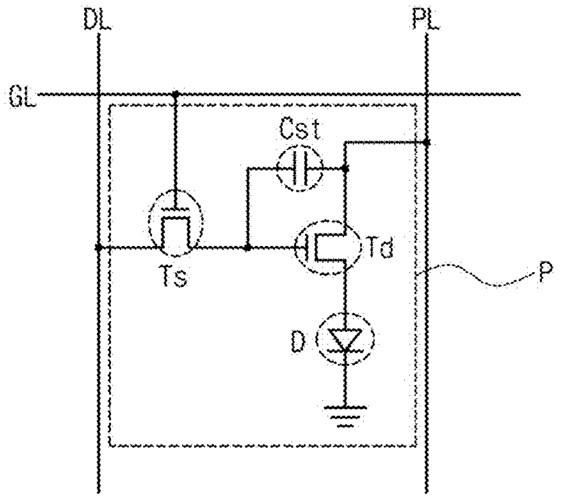

【Figure 2】
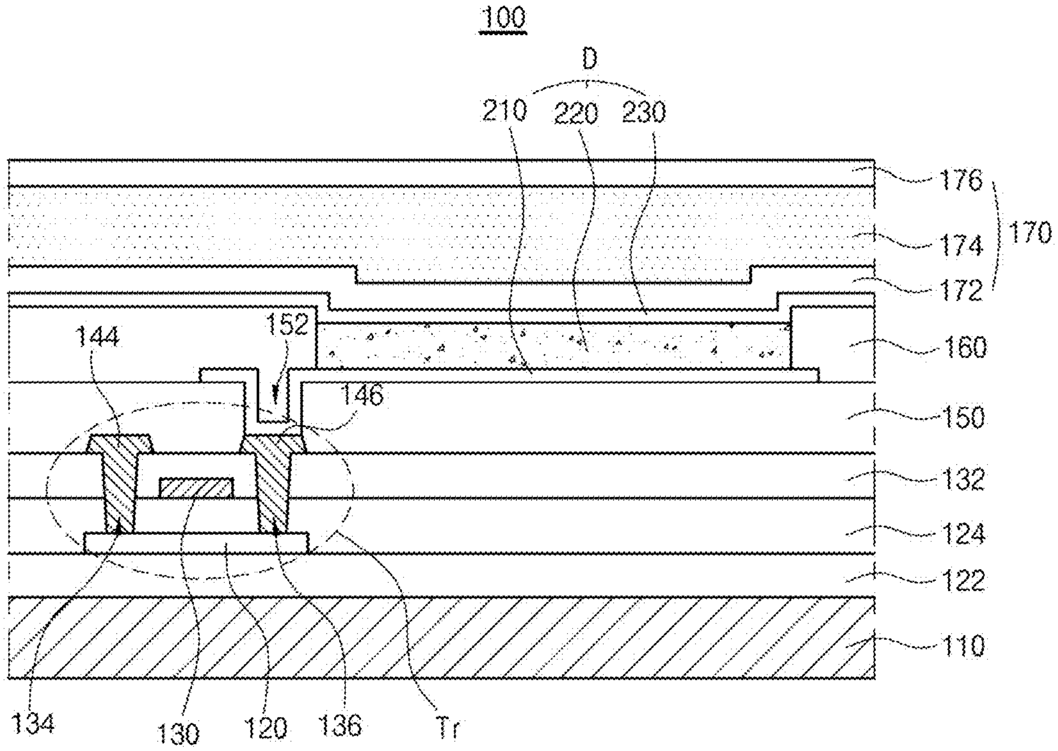

【Figure 3】
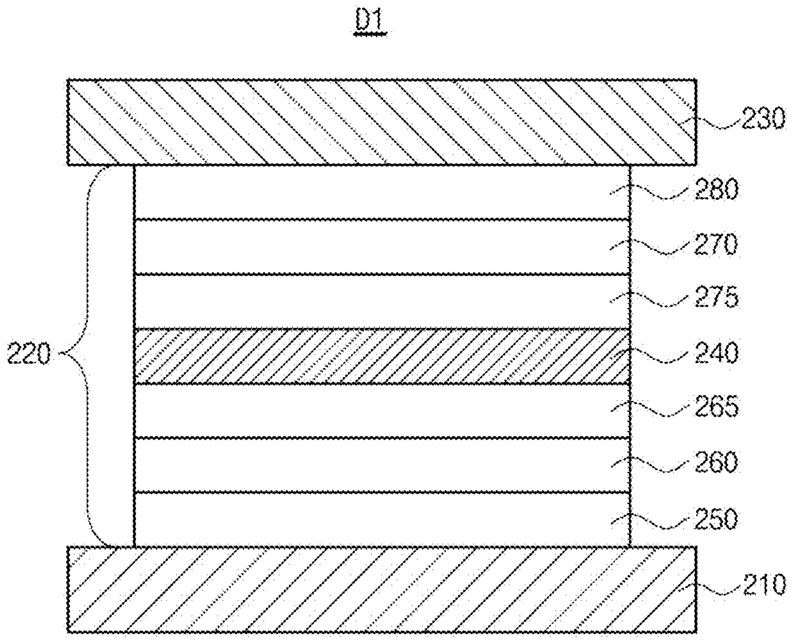

【Figure 4】
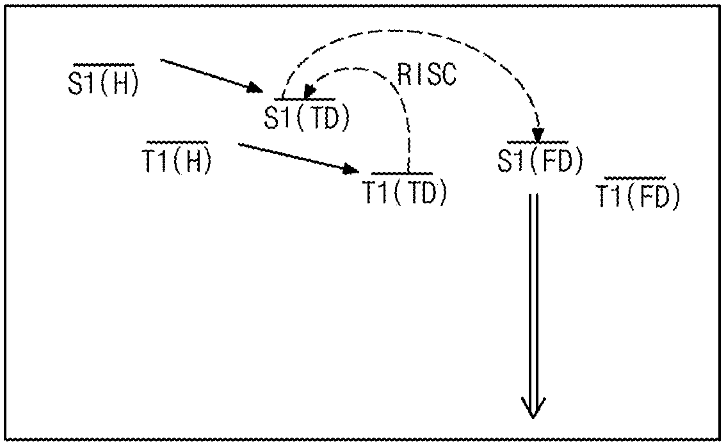

【Figure 5】
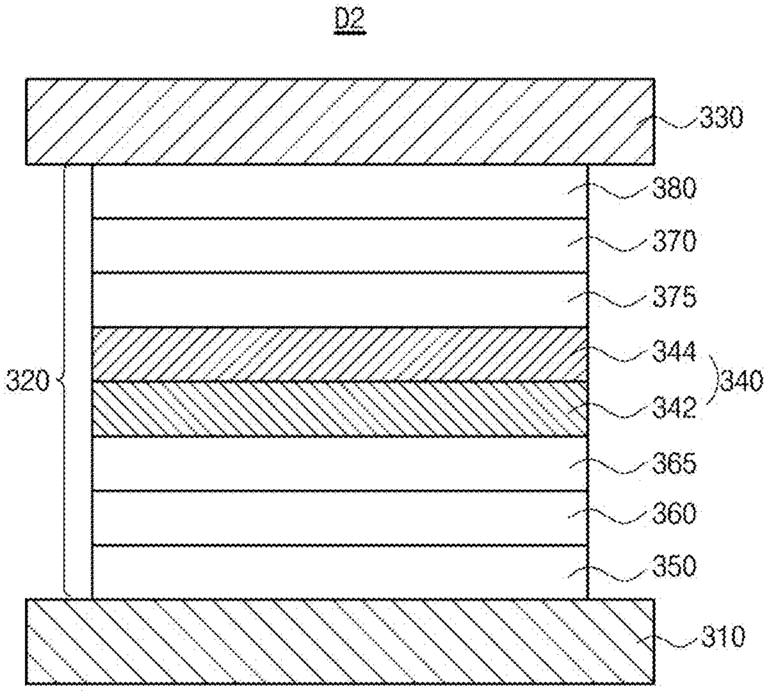

【Figure 6】
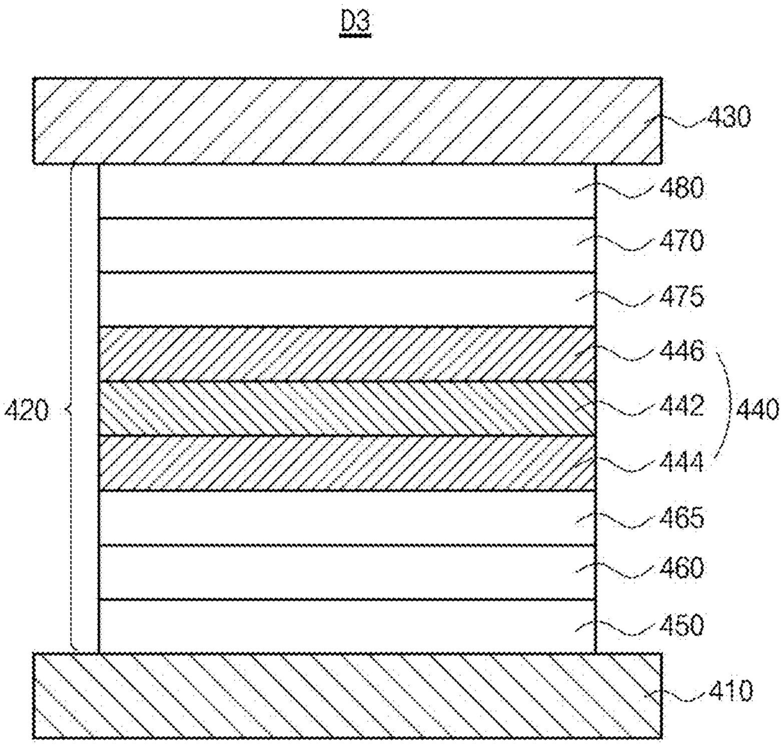

【Figure 7】
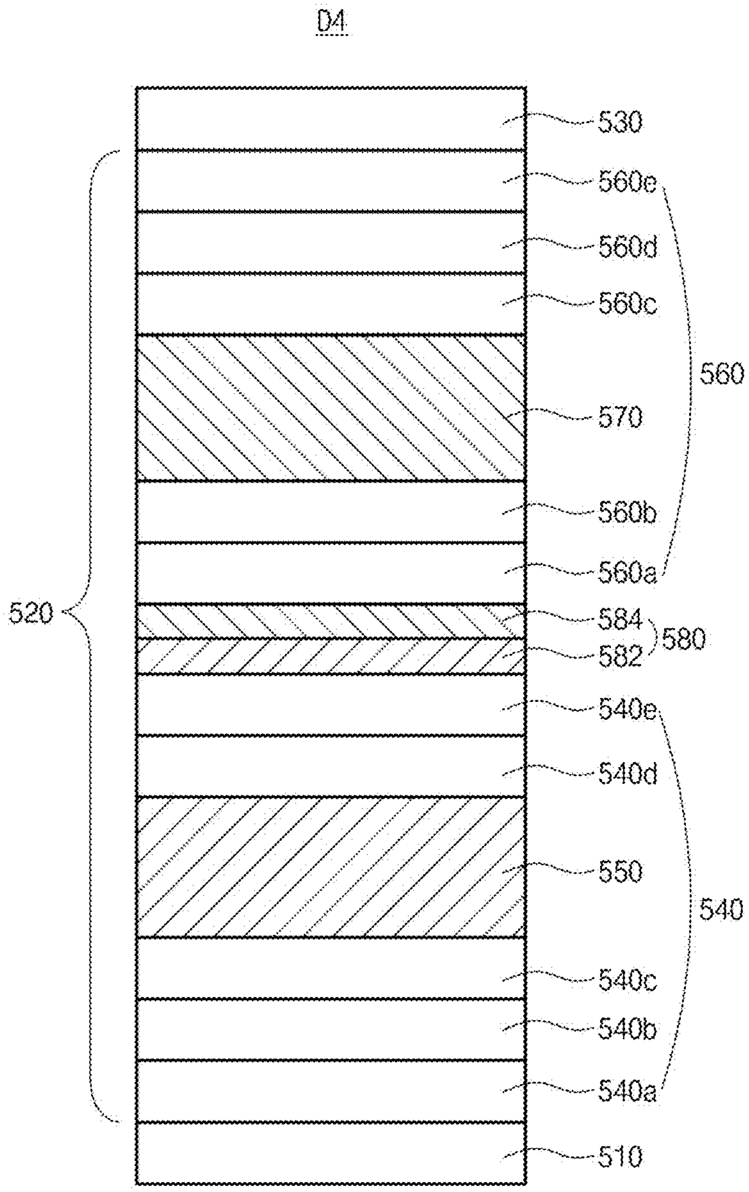

【Figure 8】
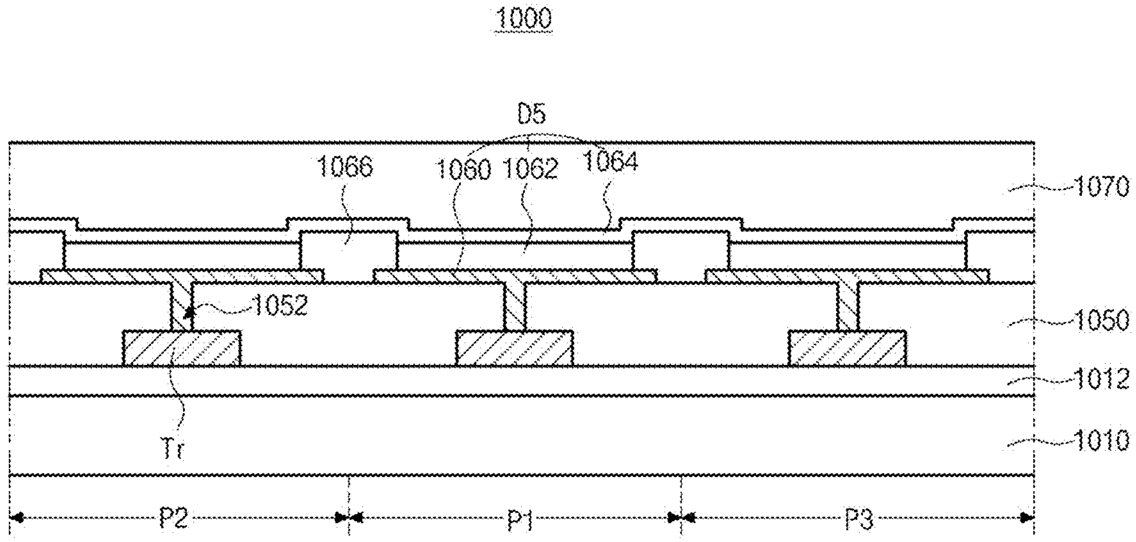

【Figure 9】
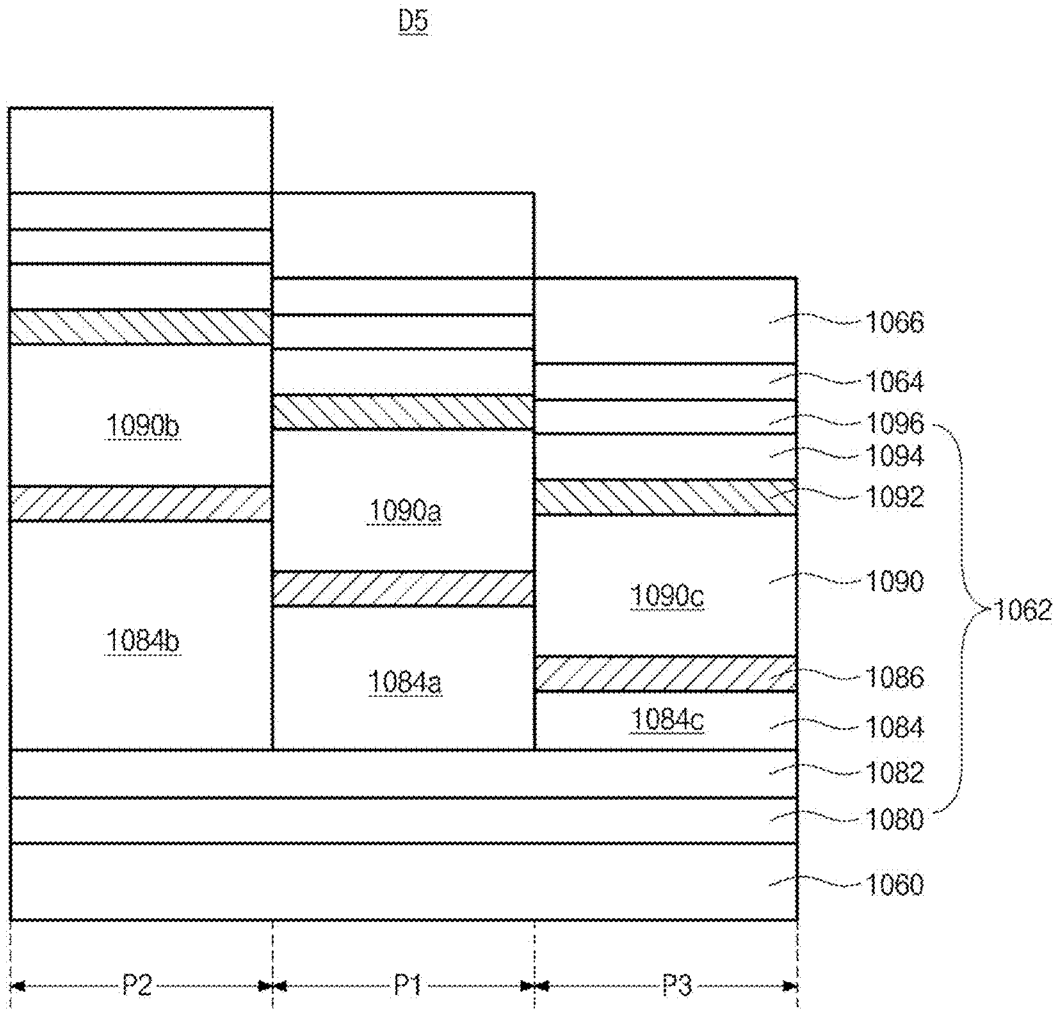

【Figure 10】
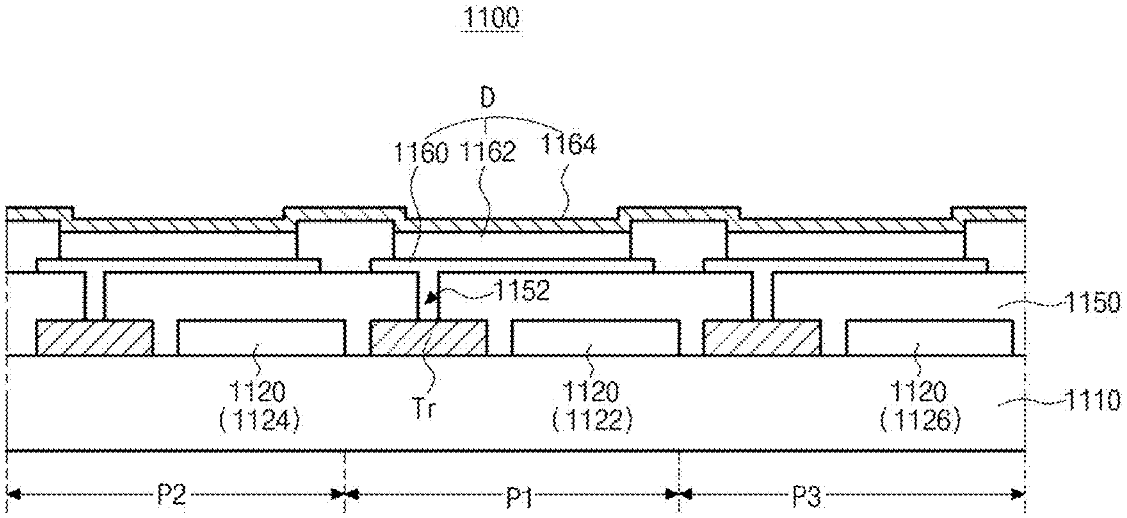

【Figure 11】
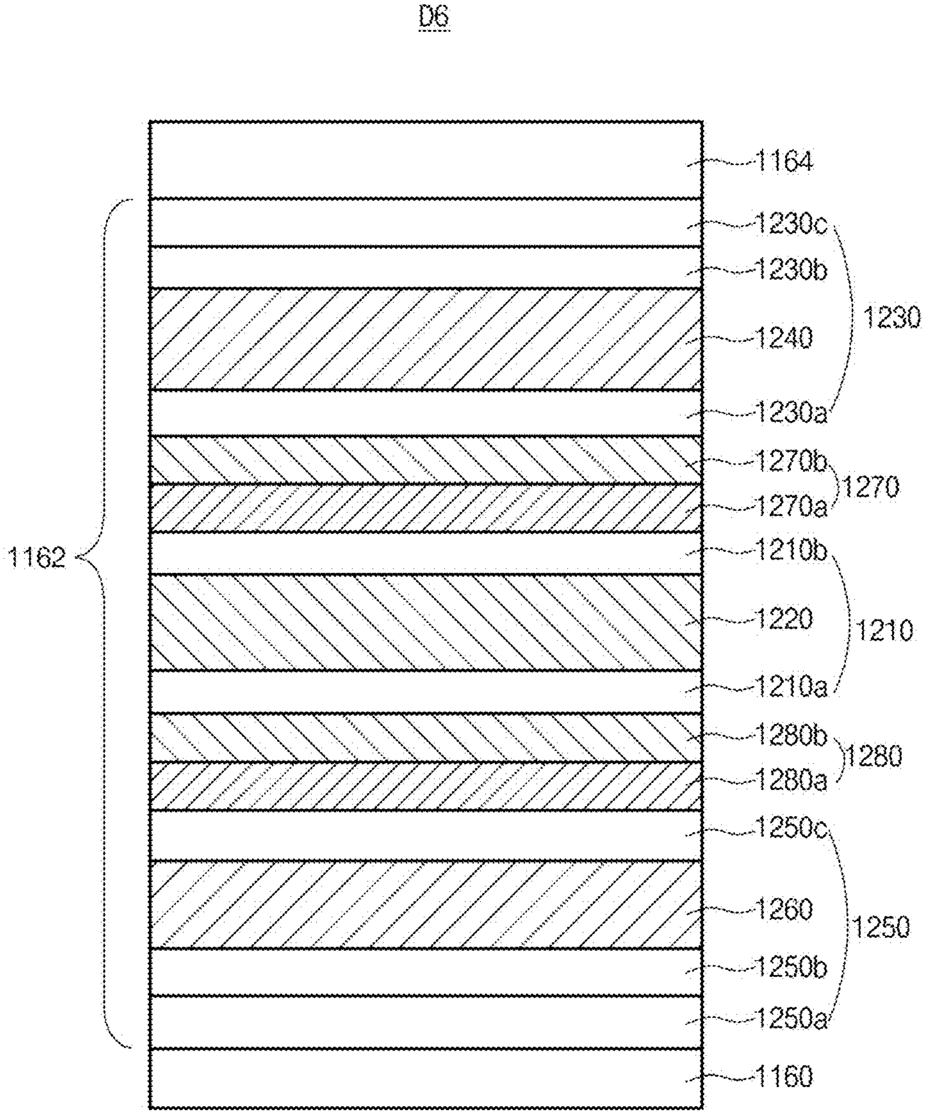

【Figure 12】
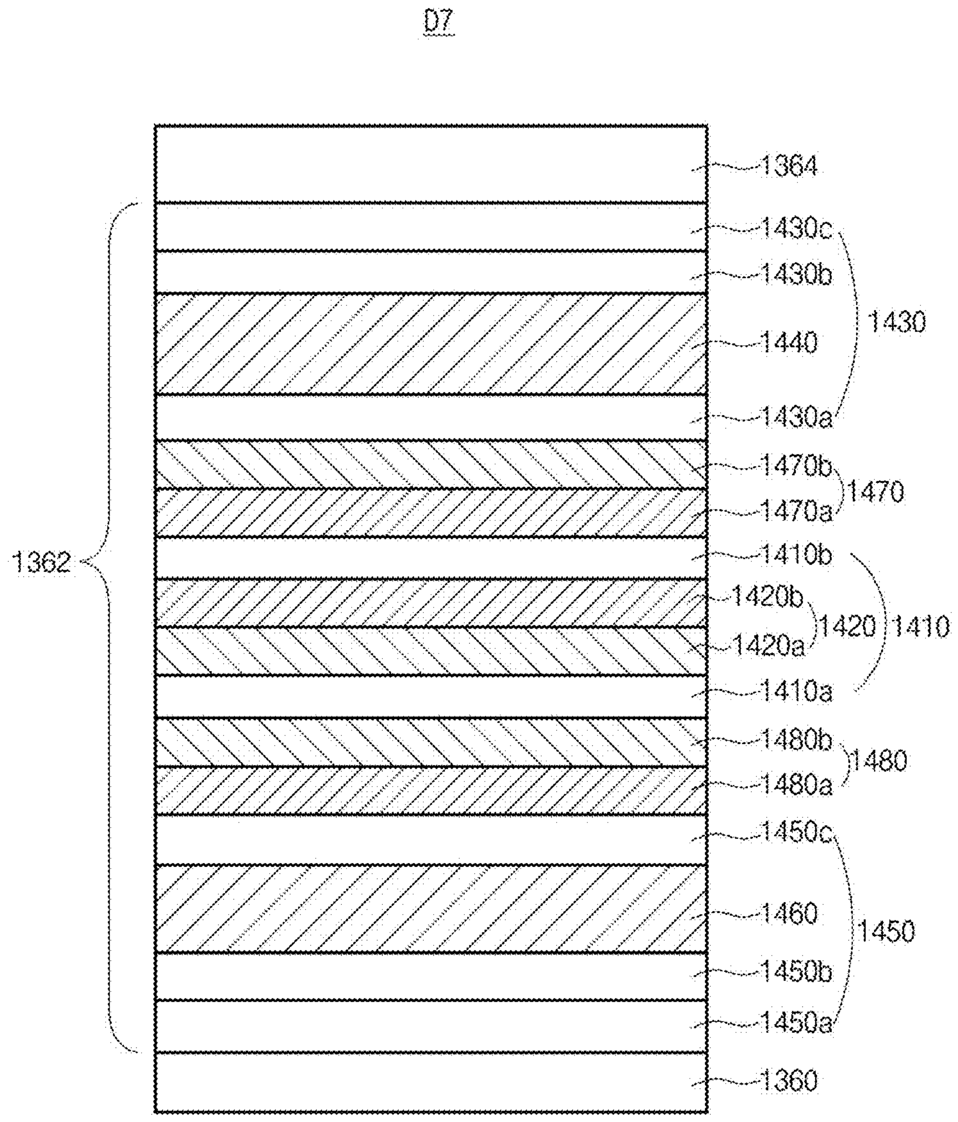

ORGANIC COMPOUND AND ORGANIC LIGHT EMITTING DIODE AND ORGANIC LIGHT EMITTING DEVICE INCLUDING THE SAME

TECHNICAL FIELD

The present disclosure relates to an organic compound, and more specifically, to an organic compound being used for an emitting material layer of an organic light emitting diode and having high emitting efficiency, and an organic light emitting diode and an organic light emitting display device including the same.

BACKGROUND ART

As requests for flat panel display devices having a small occupied area have been increased, an organic light emitting display device, which may be referred to as an organic electroluminescent device (OELD), including an organic light emitting diode (OLED) among the flat panel display device has been the subject of recent research and development.

The OLED emits light by injecting electrons from a cathode as an electron injection electrode and holes from an anode as a hole injection electrode into an emitting material layer (EML), combining the electrons with the holes, generating an exciton, and transforming the exciton from an excited state to a ground state. A flexible substrate, for example, a plastic substrate, can be used as a base substrate where elements are formed. In addition, the organic light emitting display device can be operated at a voltage (e.g., 10V or below) lower than a voltage required to operate other display devices. Moreover, the organic light emitting display device has advantages in the power consumption and the color purity.

The OLED includes a first electrode as an anode on a substrate, a second electrode as a cathode being spaced apart from and facing the first electrode and an organic emitting layer between the first and second electrodes.

To increase the emitting efficiency, the organic emitting layer may further include a hole injection layer (HIL), a hole transporting layer (HTL), an emitting material layer (EML), an electron transporting layer (ETL) and an electron injection layer (EIL) sequentially stacked on the first electrode.

The hole from the first electrode as the anode is provided into the EML through the HIL and the HTL, and the electron from the second electrode as the cathode is provided into the EML through the EIL and the ETL.

The hole and the electron in the EML are combined to generate the exciton, and the exciton is transferred from an excited state to a ground state. As a result, the light is emitted from the OLED.

The EML includes a host and a dopant. New dopant providing sufficient emitting efficiency is needed.

DISCLOSURE

Technical Problem

Accordingly, the present disclosure is directed to an organic compound, an OLED and an organic light emitting device that substantially obviate one or more of the problems due to the limitations and disadvantages of the related art.

An object of the present disclosure is to provide an organic compound being used for an emitting material layer of an organic light emitting diode and having high emitting efficiency.

Another object of the present disclosure is to provide an OLED and an organic light emitting display device including the organic compound and having improved emitting efficiency and display quality.

Additional features and advantages of the disclosure will be set forth in the description which follows, and in part will be apparent from the description, or may be learned by practice of the disclosure. The objectives and other advantages of the disclosure will be realized and attained by the structure particularly pointed out in the written description and claims hereof as well as the appended drawings.

Solution to Problem

According to an aspect, the present disclosure provides an organic compound of Formula, wherein each of X1 and X2 is independently oxygen or sulfur, and each of R1 to R6 is independently selected from the group consisting of hydrogen, deuterium, halogen, cyano, silyl, C1 to C20 alkyl group, C6 to C30 aryl group, C5 to C30 heteroaryl group and C1 to C20 amine.

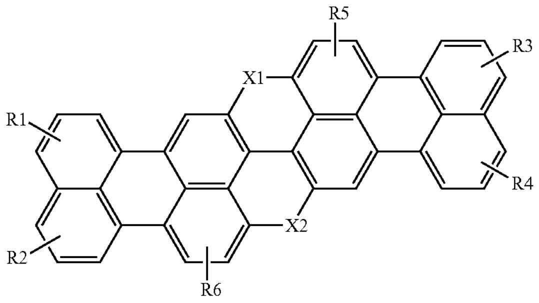

According to another aspect, the present disclosure provides an organic light emitting diode that includes a first electrode; a second electrode facing the first electrode; and a first emitting material layer positioned between the first and second electrodes, wherein the first emitting material layer includes a first compound of Formula, wherein each of X1 and X2 is independently oxygen or sulfur, and each of R1 to R6 is independently selected from the group consisting of hydrogen, deuterium, halogen, cyano, silyl, C1 to C20 alkyl group, C6 to C30 aryl group, C5 to C30 heteroaryl group and C1 to C20 amine.

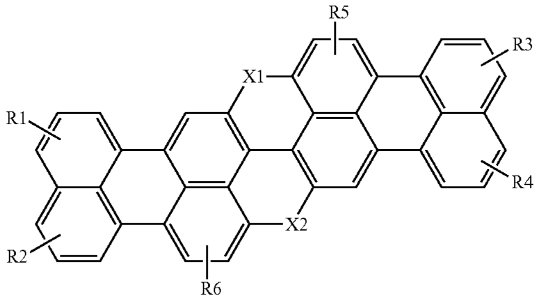

According to another aspect, the present disclosure provides an organic light emitting display device that includes a substrate; the above organic light emitting diode over the substrate; and an encapsulation film covering the organic light emitting diode.

It is to be understood that both the foregoing general description and the following detailed description are examples and are explanatory and are intended to provide further explanation of the disclosure as claimed.

Advantageous Effects

An organic compound of the present disclosure is included in an EML of an OLED and provides high emitting efficiency.

In addition, an OLED, in which an EML includes the organic compound of the present disclosure as a fluorescent dopant, and an organic light emitting device including the OLED has an advantage in the emitting efficiency.

Moreover, the EML of the OLED further includes a delayed fluorescent compound and provides high emitting efficiency and narrow full width at half maximum. Accordingly, the emitting efficiency and the display quality of the OLED and the organic light emitting device are improved.

DESCRIPTION OF DRAWINGS

The accompanying drawings, which are included to provide a further understanding of the disclosure, are incorporated in and constitute a part of this specification, illustrate implementations of the disclosure and together with the description serve to explain the principles of embodiments of the disclosure.

FIG. 1 is a schematic circuit diagram of an organic light emitting display device of the present disclosure.

FIG. 2 is a schematic cross-sectional view of an organic light emitting display device according to a first embodiment of the present disclosure.

FIG. 3 is a schematic cross-sectional view of an OLED according to a second embodiment of the present disclosure.

FIG. 4 is a view illustrating an emission mechanism of an OLED according to the second embodiment of the present disclosure.

FIG. 5 is a schematic cross-sectional view of an OLED according to a third embodiment of the present disclosure.

FIG. 6 is a schematic cross-sectional view of an OLED according to a fourth embodiment of the present disclosure.

FIG. 7 is a schematic cross-sectional view of an OLED according to a fifth embodiment of the present disclosure.

FIG. 8 is a schematic cross-sectional view of an organic light emitting display device according to a sixth embodiment of the present disclosure.

FIG. 9 is a schematic cross-sectional view of an OLED according to a seventh embodiment of the present disclosure.

FIG. 10 is a schematic cross-sectional view of an organic light emitting display device according to an eighth embodiment of the present disclosure.

FIG. 11 is a schematic cross-sectional view of an OLED according to a ninth embodiment of the present disclosure.

FIG. 12 is a schematic cross-sectional view of an OLED according to a tenth embodiment of the present disclosure.

MODE FOR INVENTION

Reference will now be made in detail to aspects of the disclosure, examples of which are illustrated in the accompanying drawings.

The present disclosure provides new organic compound, an OLED including the organic compound in an EML, and an organic light emitting device including the OLED. For example, the organic light emitting device may be an organic light emitting display device or an organic lightening device. As an example, an organic light emitting display device, which is a display device including the OLED of the present disclosure, will be mainly described.

FIG. 1 is a schematic circuit diagram of an organic light emitting display device of the present disclosure.

As shown in FIG. 1, an organic light emitting display device includes a gate line GL, a data line DL, a power line PL, a switching thin film transistor TFT Ts, a driving TFT Td, a storage capacitor Cst, and an OLED D. The gate line GL and the data line DL cross each other to define a pixel region P. The pixel region P may include a red pixel region, a green pixel region and a blue pixel region.

The switching TFT Ts is connected to the gate line GL and the data line DL, and the driving TFT Td and the storage capacitor Cst are connected to the switching TFT Ts and the power line PL. The OLED D is connected to the driving TFT Td.

In the organic light emitting display device, when the switching TFT Ts is turned on by a gate signal applied through the gate line GL, a data signal from the data line DL is applied to the gate electrode of the driving TFT Td and an electrode of the storage capacitor Cst.

When the driving TFT Td is turned on by the data signal, an electric current is supplied to the OLED D from the power line PL. As a result, the OLED D emits light. In this case, when the driving TFT Td is turned on, a level of an electric current applied from the power line PL to the OLED D is determined such that the OLED D can produce a gray scale.

The storage capacitor Cst serves to maintain the voltage of the gate electrode of the driving TFT Td when the switching TFT Ts is turned off. Accordingly, even if the switching TFT Ts is turned off, a level of an electric current applied from the power line PL to the OLED D is maintained to next frame.

As a result, the organic light emitting display device displays a desired image.

FIG. 2 is a schematic cross-sectional view of an organic light emitting display device according to a first embodiment of the present disclosure.

As shown in FIG. 2, the organic light emitting display device 100 includes a substrate 110, a TFT Tr and an OLED D connected to the TFT Tr.

The substrate 110 may be a glass substrate or a flexible substrate. For example, the flexible substrate may be a polyimide (PI) substrate, a polyethersulfone (PES) substrate, a polyethylenenaphthalate (PEN) substrate, a polyethylene terephthalate (PET) substrate or a polycarbonate (PC) substrate.

A buffer layer 122 is formed on the substrate, and the TFT Tr is formed on the buffer layer 122. The buffer layer 122 may be omitted.

A semiconductor layer 120 is formed on the buffer layer 122. The semiconductor layer 120 may include an oxide semiconductor material or polycrystalline silicon.

When the semiconductor layer 120 includes the oxide semiconductor material, a light-shielding pattern (not shown) may be formed under the semiconductor layer 120. The light to the semiconductor layer 120 is shielded or blocked by the light-shielding pattern such that thermal degradation of the semiconductor layer 120 can be prevented. On the other hand, when the semiconductor layer 120 includes polycrystalline silicon, impurities may be doped into both sides of the semiconductor layer 120.

A gate insulating layer 124 is formed on the semiconductor layer 120. The gate insulating layer 124 may be formed of an inorganic insulating material such as silicon oxide or silicon nitride.

A gate electrode 130, which is formed of a conductive material, e.g., metal, is formed on the gate insulating layer 124 to correspond to a center of the semiconductor layer 120.

In FIG. 2, the gate insulating layer 124 is formed on an entire surface of the substrate 110. Alternatively, the gate insulating layer 124 may be patterned to have the same shape as the gate electrode 130.

An interlayer insulating layer 132, which is formed of an insulating material, is formed on the gate electrode 130. The interlayer insulating layer 132 may be formed of an inorganic insulating material, e.g., silicon oxide or silicon nitride, or an organic insulating material, e.g., benzocyclobutene or photo-acryl.

The interlayer insulating layer 132 includes first and second contact holes 134 and 136 exposing both sides of the semiconductor layer 120. The first and second contact holes 134 and 136 are positioned at both sides of the gate electrode 130 to be spaced apart from the gate electrode 130.

The first and second contact holes 134 and 136 are formed through the gate insulating layer 124. Alternatively, when the gate insulating layer 124 is patterned to have the same shape as the gate electrode 130, the first and second contact holes 134 and 136 are formed only through the interlayer insulating layer 132.

A source electrode 144 and a drain electrode 146, which are formed of a conductive material, e.g., metal, are formed on the interlayer insulating layer 132.

The source electrode 144 and the drain electrode 146 are spaced apart from each other with respect to the gate electrode 130 and respectively contact both sides of the semiconductor layer 120 through the first and second contact holes 134 and 136.

The semiconductor layer 120, the gate electrode 130, the source electrode 144 and the drain electrode 146 constitute the TFT Tr. The TFT Tr serves as a driving element. Namely, the TFT Tr is the driving TFT Td (of FIG. 1).

In the TFT Tr, the gate electrode 130, the source electrode 144, and the drain electrode 146 are positioned over the semiconductor layer 120. Namely, the TFT Tr has a coplanar structure.

Alternatively, in the TFT Tr, the gate electrode may be positioned under the semiconductor layer, and the source and drain electrodes may be positioned over the semiconductor layer such that the TFT Tr may have an inverted staggered structure. In this instance, the semiconductor layer may include amorphous silicon.

Although not shown, the gate line and the data line cross each other to define the pixel region, and the switching TFT is formed to be connected to the gate and data lines. The switching TFT is connected to the TFT Tr as the driving element. In addition, the power line, which may be formed to be parallel to and spaced apart from one of the gate and data lines, and the storage capacitor for maintaining the voltage of the gate electrode of the TFT Tr in one frame may be further formed.

A planarization layer 150 is formed on an entire surface of the substrate 110 to cover the source and drain electrodes 144 and 146. The planarization layer 150 provides a flat top surface and has a drain contact hole 152 exposing the drain electrode 146 of the TFT Tr.

The OLED D is disposed on the planarization layer 150 and includes a first electrode 210, which is connected to the drain electrode 146 of the TFT Tr, a light emitting layer 220 and a second electrode 230. The light emitting layer 220 and the second electrode 230 are sequentially stacked on the first electrode 210. The OLED D is positioned in each of the red, green and blue pixel regions and respectively emits the red, green and blue light.

The first electrode 210 is separately formed in each pixel region. The first electrode 210 may be an anode and may be formed of a conductive material, e.g., a transparent conductive oxide (TCO), having a relatively high work function. For example, the first electrode 210 may be formed of indium-tin-oxide (ITO), indium-zinc-oxide (IZO), indium-tin-zinc-oxide (ITZO), tin oxide (SnO), zinc oxide (ZnO), indium-copper-oxide (ICO) or aluminum-zinc-oxide (Al:ZnO, AZO).

When the organic light emitting display device 100 is operated in a bottom-emission type, the first electrode 210 may have a single-layered structure of the transparent conductive material layer. When the Organic light emitting display device 100 is operated in a top-emission type, a reflection electrode or a reflection layer may be formed under the first electrode 210. For example, the reflection electrode or the reflection layer may be formed of silver (Ag) or aluminum-palladium-copper (APC) alloy. In this instance, the first electrode 210 may have a triple-layered structure of ITO/Ag/ITO or ITO/APC/ITO.

In addition, a bank layer 160 is formed on the planarization layer 150 to cover an edge of the first electrode 210. Namely, the bank layer 160 is positioned at a boundary of the pixel region and exposes a center of the first electrode 210 in the pixel region.

The light emitting layer 220 as an emitting unit is formed on the first electrode 210. The light emitting layer 220 may have a single-layered structure of an emitting material layer (EML) including an emitting material. Alternatively, the light emitting layer 220 may have a multi-layered structure. For example, the light emitting layer 220 may further include at least one of a hole injection layer (HIL), a hole transporting layer (HTL), an electron blocking layer (EBL), a hole blocking layer (HBL), an electron transporting layer (ETL) and an electron injection layer (EIL). The HIL, the HTL and the EBL are sequentially disposed between the first electrode 210 and the EML, and the HBL, the ETL and the EIL are sequentially disposed between the EML and the second electrode 230. In addition, the EML may have a single-layered structure or a multi-layered structure. Moreover, the light emitting layer 220 may include at least two EMLs spaced apart from each other such that the OLED may have a tandem structure.

The second electrode 230 is formed over the substrate 110 where the light emitting layer 220 is formed. The second electrode 230 covers an entire surface of the display area and may be formed of a conductive material having a relatively low work function to serve as a cathode.

For example, the second electrode 230 may be formed of aluminum (Al), magnesium (Mg), calcium (Ca), silver (Ag) or their alloy or combination. In the top-emission type organic light emitting display device 100, the second electrode 230 may have a thin profile (small thickness) to provide a light transmittance property (or a semi-transmittance property).

Although not shown, the organic light emitting display device 100 may include a color filter corresponding to the red, green and blue pixel regions. For example, when the OLED D, which has the tandem structure and emits the white light, is formed to all of the red, green and blue pixel regions, a red color filter pattern, a green color filter pattern and a blue color filter pattern may be formed in the red, green and blue pixel regions, respectively, such that a full-color display is provided.

When the organic light emitting display device 100 is operated in a bottom-emission type, the color filter may be disposed between the OLED D and the substrate 110, e.g., between the interlayer insulating layer 132 and the planarization layer 150. Alternatively, when the organic light emitting display device 100 is operated in a top-emission type, the color filter may be disposed over the OLED D, e.g., over the second electrode 230.

An encapsulation film 170 is formed on the second electrode 230 to prevent penetration of moisture into the OLED D. The encapsulation film 170 includes a first inorganic insulating layer 172, an organic insulating layer 174 and a second inorganic insulating layer 176 sequentially stacked, but it is not limited thereto.

The Organic light emitting display device 100 may further include a polarization plate (not shown) for reducing an ambient light reflection. For example, the polarization plate may be a circular polarization plate. In the bottom-emission type organic light emitting display device 100, the polarization plate may be disposed under the substrate 110. In the top-emission type organic light emitting display device 100, the polarization plate may be disposed on or over the encapsulation film 170.

In addition, in the top-emission type organic light emitting display device 100, a cover window (not shown) may be attached to the encapsulation film 170 or the polarization plate. In this instance, the substrate 110 and the cover window have a flexible property such that a flexible organic light emitting display device may be provided.

FIG. 3 is a schematic cross-sectional view of an OLED according to a second embodiment of the present disclosure.

As shown in FIG. 3, the OLED D1 includes the first and second electrodes 210 and 230, which face each other, and the light emitting layer 220 therebetween. The light emitting layer 220 includes an emitting material layer (EML) 240. The organic light emitting display device 100 (of FIG. 2) may include a red pixel region, a green pixel region and a blue pixel region, and the OLED D1 may be positioned in the green pixel region.

The first electrode 210 may be an anode, and the second electrode 230 may be a cathode.

The light emitting layer 220 further include at least one of a hole transporting layer (HTL) 260 between the first electrode 210 and the EML 240 and an electron transporting layer (ETL) 270 between the second electrode 230 and the EML 240.

In addition, the light emitting layer 220 may further include at least one of a hole injection layer (HIL) 250 between the first electrode 210 and the HTL 260 and an electron injection layer (EIL) 280 between the second electrode 230 and the ETL 270.

Moreover, the light emitting layer 220 may further include at least one of an electron blocking layer (EBL) 265 between the HTL 260 and the EML 240 and a hole blocking layer (HBL) 275 between the EML 240 and the ETL 270.

For example, the HIL 250 may include at least one compound selected from the group consisting of 4,4',4"-tris(3-methylphenylamino)triphenylamine (MTDATA), 4,4',4"-tris(N,N-diphenyl-amino)triphenylamine (NATA), 4,4',4"-tris(N-(naphthalene-1-yl)-N-phenyl-amino)triphenylamine (IT-NATA), 4,4',4"-tris(N-(naphthalene-2-yl)-N-phenyl-amino)triphenylamine (2T-NATA), copper phthalocyanine (CuPc), tris(4-carbazoyl-9-yl-phenyl)amine (TCTA), N,N'-diphenyl-N,N'-bis(1-naphthyl)-1,1'-biphenyl-4,4"-diamine (NPB; NPD), 1,4,5,8,9,11-hexaazatriphenylenehexacarbonitrile(dipyrazino[2,3-f:2'3'-h]quinoxaline-2,3,6,7,10,11-hexacarbonitrile; HAT-CN), 1,3,5-tris[4-(diphenylamino)phenyl]benzene (TDAPB), poly(3,4-ethylenedioxythiphene)polystyrene sulfonate (PEDOT/PSS), and N-(biphenyl-4-yl)-9,9-dimethyl-N-(4-(9-phenyl-9H-carbazol-3-yl)phenyl)-9H-fluoren-2-amine, but it is not limited thereto.

The HTL 260 may include at least one compound selected from the group consisting of N,N'-diphenyl-N,N'-bis(3-methylphenyl)-1,1'-biphenyl-4,4'-diamine; TPD), NPB (NPD), 4,4'-bis(N-carbazolyl)-1,1'-biphenyl (CBP), poly[N,N'-bis(4-butylpnehyl)-N,N'-bis(phenyl)-(poly[(9,9-dioctylfluorenyl-2,7-diyl)-co-(4,4'-(N-(4-sec-benzidine](Poly-TPD), butylphenyl)diphenylamine))] (TFB), di-[4-(N,N-di-p-tolyl-amino)-phenyl]cyclohexane (TAPC), 3,5-di(9H-carbazol-9-yl)-N,N-diphenylaniline (DCDPA), N-(biphenyl-4-yl)-9,9-dimethyl-N-(4-(9-phenyl-9H-carbazol-3-yl)phenyl)-9H-fluoren-2-amine, and N-(biphenyl-4-yl)-N-(4-(9-phenyl-9H-carbazol-3-yl)phenyl) biphenyl-4-amine, but it is not limited thereto.

The ETL 270 may include at least one of an oxadiazole-based compound, a triazole-based compound, a phenanthroline-based compound, a benzoxazole-based compound, a benzothiazole-based compound, a benzimidazole-based compound, and a triazine-based compound. For example, the ETL 270 may include at least one compound selected from the group consisting of tris-(8-hydroxyquinoline aluminum (Alq3), 2-biphenyl-4-yl-5-(4-t-butylphenyl)-1,3,4-oxadiazole (PBD), spiro-PBD, lithium quinolate (Liq), 1,3,5-tris(N-phenylbenzimidazol-2-yl)benzene (TPBi), bis(2-methyl-8-quinolinolato-N1,O8)-(1,1'-biphenyl-4-olato) aluminum (BAlq), 4,7-diphenyl-1,10-phenanthroline (Bphen), 2,9-bis(naphthalene-2-yl)4,7-diphenyl-1,10-phenanthroline (NBphen), 2,9-dimethyl-4,7-diphenyl-1,10-phenathroline (BCP), 3-(4-biphenyl)-4-phenyl-5-tert-butylphenyl-1,2,4-triazole (TAZ), 4-(naphthalen-1-yl)-3,5-diphenyl-4H-1,2,4-triazole (NTAZ), 1,3,5-tri(p-pyrid-3-yl-phenyl)benzene (TpPyPB), 2,4,6-tris(3'-(pyridin-3-yl)biphenyl-3-yl)1,3,5-triazine (TmPPPyTz), Poly[9,9-bis(3'-((N,N-dimethyl)-N-ethylammonium)-propyl)-2,7-fluorene]-alt-2,7-(9,9-dioctylfluorene)] (PFNBr), tris(phenylquinoxaline (TPQ), and diphenyl-4-triphenylsilyl-phenylphosphine oxide (TSPO1), but it is not limited thereto.

The EIL 280 may include at least one of an alkali halide compound, such as LiF, CsF, NaF, or BaF2, and an organometallic compound, such as Liq, lithium benzoate, or sodium stearate, but it is not limited thereto.

The EBL 265, which is positioned between the HTL 260 and the EML 240 to block the electron transfer from the EML 240 into the HTL 260, may include at least one compound selected from the group consisting of TCTA, tris[4-(diethylamino)phenyl]amine, N-(biphenyl-4-yl)-9,9-dimethyl-N-(4-(9-phenyl-9H-carbazol-3-yl)phenyl)-9H-fluoren-2-amine, TAPC, MTDATA, 1,3-bis(carbazol-9-yl)benzene (mCP), 3,3'-bis(N-carbazolyl)-1,1'-biphenyl (mCBP), CuPc, N,N'-bis[4-[bis(3-methylphenyl)amino]phenyl]-N,N'-diphenyl-[1,1'-biphenyl]-4,4'-diamine (DNTPD), TDAPB, DCDPA, and 2,8-bis(9-phenyl-9H-carbazol-3-yl)dibenzo[b,d]thiophene), but it is not limited thereto.

The HBL 275, which is positioned between the EML 240 and the ETL 270 to block the hole transfer from the EML 240 into the ETL 270, may include the above material of the ETL 270.

For example, the material of the HBL 275 has a HOMO energy level being lower than a material of the EML 240 and may be at least one compound selected from the group consisting of BCP, BAlq, Alq3, PBD, spiro-PBD, Liq, bis-4,6-(3,5-di-3-pyridylphenyl)-2-methylpyrimidine (B3PYMPM), bis[2-(diphenylphosphino)phenyl]teeth oxide (DPEPO), 9-(6-9H-carbazol-9-yl)pyridine-3-yl)-9H-3,9'-bicarbazole, and TSPO1, but it is not limited thereto.

The EML 240 includes an organic compound as a first compound being represented by Formula 1.

[Formula 1]

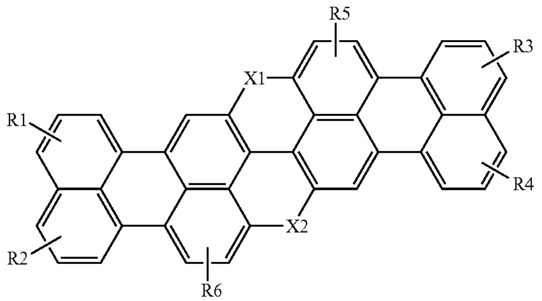

In Formula 1, each of X1 and X2 is independently oxygen (O) or sulfur (S), and each of R1 to R6 is independently selected from the group consisting of hydrogen (H), deuterium (D), halogen, cyano, silyl, C1 to C20 alkyl group, C6 to C30 aryl group, C5 to C30 heteroaryl group and C1 to C20 amine (e.g., alkyl amine or arylamine).

In the specification, the aryl group and/or the heteroaryl group may be unsubstituted or substituted. For example, the aryl group and/or the heteroaryl group may be substituted by C1 to C20 aryl.

For example, the C6 to C30 aryl group may be selected from the group consisting of phenyl, biphenyl, terphenyl, naphthyl, anthracenyl, pentanenyl, indenyl, indenoindenyl, heptalenyl, biphenylenyl, indacenyl, phenanthrenyl, benzophenanthrenyl, dibenzophenanthrenyl, azulenyl, pyrenyl, fluoranthenyl, triphenylenyl, chrysenyl, tetraphenyl, tetrasenyl, picenyl, pentaphenyl, pentacenyl, fluorenyl, indenofluorenyl and spiro-fluorenyl.

The C5 to C30 heteroaryl group may be selected from the group consisting of pyrrolyl, pyridinyl, pyrimidinyl, pyrazinyl, pyridazinyl, triazinyl, tetrazinyl, imidazolyl, pyrazolyl, indolyl, isoindolyl, indazolyl, indolizinyl, pyrrolizinyl, carbazolyl, benzocarbazolyl, dibenzocarbazolyl, indolocarbazolyl, indenocarbazolyl, benzofurocarbazolyl, benzothienocarbazolyl, quinolinyl, isoquinolinyl, phthalazinyl, quinoxalinyl, sinolinyl, quinazolinyl, quinozolinyl, quinolinyl, purinyl, phthalazinyl, quinoxalinyl, benzoquinolinyl, benzoisoquinolinyl, benzoquinazolinyl, benzoquinoxalinyl, acridinyl, phenanthrolinyl, perimidinyl, phenanthridinyl, pteridinyl, cinnolinyl, naphtharidinyl, furanyl, oxazinyl, oxazolyl, oxadiazolyl, triazolyl, dioxynyl, benzofuranyl, dibenzofuranyl, thiopyranyl, xantenyl, chromaenyl, isochromenyl, thioazinyl, thiophenyl, benzothiophenyl, dibenzothiophenyl, difuropyrazinyl, benzofurodibenzofuranyl, benzothienobenzothiophenyl, benzothienodibenzothiophenyl, benzothienobenzofuranyl, and benzothienodibenzofuranyl.

Each of R1 to R6 may be selected from the group consisting of H, methyl, isopropyl, tert-butyl, phenyl, methylphenyl, trimethylphenyl, tert-butylphenyl, diphenylamine, biphenyl and pyridyl.

For example, in Formula 1, each of X1 and X2 may be O, each of R2, R3, R5 and R6 may be H, and each of R1 and R4 may be selected from the group consisting of halogen, cyano, silyl, C1 to C20 alkyl group, C6 to C30 aryl group, C5 to C30 heteroaryl group and C1 to C20 amine (e.g., alkyl amine or arylamine). Namely, the organic compound of Formula 1 may be represented by Formula 2.

[Formula 2]

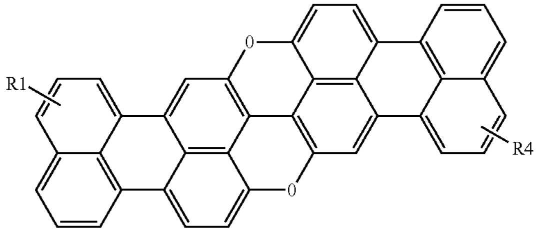

The organic compound of the present disclosure may be one of the compounds in Formula 3.

[Formula 3]

compound 1

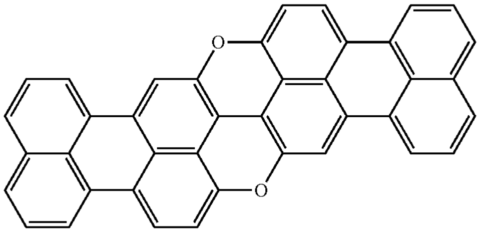

compound 2

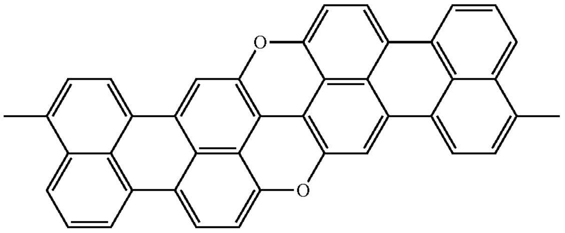

-continued
compound 3
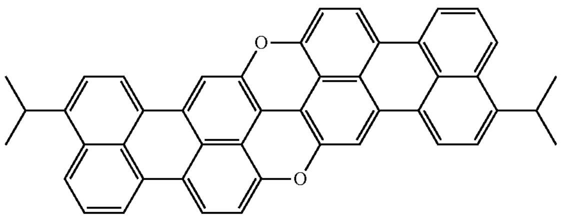
compound 4
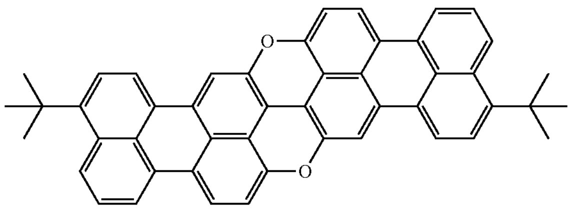
compound 5
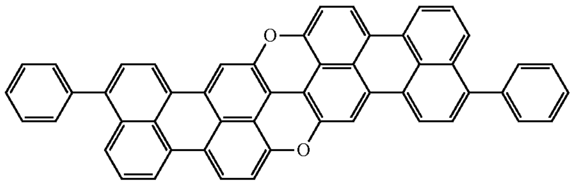
compound 6
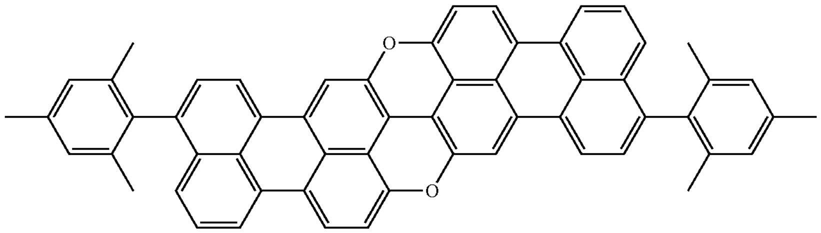
compound 7
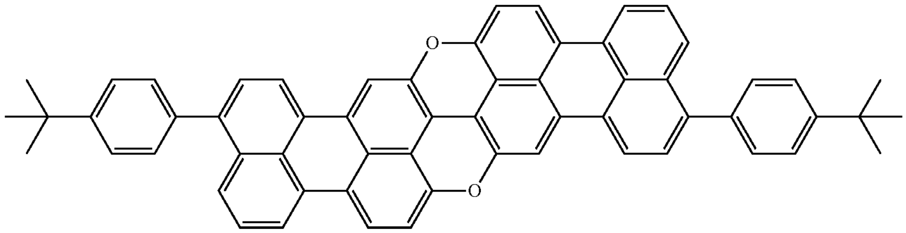
compound 8
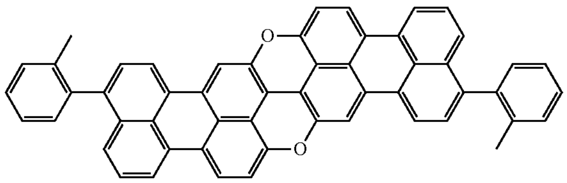
compound 9
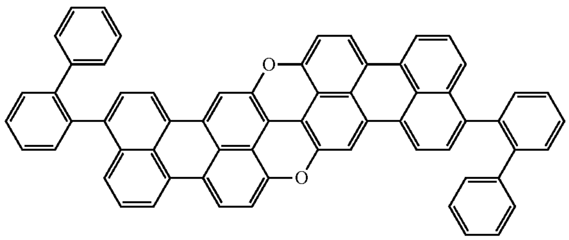
compound 10
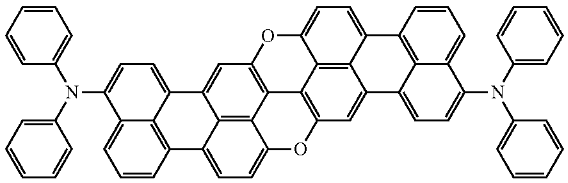
compound 11
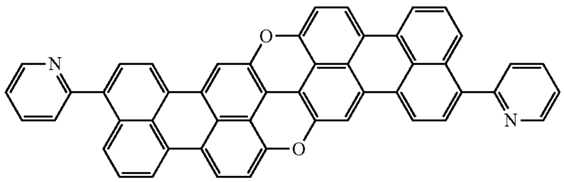

-continued
compound 12
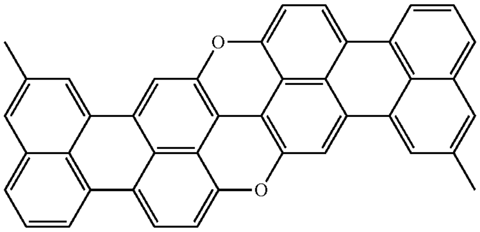
compound 13
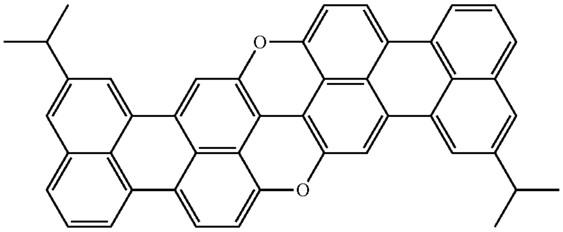
compound 14
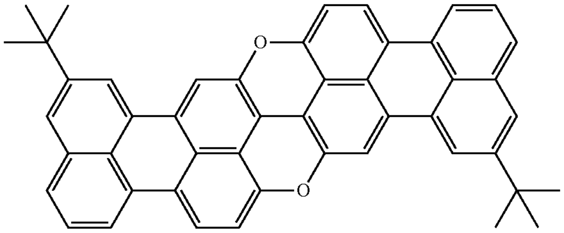
compound 15
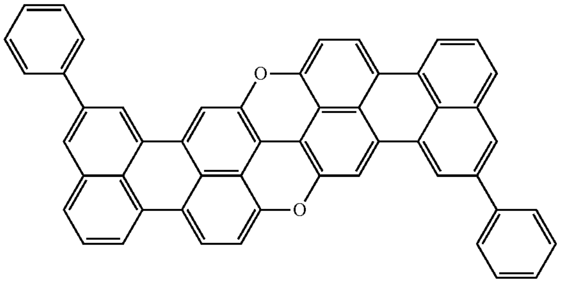
compound 16
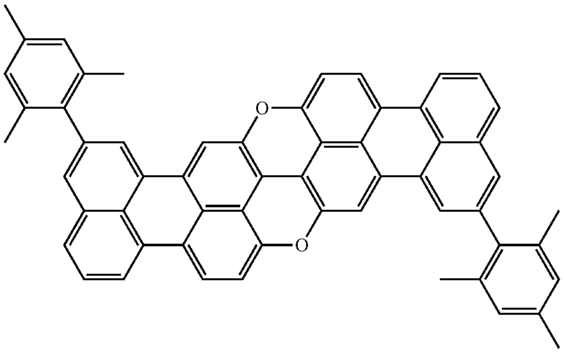
compound 17
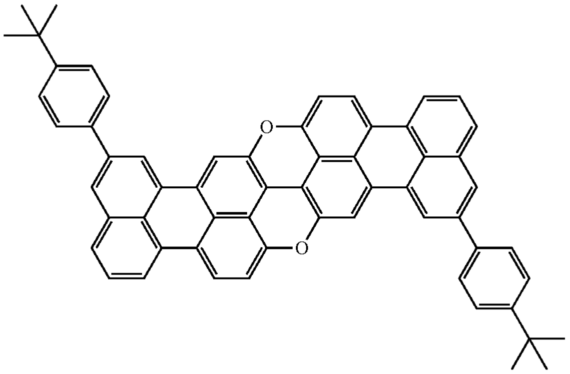
compound 18
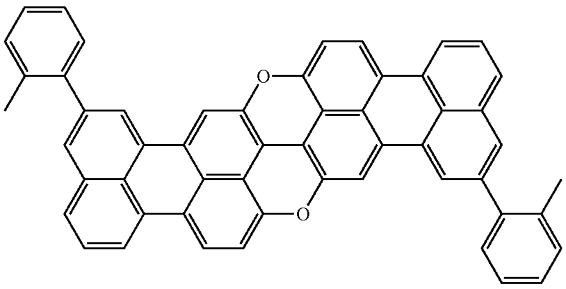
compound 19
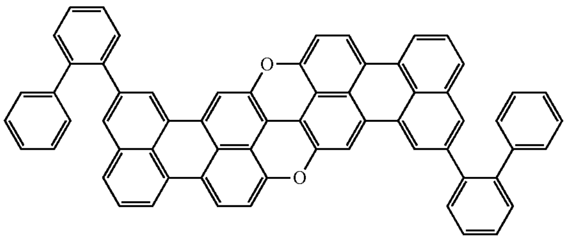
compound 20
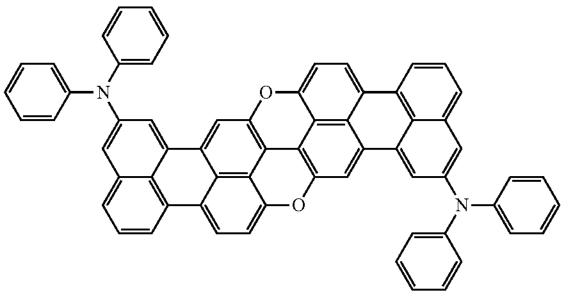
compound 21
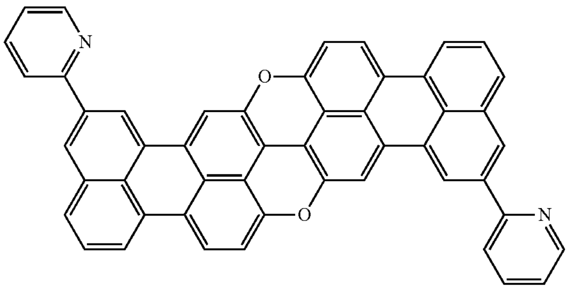

-continued
compound 22
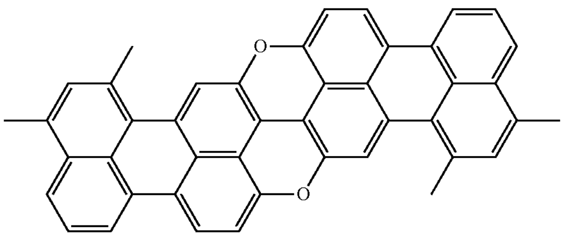
compound 23
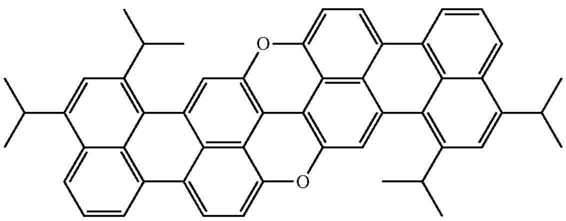
compound 24
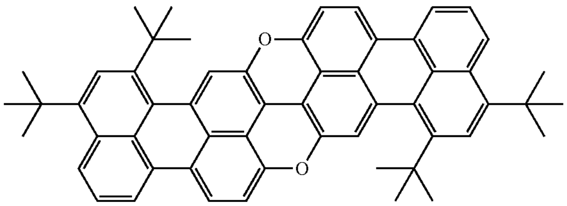
compound 25
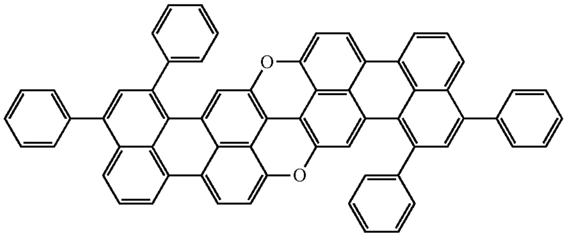
compound 26
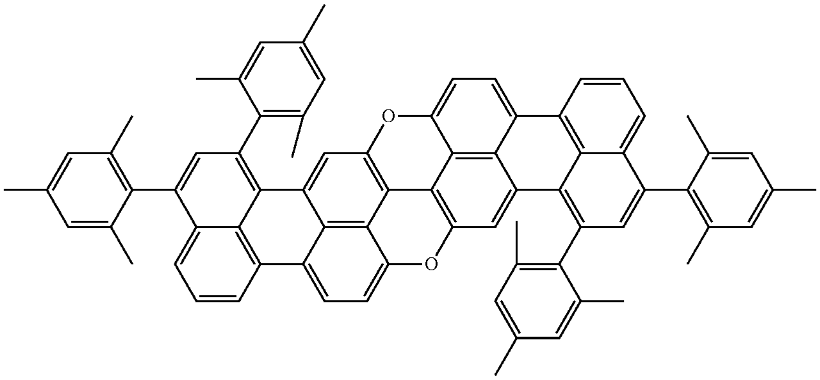
compound 27
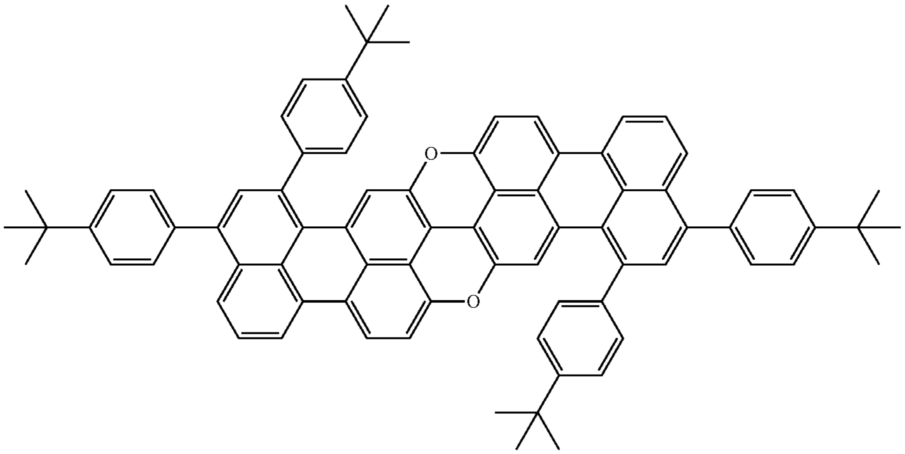
compound 28
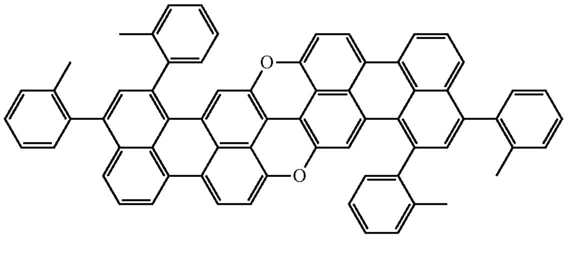

The synthesis of the organic compound of the present disclosure will be described.

[Synthesis]

1. Synthesis of the Compound 1

(1) Compound A-1

[Reaction Formula 1-1]

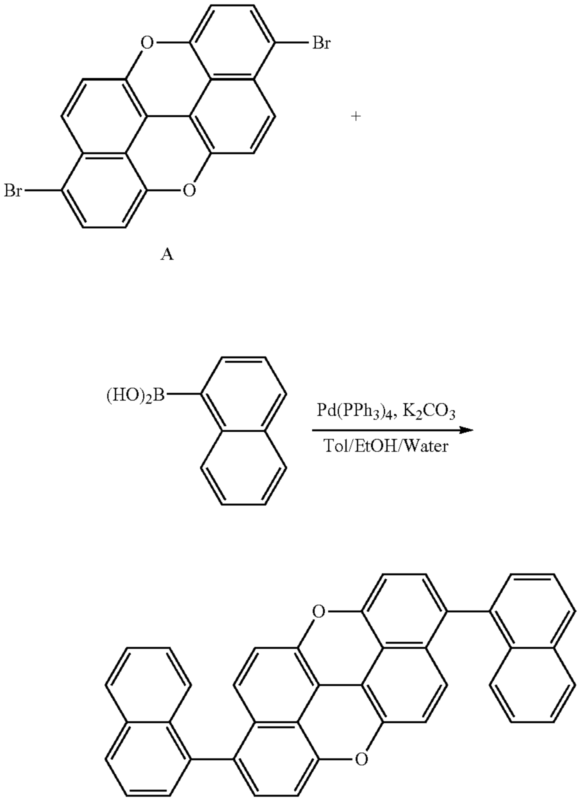

A

A-1

In a 2-neck flask (500 mL), the compound A (5.00 g, 11.36 mmol), naphthalen-1-ylboronic acid (4.30 g, 25.00 mmol), $K_2CO_3$ (7.85 g, 56.81 mmol), and $Pd(PPh_3)_4$ (0.39 g, 0.34 mmol) were added and dissolved in a mixed solvent of toluene, ethanol, and water (300 mL, volume ratio=4:1:1). The mixture was refluxed and stirred for 12 hours. After completion of the reaction, a solid compound A-1 (4.1 g, 67.5%) was obtained by column using a developing solvent of methylene chloride (MC) and hexane (volume ratio=3:7).

(2) The Compound 1

[Reaction Formula 1-2]

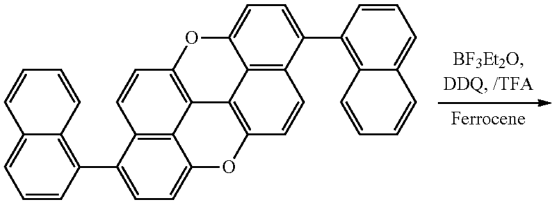

A-1

-continued

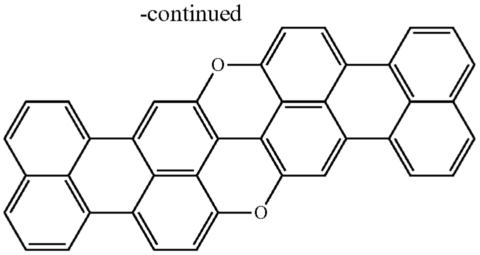

compound 1

In a 2-neck flask (500 mL), the compound A-1 (4.1 g, 7.67 mmol), $BF_3Et_2O$ (23.22 mL, 184.06 mmol), and trifluoroacetic acid (TFA, 200 mL) were added and mixed under nitrogen conditions. After dicyanobenzoquinone (DDQ, 5.22 g, 23.01 mmol) was added to the mixture and stirred for 1 hour, ferrocene (4.28 g, 23.01 mmol) was added and reacted for 12 hours or more. After the reaction was terminated by adding methanol, the precipitated solid was filtered.

The mixture was columned by using boiled toluene. A solid compound 1 (0.7 g, 17.2%) was obtained by column using a developing solvent of MC and hexane (volume ratio=2:1).

2. Synthesis of the Compound 4

(1) Compound B-1

[Reaction Formula 2-1]

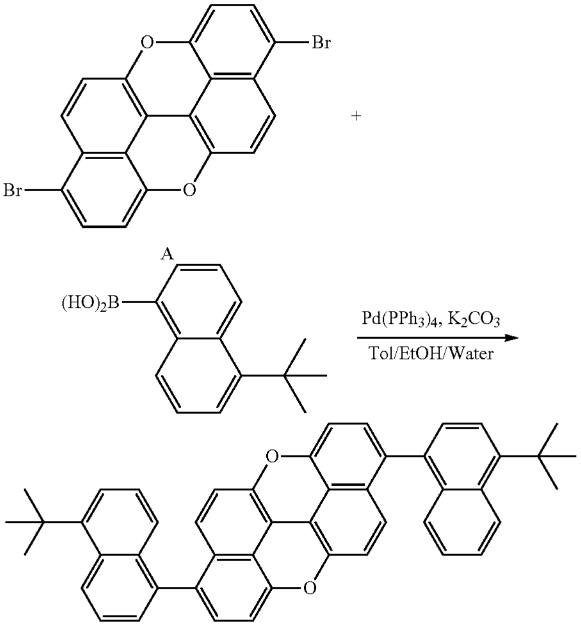

A

B-1

In a 2-neck flask (500 mL), the compound A (5.00 g, 11.36 mmol), (5-(tert-butyl) naphthalen-1-yl) boronic acid (5.70 g, 25.00 mmol), $K_2CO_3$ (7.85 g, 56.81 mmol), and $Pd(PPh_3)_4$ (0.39 g, 0.34 mmol) were added and dissolved in a mixed solvent of toluene, ethanol, and water (300 mL, volume ratio=4:1:1). The mixture was refluxed and stirred for 12 hours. After completion of the reaction, a solid compound B-1 (5.0 g, 68.0%) was obtained by column using a developing solvent of MC and hexane (volume ratio=3:7).

(2) The Compound 4

[Reaction Formula 2-2]

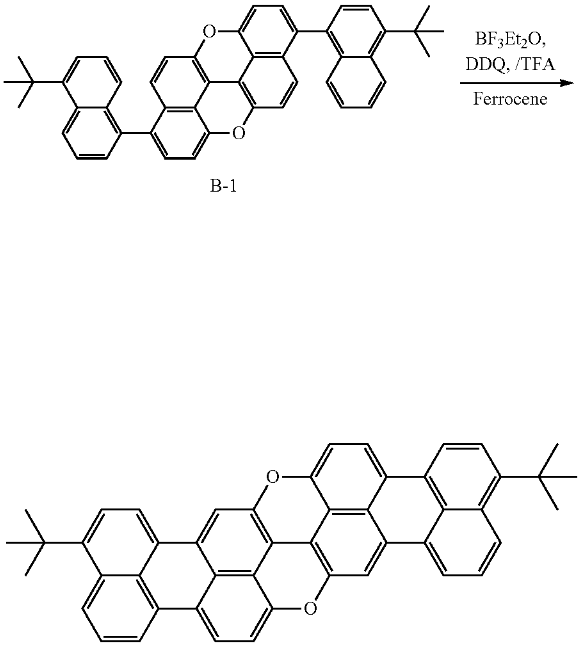

B-1 compound 4

In a 2-neck flask (500 mL), the compound B-1 (5.0 g, 7.73 mmol), $BF_3Et_2O$ (23.41 mL, 185.53 mmol), and TFA (200 mL) were added and mixed under nitrogen conditions. After DDQ (5.26 g, 23.19 mmol) was added to the mixture and stirred for 1 hour, ferrocene (4.31 g, 23.19 mmol) was added and reacted for 12 hours or more. After the reaction was terminated by adding methanol, the precipitated solid was filtered. The mixture was columned by using boiled toluene. A solid compound 4 (0.8 g, 16.10%) was obtained by column using a developing solvent of MC and hexane (volume ratio=2:1).

3. Synthesis of the Compound 5

(1) Compound C-1

[Reaction Formula 3-1]

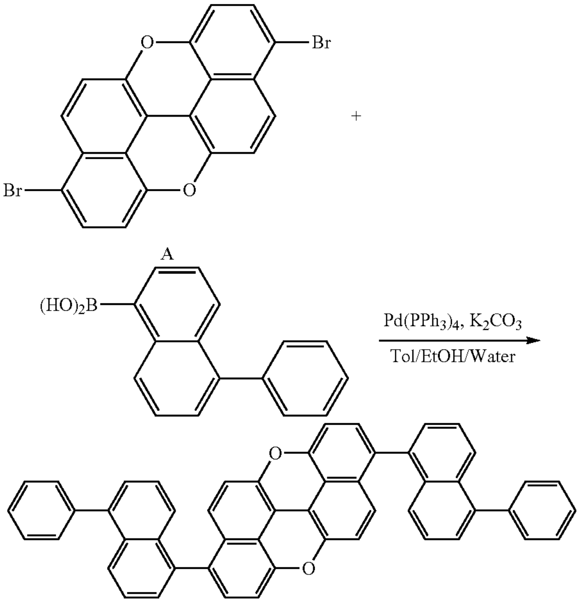

C-1

In a 2-neck flask (500 mL), the compound A (5.00 g, 11.36 mmol), (5-phenylnaphthalen-1-yl) boronic acid (6.20 g, 25.00 mmol), $K_2CO_3$ (7.85 g, 56.81 mmol), and $Pd(PPh_3)_4$ (0.39 g, 0.34 mmol) were added and dissolved in a mixed solvent of toluene, ethanol, and water (300 mL, volume ratio=4:1:1). The mixture was refluxed and stirred for 12 hours. After completion of the reaction, a solid compound C-1 (4.8 g, 61.51%) was obtained by column using a developing solvent of MC and hexane (volume ratio=3:7).

(2) The Compound 5

[Reaction Formula 3-2]

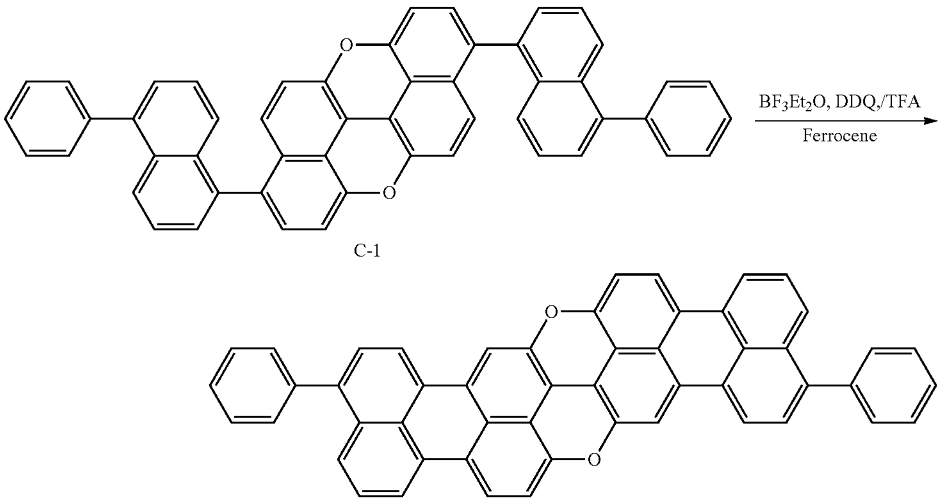

C-1 compound 5

In a 2-neck flask (500 mL), the compound C-1 (4.8 g, 6.99 mmol), $BF_3Et_2O$ (21.16 mL, 167.74 mmol), and TFA (200 mL) were added and mixed under nitrogen conditions. After DDQ (4.76 g, 20.97 mmol) was added to the mixture and stirred for 1 hour, ferrocene (3.90 g, 20.97 mmol) was added and reacted for 12 hours or more. After the reaction was terminated by adding methanol, the precipitated solid was filtered. The mixture was columned by using boiled toluene. A solid compound 5 (0.75 g, 15.7%) was obtained by column using a developing solvent of MC and hexane (volume ratio=2:1).

4. Synthesis of the Compound 14

(1) Compound D-1

[Reaction Formula 4-1]

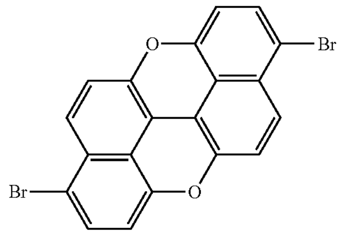

A

+

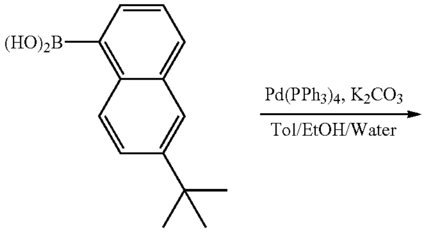

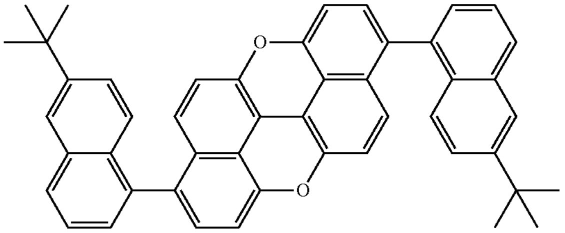

D-1

In a 2-neck flask (500 mL), the compound A (5.00 g, 11.36 mmol), (6-(tert-butyl) naphthalen-1-yl) boronic acid (5.70 g, 25.00 mmol), $K_2CO_3$ (7.85 g, 56.81 mmol), and $Pd(PPh_3)_4$ (0.39 g, 0.34 mmol) were added and dissolved in a mixed solvent of toluene, ethanol, and water (300 mL, volume ratio=4:1:1). The mixture was refluxed and stirred for 12 hours. After completion of the reaction, a solid compound D-1 (5.2 g, 70.7%) was obtained by column using a developing solvent of MC and hexane (volume ratio=3:7).

(2) The Compound 14

[Reaction Formula 4-2]

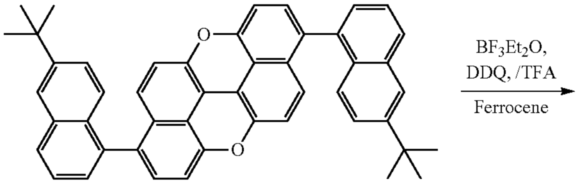

D-1

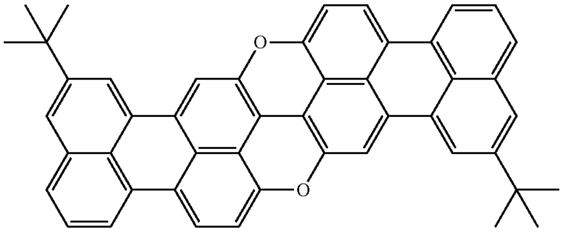

compound 14

In a 2-neck flask (500 mL), the compound D-1 (5.2 g, 8.04 mmol), $BF_3Et_2O$ (24.34 mL, 192.95 mmol), and TFA (200 mL) were added and mixed under nitrogen conditions. After DDQ (5.47 g, 24.12 mmol) was added to the mixture and stirred for 1 hour, ferrocene (4.49 g, 24.12 mmol) was added and reacted for 12 hours or more. After the reaction was terminated by adding methanol, the precipitated solid was filtered. The mixture was columned by using boiled toluene. A solid compound 14 (0.70 g, 13.6%) was obtained by column using a developing solvent of MC and hexane (volume ratio=2:1).

The EML 240 may further include a host as a second compound. For example, the organic compound of the present disclosure acts as a dopant (e.g., an emitter) and may be doped by about 0.1 to 10 wt % with respect to the host.

For example, the second compound as the host may be represented by Formula 4-1 or Formula 4-2.

[Formula 4-1]

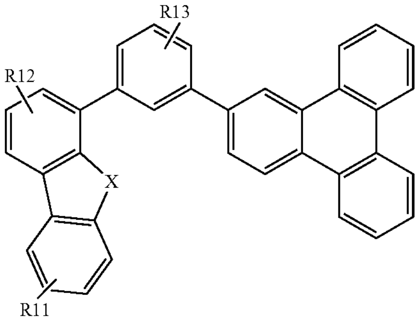

[Formula 4-2]

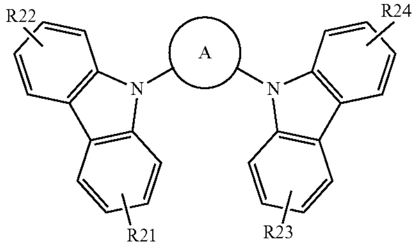

In Formula 4-1, X is O or S, and each of R11 to R13 is independently selected from the group consisting of H, D, halogen, cyano, silyl, C1 to C20 alkyl group, C6 to C30 aryl group, C5 to C30 heteroaryl group and C1 to C20 amine (e.g., alkyl amine or arylamine).

In Formula 4-2, A is selected from the group consisting of C6 to C30 arylene group and C5 to C30 heteroarylene group, and each of R21 to R24 is independently selected from the group consisting of H, D, halogen, cyano, silyl, C1 to C20 alkyl group, C6 to C30 aryl group, C5 to C30 heteroaryl group and C1 to C20 amine (e.g., alkyl amine or arylamine).

For example, A may be selected from the group consisting of phenylene, dibenzothiophenylene and dibenzofuranylene.

For example, the host may be one of the compounds of Formula 5.

[Formula 5]

H1

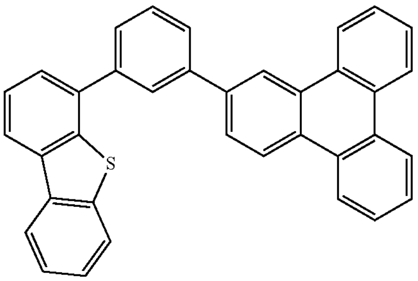

H2

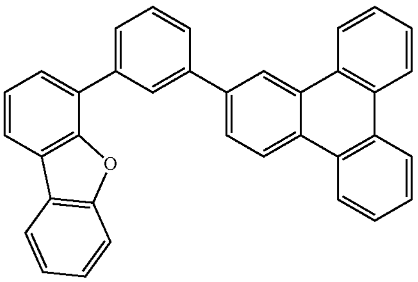

H3

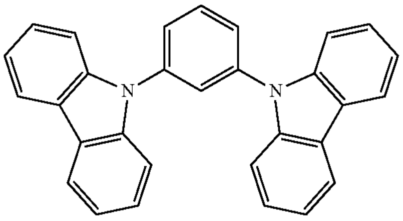

H4

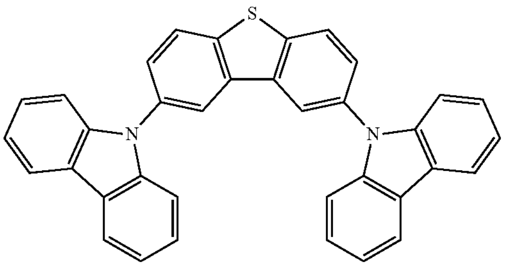

-continued

H5

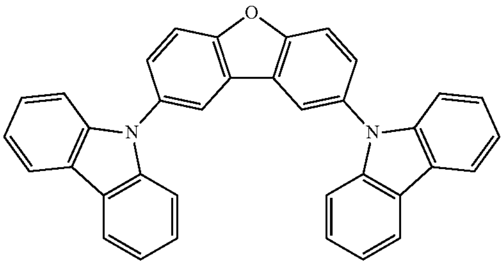

In addition, the EML 240 may further include a delayed fluorescent compound as a third compound. For example, in the EML 240, the organic compound acts as a first dopant (e.g., a fluorescent dopant), and the delayed fluorescent compound acts as a second dopant (e.g., a delayed fluorescent dopant). A summation of the first compound being the organic compound of the present disclosure and the third compound being the delayed fluorescent compound may be about 1 to 50 wt % with respect to the second compound being the host.

The weight % of the third compound may be greater than that of the first compound. In this instance, the energy of the third compound is sufficiently or efficiently transferred into the first compound such that the quantum efficiency (e.g., the emitting efficiency) of the OLED D is improved.

A difference between a singlet energy level and a triplet energy level of the third compound is very small (is less than about 0.3 eV). The energy of the triplet exciton of the third compound is converted into the singlet exciton of third compound by a reverse intersystem crossing (RISC).

Namely, in the third compound, the triplet exciton is activated by an electric field or a heat and up-converted into the singlet exciton such that the singlet exciton and the triplet exciton are involved in the light emission.

In the OLED, in which the EML 240 includes the organic compound of the present disclosure as the first compound and the delayed fluorescent compound as the third compound, the energy of the singlet exciton and the energy of the triplet exciton are transferred into the fluorescent dopant being the organic compound of the present disclosure, and the light emission is provide from the fluorescent dopant. Accordingly, the quantum efficiency of the OLED D is increased, and the full width at half maximum (FWHM) of the OLED D is narrowed.

Referring to FIG. 4, which is a view illustrating an emission mechanism of an OLED including the organic compound of the present disclosure as the first compound, the host as the second compound and the delayed fluorescent compound as the third compound, the triplet energy ($E_{T1}$(TD)) of the third compound is converted into the singlet energy ($E_{S1}$(TD)) of the third compound by RISC, and the singlet energy ($E_{S1}$(TD)) of the third compound is transferred into the singlet energy ($E_{S1}$(FD)) of the first compound (Foster Resonance Energy Transfer, FRET). As a result, the light emission is provided from the first compound. In this instance, the singlet energy ($E_{S1}$(TD)) of the third compound is greater than the singlet energy ($E_{S1}$(FD)) of the first compound.

In addition, the singlet energy ($E_{S1}$(H)) of the second compound being the host is greater than the singlet energy ($E_{S1}$(TD)) of the third compound. Moreover, the triplet energy ($E_{T1}$(TD)) of the third compound is smaller than the triplet energy ($E_{T1}$(H)) of the second compound and is greater than the triplet energy ($E_{T1}$(FD)) of the first compound. Furthermore, the singlet energy ($E_{S1}$(H)) of the second compound is greater than the singlet energy ($E_{S1}$(FD)) of the first compound.

If the above relations are not satisfied, a quenching problem is generated in the third compound and/or the first compound, or the energy transfer from the second compound into the third compound is insufficiently generated. As a result, the quantum efficiency of the OLED D is decreased.

A difference between a highest occupied molecular orbital (HOMO) level of the third compound and a HOMO level of the first compound being the organic compound of the present disclosure is equal to or less than 0.3 eV. When the difference between the HOMO level of the third compound and the HOMO level of the first compound is greater than 0.3 eV, the hole is trapped in the HOMO level of the first compound such that high quantum efficiency of the third compound is not available.

The third compound being the delayed fluorescent compound may be represented by Formula 6-1.

[Formula 6-1]

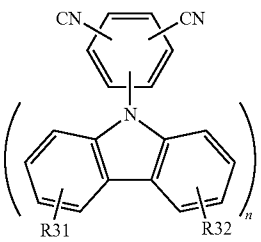

In Formula 6-1, n is an integer of 1 to 4. Each of R31 and R32 is independently selected from the group consisting of H, D, tritium (T), a C1 to C20 alkyl group, a C6 to C30 aryl group and a C3 to C40 heteroaryl group, or adjacent two of R31 and/or adjacent two of R32 are combined (or bonded) to form a fused ring. The fused ring may be a C6-C20 fused alicyclic ring, a C4-C20 fused heteroalicyclic ring, a C6-C20 fused aromatic ring or a C5-C20 fused heteroaromatic ring.

For example, n may be 3 or 4, and each of R31 and R32 may be independently selected from H, a C1 to C20 alkyl, e.g., methyl, and a C6 to C30 aryl, e.g., phenyl.

Namely, the third compound in Formula 6-1 may have a structure in which at least two cyano moieties and at least one carbazole moiety are bonded to a benzene core and may be one of the compounds in Formula 6-2.

[Formula 6-2]

1-1

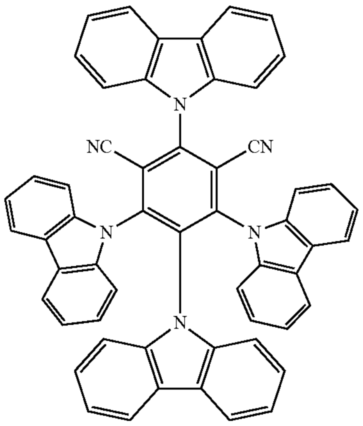

1-2

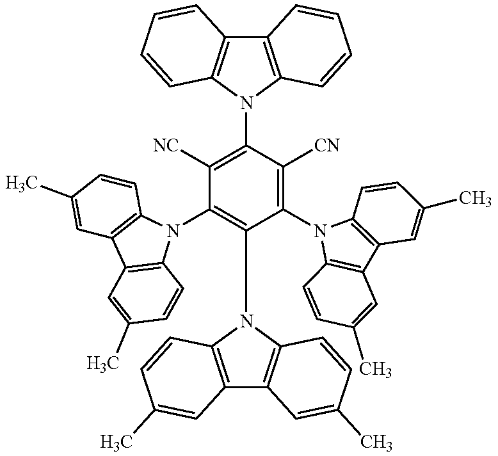

1-3

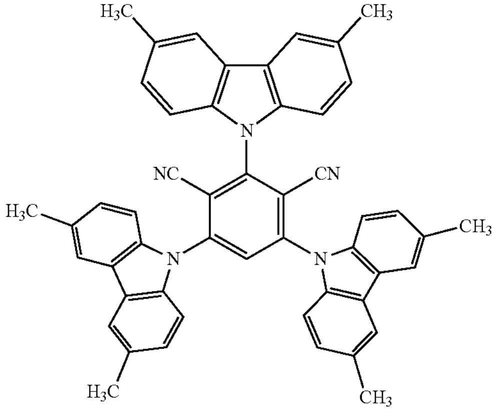

-continued
1-4
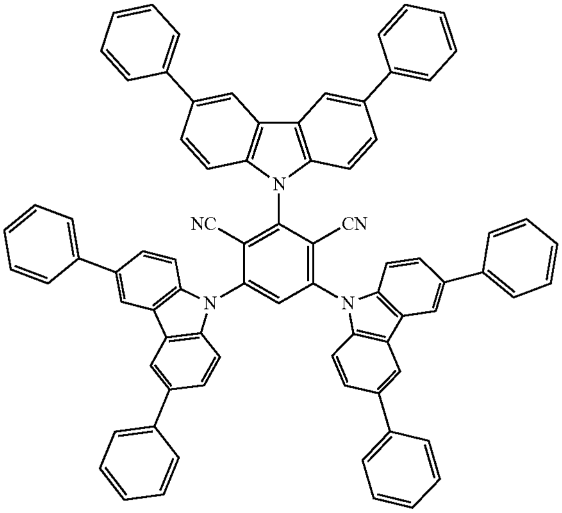
1-5
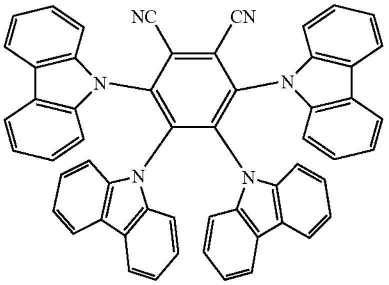
1-6
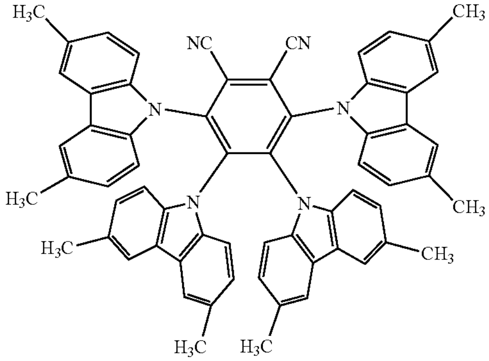
-continued
1-7
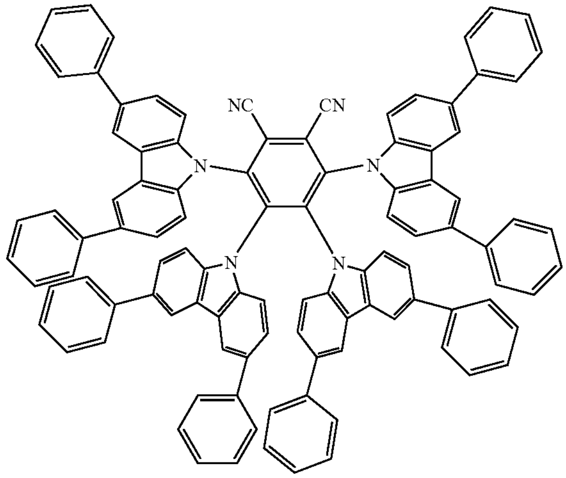
1-8
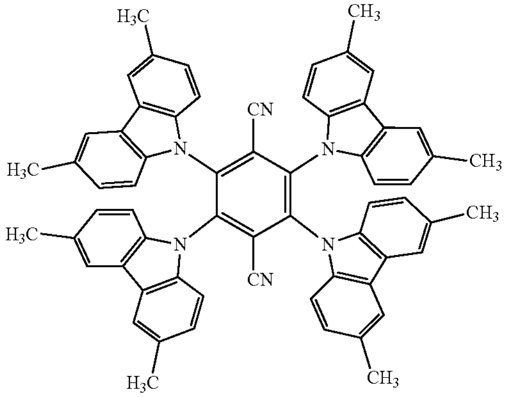
1-9
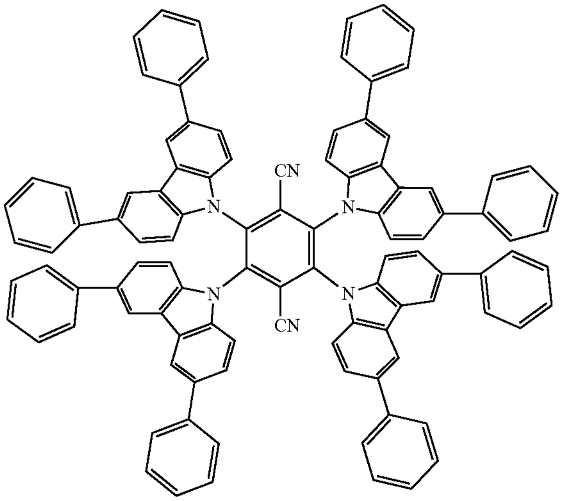

-continued 1-10

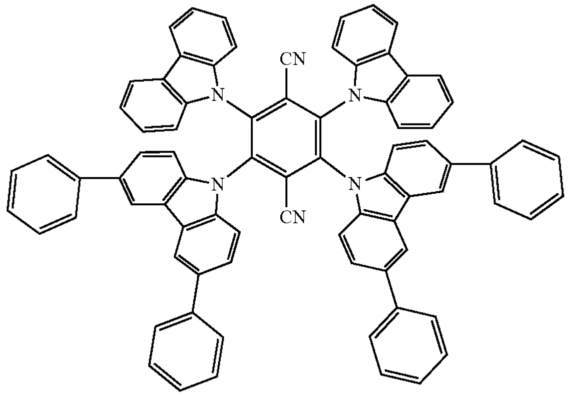

1-11

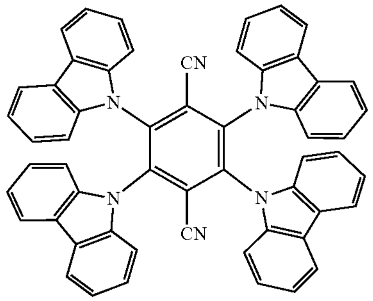

Alternatively, the third compound being the delayed fluorescent compound may be one of the compounds in Formula 7.

[Formula 7]

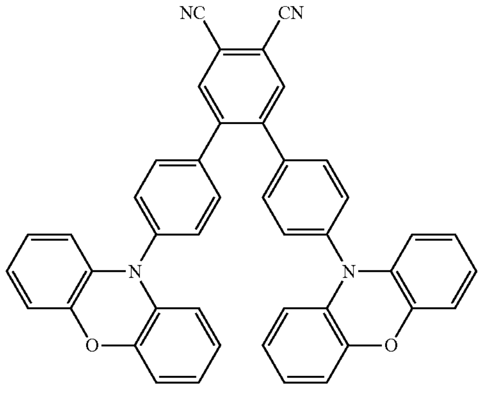

-continued

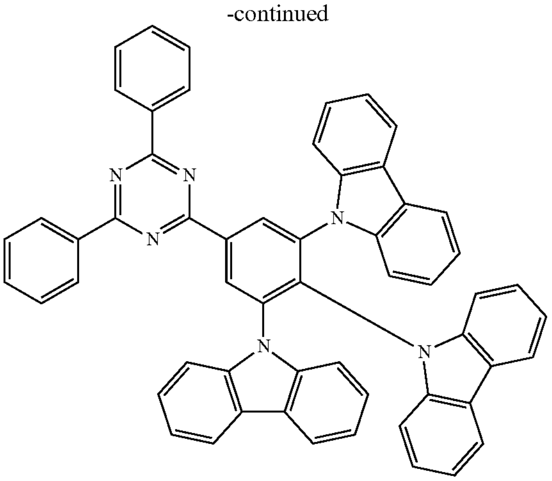

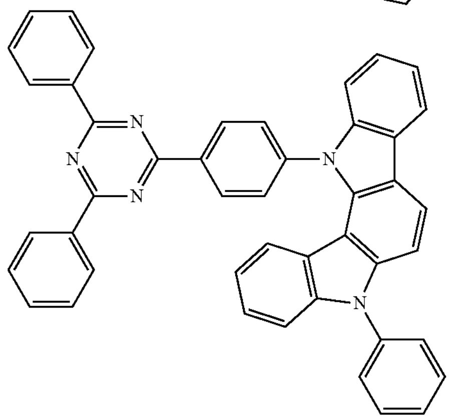

As describe above, the organic compound of the present disclosure is used as a dopant, e.g., an emitter, in the EML, and the OLED D including the organic compound of the present disclosure can provide the green emission with high emitting efficiency.

In addition, the EML of the OLED further includes the delayed fluorescent compound as a second dopant, e.g., an auxiliary dopant, with the organic compound of the present disclosure as a first dopant, the OLED D can provide high color purity by the first dopant and high quantum efficiency by the second dopant.

[OLED]

On an anode (ITO), an HIL (7 nm, the compound in Formula 8-1), an HTL (55 nm, the compound in Formula 8-2), an EBL (10 nm, the compound in Formula 8-3), an EML (35 nm), an HBL (10 nm, the compound in Formula 8-4), an ETL (20 nm the compound in Formula 8-5), an EIL (LiF) and a cathode (Al) are sequentially stacked to form the OLED.

(1) COMPARATIVE EXAMPLE (REF)

The compound in Formula 8-6 (0.5 wt %), the compound in Formula 8-7 (35 wt %, the delayed fluorescent compound), and the compound H1 in Formula 5 (64.5 wt %) are used to form the EML.

(2) EXAMPLE 1 (EX1)

The compound 1 in Formula 3 (0.5 wt %), the compound 1-1 in Formula 6-2 (35 wt %, the delayed fluorescent compound), and the compound H1 in Formula 5 (64.5 wt %) are used to form the EML.

(3) EXAMPLE 2 (EX2)

The compound 4 in Formula 3 (0.5 wt %), the compound 1-1 in Formula 6-2 (35 wt %, the delayed fluorescent compound), and the compound H1 in Formula 5 (64.5 wt %) are used to form the EML.

(4) EXAMPLE 3 (EX3)

The compound 5 in Formula 3 (0.5 wt %), the compound 1-1 in Formula 6-2 (35 wt %, the delayed fluorescent compound), and the compound H1 in Formula 5 (64.5 wt %) are used to form the EML.

(5) EXAMPLE 4 (EX4)

The compound 14 in Formula 3 (0.5 wt %), the compound 1-1 in Formula 6-2 (35 wt %, the delayed fluorescent compound), and the compound H1 in Formula 5 (64.5 wt %) are used to form the EML.

[Formula 8-1]

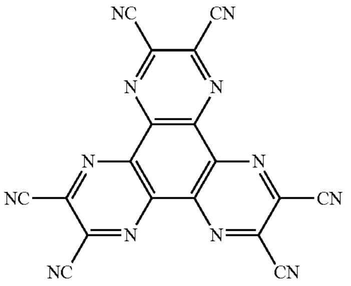

[Formula 8-2]

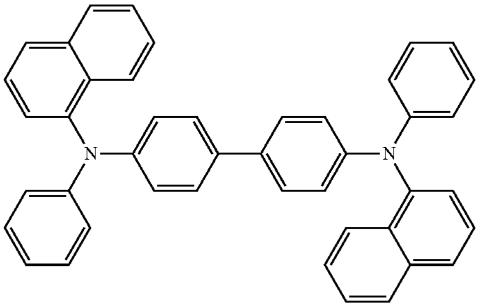

[Formula 8-3]

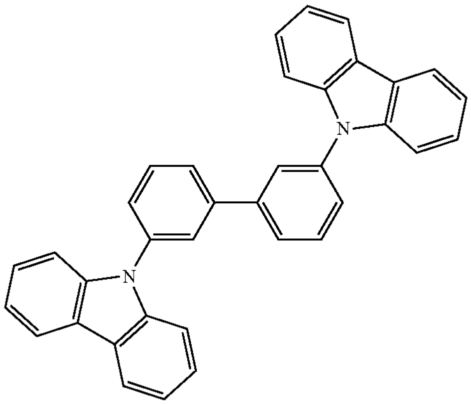

-continued

[Formula 8-4]

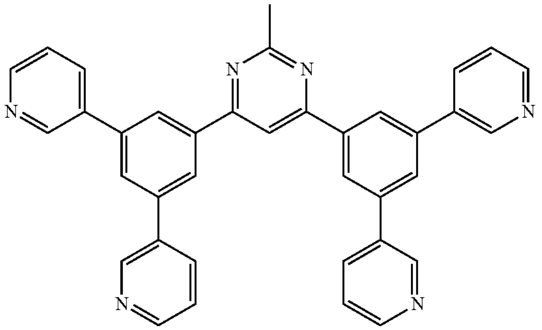

[Formula 8-5]

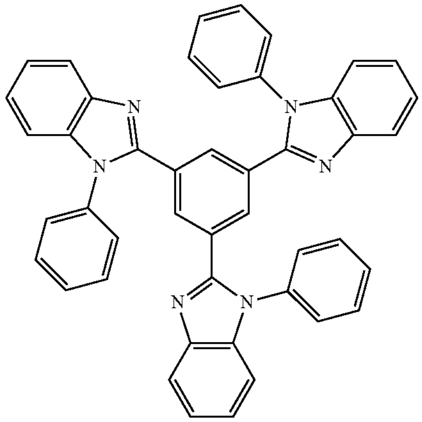

[Formula 8-6]

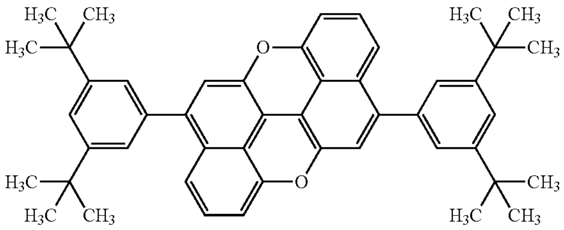

[Formula 8-7]

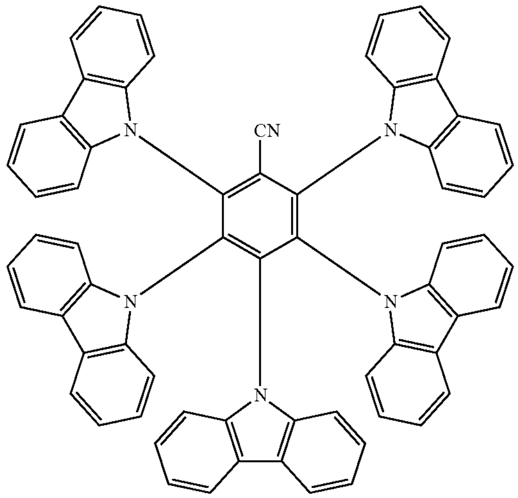

The emitting properties, i.e., the driving voltage (V), the current efficiency (cd/A), the power efficiency (lm/W), the external quantum efficiency (EQE, %) and the EL maximum value (ELmax, nm), of the OLED in Comparative Example and Examples 1 to 4 are measured and listed in Table 1.

TABLE 1

| | @ 6.3 mA/cm$^2$ | | | | |
|---|---|---|---|---|---|
| | V | cd/A | lm/W | EQE | EL $\lambda_{max}$ |
| Ref | 4.44 | 11.0 | 7.8 | 5.1 | 492 |
| Ex1 | 3.8 | 48.6 | 40.2 | 14.8 | 538 |
| Ex2 | 4.1 | 60.2 | 46.2 | 18.0 | 540 |
| Ex3 | 4.0 | 47.9 | 37.8 | 15.6 | 548 |
| Ex4 | 3.9 | 54.8 | 43.8 | 16.5 | 539 |

As shown in Table 1, in the OLED including the organic compound of the present disclosure, the emitting efficiency of the OLED is improved, and the OLED provide the green emission having a desired wavelength range.

FIG. 5 is a schematic cross-sectional view of an OLED according to a third embodiment of the present disclosure.

As shown in FIG. 5, an OLED D2 according to the third embodiment of the present disclosure includes the first and second electrodes 310 and 330, which face each other, and the light emitting layer 320 therebetween. The light emitting layer 320 includes an EML 340. The organic light emitting display device 100 (of FIG. 2) may include a red pixel region, a green pixel region and a blue pixel region, and the OLED D2 may be positioned in the green pixel region.

The first electrode 310 may be an anode, and the second electrode 330 may be a cathode.

The light emitting layer 320 may further include at least one of the HTL 360 between the first electrode 310 and the EML 340 and the ETL 370 between the second electrode 330 and the EML 340.

In addition, the light emitting layer 320 may further include at least one of the HIL 350 between the first electrode 310 and the HTL 360 and the EIL 380 between the second electrode 330 and the ETL 370.

Moreover, the light emitting layer 320 may further include at least one of the EBL 365 between the HTL 360 and the EML 340 and the HBL 375 between the EML 340 and the ETL 370.

The EML 340 includes a first EML (a first layer or a lower emitting material layer) 342 and a second EML (a second layer or an upper emitting material layer) 344 sequentially stacked over the first electrode 310. Namely, the second EML 344 is positioned between the first EML 342 and the second electrode 330.

In the EML 340, one of the first and second EMLs 342 and 344 includes the first compound being the organic compound of the present disclosure in Formulas 1 to 3, and the other one of the first and second EMLs 342 and 344 includes the delayed fluorescent compound. For example, the delayed fluorescent compound may be the third compound in Formulas 6-1, 6-2 and 7. In addition, the first and second EMLs 342 and 344 further include a fourth compound and a fifth compound as a host, respectively. The fourth compound in the first EML 342 and the fifth compound in the second EML 344 may be same or different. For example, each of the host of the first EML 342, i.e., the fourth compound, and the host of the second EML 344, i.e., the fifth compound, may be the above second compound in Formulas 4-1, 4-2 and 5.

The OLED, where the first EML 342 includes the first compound being the organic compound of the present disclosure, will be explained.

The third compound having a delayed fluorescent property has high quantum efficiency. However, since the third compound has wide FWHM, the third compound has a disadvantage in a color purity. On other hand, the first compound having a fluorescent property has narrow FWHM. However, the triplet exciton of the first compound is not involved in the emission, the first compound has a disadvantage in an emitting efficiency.

In the OLED D2, since the triplet exciton energy of the third compound in the second EML 344 is converted into the singlet exciton energy of the third compound by the RISC, and the singlet exciton energy of the third compound is transferred into the singlet exciton energy of the first compound in the first EML 342. As a result, the first compound provides the emission.

Accordingly, both the singlet exciton energy and the triplet exciton energy are involved in the emission such that the emitting efficiency is improved. In addition, since the emission is provided from the first compound of the fluorescent material, the emission having narrow FWHM is provided.

In the first EML 342, a weight % of the fourth compound may be equal to or greater than that of the first compound. In addition, in the second EML 344, the weight % of the fifth compound may be equal to or greater than the third compound.

Moreover, the weight % of the first compound in the first EML 342 may be smaller than that of the third compound in the second EML 344. As a result, the energy transfer by the FRET from the third compound in the second EML 344 into the first compound in the first EML 342 may be sufficiently or efficiently generated. For example, the weight % of the first compound in the first EML 342 may be 0.1 to 10, preferably 0.1 to 5, and the weight % of the third compound in the second EML 344 may be 1 to 50, preferably 10 to 40, and more preferably 20 to 40.

The host in the first EML 342 may be same as a material of the EBL 365. In this instance, the first EML 342 may have an electron blocking function with an emission function. Namely, the first EML 342 may serve as a buffer layer for blocking the electron. When the EBL 365 is omitted, the first EML 342 may serve as an emitting material layer and an electron blocking layer.

When the first compound in included in the second EML 344 and the third compound is included in the first EML 342, the host in the second EML 344 may be same as a material of the HBL 375. In this instance, the second EML 344 may have a hole blocking function with an emission function. Namely, the second EML 344 may serve as a buffer layer for blocking the hole. When the HBL 375 is omitted, the second EML 344 may serve as an emitting material layer and a hole blocking layer.

FIG. 6 is a schematic cross-sectional view of an OLED according to a fourth embodiment of the present disclosure.

As shown in FIG. 6, an OLED D3 according to the fourth embodiment of the present disclosure includes the first and second electrodes 410 and 430, which face each other, and the light emitting layer 420 therebetween. The light emitting layer 420 includes an EML 440. The organic light emitting display device 100 (of FIG. 2) may include a red pixel region, a green pixel region and a blue pixel region, and the OLED D3 may be positioned in the green pixel region.

The first electrode 410 may be an anode, and the second electrode 430 may be a cathode.

The light emitting layer 420 may further include at least one of the HTL 460 between the first electrode 410 and the EML 440 and the ETL 470 between the second electrode 430 and the EML 440.

In addition, the light emitting layer 420 may further include at least one of the HIL 450 between the first electrode 410 and the HTL 460 and the EIL 480 between the second electrode 430 and the ETL 470.

Moreover, the light emitting layer 420 may further include at least one of the EBL 465 between the HTL 460 and the EML 440 and the HBL 475 between the EML 440 and the ETL 470.

The EML 440 includes a first EML (a first layer, an intermediate emitting material layer) 442, a second EML (a second layer, a lower emitting material layer) 444 between the first EML 442 and the first electrode 410, and a third EML (a third layer, an upper emitting material layer) 446 between the first EML 442 and the second electrode 430. Namely, the EML 440 has a triple-layered structure of the second EML 444, the first EML 442 and the third EML 446 sequentially stacked.

For example, the first EML 442 may be positioned between the EBL 465 and the HBL 475, the second EML 444 may be positioned between the EBL 465 and the first EML 442, and the third EML 446 may be positioned between the HBL 475 and the first EML 442.

The first EML 442 includes a delayed fluorescent compound (material). For example, the delayed fluorescent compound may be the third compound in Formulas 6-1, 6-2 and 7. Each of the second and third EMLs 444 and 446 includes a fluorescent compound (material). At least one of the fluorescent compound in the second EMLs 444 and the fluorescent compound in third EML 446 is the first compound in Formulas 1 to 3. The first compound in the first EML 444 and the first compound in the third EML 446 may be same or different. In addition, the first to third EMLs 442, 444 and 446 further include a sixth compound, a seventh compound and an eighth compound as a host, respectively. The sixth compound in the first EML 442, the seventh compound in the second EML 444 and the eighth compound in the third EML 446 may be same or different. For example, each of the host of the first EML 442, i.e., the sixth compound, the host of the second EML 444, i.e., the seventh compound, and the host of the third EML 446, i.e., the eighth compound may be the second compound in Formulas 4-1, 4-2 and 5.

In the OLED D3, since the triplet exciton energy of the third compound in the first EML 442 is converted into the singlet exciton energy of the third compound by the RISC, and the singlet exciton energy of the third compound is transferred into the singlet exciton energy of the first compound in the second EML 444 and into the singlet exciton energy of the first compound in the third EML 446. As a result, the first compound in the second and third EMLs 444 and 446 provides the emission. Accordingly, both the singlet exciton energy and the triplet exciton energy are involved in the emission such that the emitting efficiency is improved. In addition, since the emission is provided from the first compound being the fluorescent material, the emission having narrow FWHM is provided.

In the first EML 442, the weight ratio of the sixth compound may be equal to or greater than that of the third compound. In the second EML 444, the weight ratio of the seventh compound may be equal to or less than that of the first compound. In the third EML 446, the weight ratio of the eighth compound may be equal to or less than that of the first compound.

In addition, a weight ratio of the third compound in the first EML 442 may be greater than each of that of the first compound in the second EML 444 and that of the first compound in the third EML 446. As a result, the energy is sufficiently and/or efficiently transferred from the third compound in the first EML 442 into the first compound in the second EML 444 and the first compound in the third EML 446 by the FRET. For example, the third compound may have a weight % of about 1 to 50 in the first EML 442, preferably about 10 to 40, more preferably about 20 to 40. The second compound may have a weight % of about 0.1 to 10 in each of the second EML 444 and the third EML 446, preferably about 0.1 to 5.

The host of the second EML 444 may be same as a material of the EBL 465. In this instance, the second EML 444 may have an electron blocking function with an emission function.

Namely, the second EML 444 may serve as a buffer layer for blocking the electron. When the EBL 465 is omitted, the second EML 444 may serve as an emitting layer and an electron blocking layer.

The host of the third EML 446 may be same as a material of the HBL 475. In this instance, the third EML 446 may have a hole blocking function with an emission function. Namely, the third EML 446 may serve as a buffer layer for blocking the hole. When the HBL 475 is omitted, the third EML 446 may serve as an emitting layer and a hole blocking layer.

The host in the second EML 444 may be same as a material of the EBL 465, and the host in the third EML 446 may be same as a material of the HBL 475. In this instance, the second EML 444 may have an electron blocking function with an emission function, and the third EML 446 may have a hole blocking function with an emission function. Namely, the second EML 444 may serve as a buffer layer for blocking the electron, and the third EML 446 may serve as a buffer layer for blocking the hole. When the EBL 465 and the HBL 475 are omitted, the second EML 444 may serve as an emitting material layer and an electron blocking layer and the third EML 446 serves as an emitting material layer and a hole blocking layer.

FIG. 7 is a schematic cross-sectional view of an OLED according to a fifth embodiment of the present disclosure.

As shown in FIG. 7, the OLED D4 includes the first and second electrodes 510 and 530, which face each other, and the light emitting layer 520 therebetween. The organic light emitting display device 100 (of FIG. 2) may include a red pixel region, a green pixel region and a blue pixel region, and the OLED D4 may be positioned in the green pixel region.

The first electrode 510 may be an anode, and the second electrode 530 may be a cathode.

The light emitting layer 520 includes a first emitting part 540 including a first EML 550 and a second emitting part 560 including a second EML 570. In addition, the light emitting layer 520 may further include a charge generation layer (CGL) 580 between the first and second emitting parts 540 and 560.

The CGL 580 is positioned between the first and second emitting parts 540 and 560 such that the first emitting part 540, the CGL 580 and the second emitting part 560 are sequentially stacked on the first electrode 510. Namely, the first emitting part 540 is positioned between the first electrode 510 and the CGL 580, and the second emitting part 580 is positioned between the second electrode 530 and the CGL 580.

The first emitting part 540 includes the first EML 550.

In addition, the first emitting part 540 may further include at least one of a first HTL 540*b* between the first electrode 510 and the first EML 550, an HIL 540*a* between the first electrode 510 and the first HTL **540*b*, and a first ETL 540*e* between the first EML 550 and the CGL 580**.

Moreover, the first emitting part 540 may further include at least one of a first EBL **540*c* between the first HTL 540*b* and the first EML 550 and a first HBL 540*d* between the first EML 550 and the first ETL 540*e***.

The second emitting part 560 includes the second EML 570.

In addition, the second emitting part 560 may further include at least one of a second HTL **560*a* between the CGL 580 and the second EML 570, a second ETL 560*d* between the second EML 570 and the second electrode 164, and an EIL 560*e* between the second ETL 560*d* and the second electrode 530**.

Moreover, the second emitting part 560 may further include at least one of a second EBL **560*b* between the second HTL 560*a* and the second EML 570 and a second HBL 560*c* between the second EML 570 and the second ETL 560*d***.

The CGL 580 is positioned between the first and second emitting parts 540 and 560. Namely, the first and second emitting parts 540 and 560 are connected to each other through the CGL 580. The CGL 580 may be a P-N junction type CGL of an N-type CGL 582 and a P-type CGL 584.

The N-type CGL 582 is positioned between the first ETL **540*e* and the second HTL 560*a*, and the P-type CGL 584 is positioned between the N-type CGL 582 and the second HTL 560*a***.

The N-type CGL 582 provides an electron into the first EML 550 of the first emitting part 540, and the P-type CGL 584 provides a hole into the second EML 570 of the second emitting part 560.

Each of the first and second EMLs 550 and 570 is the green EML. At least one of the first and second EMLs 550 and 570 includes the first compound in Formulas 1 to 3. For example, the first EML 550 may include the first compound in Formulas 1 to 3.

The first EML 550 may further include a host. The host may be the second compound in Formulas 4-1, 4-2 and 5.

In addition, the first EML 550 may further include a delayed fluorescent compound. For example, the delayed fluorescent compound may be the third compound in Formulas 6-1, 6-2 and 7.

In the first EML 550, the weight ratio of the third compound may be greater than that of the first compound and smaller than that of the second compound. When the weight ratio of the third compound is greater than that of the first compound, the energy transfer from the third compound into the first compound is sufficiently generated. For example, in the first EML 550, the first compound may have a weight % of 0.1 to 10, preferably 0.1 to 5, and the third compound may have a weight % of 1 to 50, preferably 10 to 40, and more preferably 20 to 40. However, it is not limited thereto.

The second EML 570 may include the first compound of Formulas 1 to 3, the second compound of Formulas 4-1, 4-2 and 5 and the third compound of Formulas 6-1, 6-2 and 7. Alternatively, the second EML 570 may include a compound being different from at least one of the first compound and the third compound in the first EML 550 such that the first and second EMLs 550 and 570 have a different in an emitted-light wavelength or an emitting efficiency.

In the OLED D4 of the present disclosure, the singlet energy level of the third compound as the delayed fluorescent material is transferred into the first compound as the fluorescent dopant, and the emission is generated from the first compound. Accordingly, the emitting efficiency and the color purity of the OLED D4 are improved. In addition, since the first compound of Formulas 1 to 3 and the third compound of Formulas 4-1, 4-2 and 5 are included in the first EML 550, the emitting efficiency and the color purity of the OLED D4 are further improved.

Moreover, since the OLED D4 has a two-stack structure (double-stack structure) with two green EMLs, the color sense of the OLED D4 is improved and/or the emitting efficiency of the OLED D4 is optimized.

FIG. 8 is a schematic cross-sectional view of an organic light emitting display device according to a sixth embodiment of the present disclosure.

As shown in FIG. 8, the organic light emitting display device 1000 includes a substrate 1010, wherein first to third pixel regions P1, P2 and P3 are defined, a TFT Tr over the substrate 1010 and an OLED D5. The OLED D5 is disposed over the TFT Tr and is connected to the TFT Tr. For example, the first to third pixel regions P1, P2 and P3 may be a green pixel region, a red pixel region and a blue pixel region, respectively.

The substrate 1010 may be a glass substrate or a flexible substrate. For example, the flexible substrate may be a polyimide (PI) substrate, a polyethersulfone (PES) substrate, a polyethylenenaphthalate (PEN) substrate, a polyethylene terephthalate (PET) substrate or a polycarbonate (PC) substrate.

A buffer layer 1012 is formed on the substrate 1010, and the TFT Tr is formed on the buffer layer 1012. The buffer layer 1012 may be omitted.

As explained with FIG. 2, the TFT Tr may include a semiconductor layer, a gate electrode, a source electrode and a drain electrode and may serve as a driving element.

A planarization layer (or passivation layer) 1050 is formed on the TFT Tr. The planarization layer 1050 has a flat top surface and includes a drain contact hole 1052 exposing the drain electrode of the TFT Tr.

The OLED D5 is disposed on the planarization layer 1050 and includes a first electrode 1060, an emitting layer 1062 and a second electrode 1064. The first electrode 1060 is connected to the drain electrode of the TFT Tr, and the light emitting layer 1062 and the second electrode 1064 are sequentially stacked on the first electrode 1060. The OLED D5 is disposed in each of the first to third pixel regions P1 to P3 and emits different color light in the first to third pixel regions P1 to P3. For example, the OLED D5 in the first pixel region P1 may emit the green light, the OLED D5 in the second pixel region P2 may emit the red light, and the OLED D5 in the third pixel region P3 may emit the blue light.

The first electrode 1060 is formed to be separate in the first to third pixel regions P1 to P3, and the second electrode 1064 is formed as one-body to cover the first to third pixel regions P1 to P3.

The first electrode 1060 is one of an anode and a cathode, and the second electrode 1064 is the other one of the anode and the cathode. In addition, one of the first and second electrodes 1060 and 1064 may be a light transmitting electrode (or a semi-transmitting electrode), and the other one of the first and second electrodes 1060 and 1064 may be a reflecting electrode.

For example, the first electrode 1060 may be the anode and may include a transparent conductive oxide material layer formed of a transparent conductive oxide (TCO) material having a relatively high work function. The second electrode 1064 may be the cathode and may include a metallic material layer formed of a low resistance metallic material having a relatively low work function. For example, the transparent conductive oxide material layer of the first electrode 1060 include at least one of indium-tin-oxide (ITO), indium-zinc-oxide (IZO), indium-tin-zinc oxide (ITZO), tin oxide (SnO), zinc oxide (ZnO), indium-copper-oxide (ICO) and aluminum-zinc oxide alloy (Al:ZnO), and the second electrode 1064 may include Al, Mg, Ca, Ag, their alloy, e.g., Mg—Ag alloy, or their combination.

In the bottom-emission type organic light emitting display device 1000, the first electrode 1060 may have a single-layered structure of the transparent conductive oxide material layer.

On the other hand, in the top-emission type organic light emitting display device 1000, a reflection electrode or a reflection layer may be formed under the first electrode 1060. For example, the reflection electrode or the reflection layer may be formed of Ag or aluminum-palladium-copper (APC) alloy. In this instance, the first electrode 1060 may have a triple-layered structure of ITO/Ag/ITO or ITO/APC/ITO. In addition, the second electrode 1064 may have a thin profile (small thickness) to provide a light transmittance property (or a semi-transmittance property).

A bank layer 1066 is formed on the planarization layer 1050 to cover an edge of the first electrode 1060. Namely, the bank layer 1066 is positioned at a boundary of the first to third pixel regions P1 to P3 and exposes a center of the first electrode 1060 in the first to third pixel regions P1 to P3.

The light emitting layer 1062 as an emitting unit is formed on the first electrode 1060. The light emitting layer 1062 may have a single-layered structure of an EML. Alternatively, the light emitting layer 1062 may further include at least one of an HIL, an HTL, an EBL, which are sequentially stacked between the first electrode 1060 and the EML, an HBL, an ETL and an EIL, which are sequentially stacked between the EML and the second electrode 1064.

In the first pixel region P1 being the green pixel region, the EML of the light emitting layer 1062 includes the present disclosure in Formulas 1 to 3 as the first compound.

The EML of the light emitting layer 1062 in the first pixel region P1 may further include a host. The host may be the second compound in Formulas 4-1, 4-2 and 5.

In addition, the EML of the light emitting layer 1062 in the first pixel region P1 may further include a delayed fluorescent compound. For example, the delayed fluorescent compound may be the third compound in Formulas 6-1, 6-2 and 7.

An encapsulation film 1070 is formed on the second electrode 1064 to prevent penetration of moisture into the OLED D5. The encapsulation film 1070 may have a triple-layered structure including a first inorganic insulating layer, an organic insulating layer and a second inorganic insulating layer, but it is not limited thereto.

The organic light emitting display device 1000 may further include a polarization plate (not shown) for reducing an ambient light reflection. For example, the polarization plate may be a circular polarization plate. In the bottom-emission type organic light emitting display device 1000, the polarization plate may be disposed under the substrate 1010. In the top-emission type organic light emitting display device 1000, the polarization plate may be disposed on or over the encapsulation film 1070.

FIG. 9 is a schematic cross-sectional view of an OLED according to a seventh embodiment of the present disclosure.

Referring to FIG. 9 with FIG. 8, the OLED D5 is positioned in each of first to third pixel regions P1 to P3 and includes the first and second electrodes 1060 and 1064, which face each other, and the light emitting layer 1062 therebetween. The light emitting layer 1062 includes an EML 1090.

The first electrode 1060 may be an anode, and the second electrode 1064 may be a cathode. For example, the first electrode 1060 may be a reflective electrode, and the second electrode 1064 may be a transmitting electrode (or a semi-transmitting electrode).

The light emitting layer 1062 may further include an HTL 1082 between the first electrode 1060 and the EML 1090 and an ETL 1094 between the EML 1090 and the second electrode 1064.

In addition, the light emitting layer 1062 may further include an HIL 1080 between the first electrode 1060 and the HTL 1082 and an EIL 1096 between the ETL 1094 and the second electrode 1064.

Moreover, the light emitting layer 1062 may further include an EBL 1086 between the EML 1090 and the HTL 1082 and an HBL 1092 between the EML 1090 and the ETL 1094.

Furthermore, the light emitting layer 1062 may further include an auxiliary HTL 1084 between the HTL 1082 and the EBL 1086. The auxiliary HTL 1084 may include a first auxiliary HTL 1084*a* in the first pixel region P1, a second auxiliary HTL 1084*b* in the second pixel region P2 and a third auxiliary HTL 1084*c* in the third pixel region P3.

The first auxiliary HTL 1084*a* has a first thickness, the second auxiliary HTL 1084*b* has a second thickness, and the third auxiliary HTL 1084*c* has a third thickness. The first thickness is smaller than the second thickness and greater than the third thickness such that the OLED D5 provides a micro-cavity structure.

Namely, by the first to third auxiliary HTLs 1084*a*, 1084*b* and 1084*c* having a difference in a thickness, a distance between the first and second electrodes 1060 and 1064 in the first pixel region P1, in which a first wavelength range light, e.g., green light, is emitted, is smaller than a distance between the first and second electrodes 1060 and 1064 in the second pixel region P2, in which a second wavelength range light, e.g., red light, being greater than the first wavelength range is emitted, and is greater than a distance between the first and second electrodes 1060 and 1064 in the third pixel region P3, in which a third wavelength range light, e.g., blue light, being smaller than the first wavelength range is emitted. Accordingly, the emitting efficiency of the OLED D5 is improved.

In FIG. 9, the third auxiliary HTL 1084*c* is formed in the third pixel region P3. Alternatively, a micro-cavity structure may be provided without the third auxiliary HTL 1084*c*.

A capping layer (not shown) for improving a light-extracting property may be further formed on the second electrode 1084.

The EML 1090 includes a first EML 1090*a* in the first pixel region P1, a second EML 1090*b* in the second pixel region P2 and a third EML 1090*c* in the third pixel region P3. The first to third EMLs 1090*a*, 1090*b* and 1090*c* may be a green EML, a red EML and a blue EML, respectively.

The first EML 1090*a* in the first pixel region P1 includes the organic compound of the present disclosure in Formulas 1 to 3 as the first compound. In addition, the first EML 1090*a* in the first pixel region P1 may further include a host. The host may be the second compound in Formulas 4-1, 4-2 and 5. Moreover, the first EML 1090*a* in the first pixel region P1 may further include a delayed fluorescent compound. For example, the delayed fluorescent compound may be the third compound in Formulas 6-1, 6-2 and 7.

In the first EML 1090*a* in the first pixel region P1, the weight ratio of the third compound may be greater than that of the first compound and smaller than that of the second compound. When the weight ratio of the third compound is greater than that of the first compound, the energy transfer from the third compound into the first compound is sufficiently generated. For example, in the first EML 1090*a* in the first pixel region P1, the first compound may have a weight % of 0.1 to 10, the second compound may have a weight % of 50 to 80, and the third compound may have a weight % of 1 to 50. However, it is not limited thereto.

Each of the second EML 1090*b* in the second pixel region P2 and the third EML 1090*c* in the third pixel region P3 may include a host and a dopant. For example, in each of the second EML 1090*b* in the second pixel region P2 and the third EML 1090*c* in the third pixel region P3, the dopant may include at least one of a phosphorescent compound, a fluorescent compound and a delayed fluorescent compound.

The OLED D5 in FIG. 9 respectively emits the green light, the red light and the blue light in the first to third pixel regions P1 to P3 such that the organic light emitting display device 1000 (of FIG. 8) can provide a full-color image.

The organic light emitting display device 1000 may further include a color filter layer corresponding to the first to third pixel regions P1 to P3 to improve the color purity. For example, the color filter layer may include a first color filter layer, e.g., a green color filter layer, corresponding to the first pixel region P1, a second color filter layer, e.g., a red color filter layer, corresponding to the second pixel region P2, and a third color filter layer, e.g., a blue color filter layer, corresponding to the third pixel region P3.

In the bottom-emission type organic light emitting display device 1000, the color filter layer may be disposed between the OLED D5 and the substrate 1010. On the other hand, in the top-emission type organic light emitting display device 1000, the color filter layer may be disposed on or over the OLED D5.

FIG. 10 is a schematic cross-sectional view of an organic light emitting display device according to an eighth embodiment of the present disclosure.

As shown in FIG. 10, the organic light emitting display device 1100 includes a substrate 1110, wherein first to third pixel regions P1, P2 and P3 are defined, a TFT Tr over the substrate 1110, an OLED D, which is disposed over the TFT Tr and is connected to the TFT Tr, and a color filter layer 1120 corresponding to the first to third pixel regions P1 to P3. For example, the first to third pixel regions P1, P2 and P3 may be a green pixel region, a red pixel region and a blue pixel region, respectively.

The substrate 1110 may be a glass substrate or a flexible substrate. For example, the flexible substrate may be a polyimide (PI) substrate, a polyethersulfone (PES) substrate, a polyethylenenaphthalate (PEN) substrate, a polyethylene terephthalate (PET) substrate or a polycarbonate (PC) substrate.

The TFT Tr is formed on the substrate 1110. Alternatively, a buffer layer (not shown) may be formed on the substrate 1110, and the TFT Tr may be formed on the buffer layer.

As explained with FIG. 2, the TFT Tr may include a semiconductor layer, a gate electrode, a source electrode and a drain electrode and may serve as a driving element.

In addition, the color filter layer 1120 is disposed on the substrate 1110. For example, the color filter layer 1120 may include a first color filter layer 1122 corresponding to the first pixel region P1, a second color filter layer 1124 corresponding to the second pixel region P2, and a third color filter layer 1126 corresponding to the third pixel region P3. The first to third color filter layers 1122, 1124 and 1126 may be a green color filter layer, a red color filter layer and a blue color filter layer, respectively. For example, the first color filter layer 1122 may include at least one of a green dye and a green pigment, and the second color filter layer 1124 may include at least one of a red dye and a red pigment. The third color filter layer 1126 may include at least one of a blue dye and a blue pigment.

A planarization layer (or passivation layer) 1150 is formed on the TFT Tr and the color filter layer 1120. The planarization layer 1150 has a flat top surface and includes a drain contact hole 1152 exposing the drain electrode of the TFT Tr.

The OLED D is disposed on the planarization layer 1150 and corresponds to the color filter layer 1120. The OLED D includes a first electrode 1160, an emitting layer 1162 and a second electrode 1164. The first electrode 1160 is connected to the drain electrode of the TFT Tr, and the light emitting layer 1162 and the second electrode 1164 are sequentially stacked on the first electrode 1160. The OLED D emits the white light in each of the first to third pixel regions P1 to P3.

The first electrode 1160 is formed to be separate in the first to third pixel regions P1 to P3, and the second electrode 1164 is formed as one-body to cover the first to third pixel regions P1 to P3.

The first electrode 1160 is one of an anode and a cathode, and the second electrode 1164 is the other one of the anode and the cathode. In addition, the first electrode 1160 may be a light transmitting electrode (or a semi-transmitting electrode), and the second electrode 1164 may be a reflecting electrode.

For example, the first electrode 1160 may be the anode and may include a transparent conductive oxide material layer formed of a transparent conductive oxide (TCO) material having a relatively high work function. The second electrode 1164 may be the cathode and may include a metallic material layer formed of a low resistance metallic material having a relatively low work function. For example, the transparent conductive oxide material layer of the first electrode 1160 include at least one of indium-tin-oxide (ITO), indium-zinc-oxide (IZO), indium-tin-zinc oxide (ITZO), tin oxide (SnO), zinc oxide (ZnO), indium-copper-oxide (ICO) and aluminum-zinc oxide alloy (Al:ZnO), and the second electrode 1164 may include Al, Mg, Ca, Ag, their alloy, e.g., Mg—Ag alloy, or their combination.

The light emitting layer 1162 as an emitting unit is formed on the first electrode 1160. The light emitting layer 1162 includes at least two emitting parts emitting different color light.

Each emitting part may have a single-layered structure of an EML. Alternatively, each emitting part may further include at least one of an HIL, an HTL, an EBL, an HBL, an ETL and an EIL. In addition, the light emitting layer 1162 may further include a charge generation layer (CGL) between the emitting parts.

The EML of one of the emitting parts includes the organic compound of the present disclosure in Formulas 1 to 3 as the first compound. The EML of one of the emitting parts may further include a host. The host may be the second compound in Formulas 4-1, 4-2 and 5. In addition, the EML of one of the emitting parts may further include a delayed fluorescent compound.

For example, the delayed fluorescent compound may be the third compound in Formulas 6-1, 6-2 and 7.

A bank layer 1166 is formed on the planarization layer 1150 to cover an edge of the first electrode 1160. Namely, the bank layer 1166 is positioned at a boundary of the first to third pixel regions P1 to P3 and exposes a center of the first electrode 1160 in the first to third pixel regions P1 to P3. As mentioned above, since the OLED D emits the white light in the first to third pixel regions P1 to P3, the light emitting layer 1162 may be formed as a common layer in the first to third pixel regions P1 to P3 without separation in the first to third pixel regions P1 to P3. The bank layer 1166 may be formed to prevent the current leakage at an edge of the first electrode 1160 and may be omitted.

Although not shown, the organic light emitting display device 1100 may further include an encapsulation film is formed on the second electrode 1164 to prevent penetration of moisture into the OLED D. In addition, the organic light emitting display device 1100 may further include a polarization plate under the substrate 1110 for reducing an ambient light reflection.

In the organic light emitting display device 1100 of FIG. 11, the first electrode 1160 is a transparent electrode (light transmitting electrode), and the second electrode 1164 is a reflecting electrode. In addition, the color filter layer 1120 is positioned between the substrate 1110 and the OLED D. Namely, the organic light emitting display device 11000 is a botto-emission type.

Alternatively, in the organic light emitting display device 1100, the first electrode 1160 may be a reflecting electrode, and the second electrode 1154 may be a transparent electrode (or a semi-transparent electrode). In this case, the color filter layer 1120 is positioned on or over the OLED D.

In the organic light emitting display device 1100, the OLED D in the first to third pixel regions P1 to P3 emits the white light, and the white light passes through the first to third color filter layers 1122, 1124 and 1126. Accordingly, the green light, the red light and the blue light are displayed in the first to third pixel regions P1 to P3, respectively.

Although not shown, a color conversion layer may be formed between the OLED D and the color filter layer 1120. The color conversion layer may include a green color conversion layer, a red color conversion layer and a blue color conversion layer respectively corresponding to the first to third pixel regions P1 to P3, and the white light from the OLED D can be converted into the green light, the red light and the blue light. The color conversion layer may include a quantum dot. Accordingly, the color purity of the OLED D may be further improved.

The color conversion layer may be included instead of the color filter layer 1120.

FIG. 11 is a schematic cross-sectional view of an OLED according to a ninth embodiment of the present disclosure.

As shown in FIG. 11, the OLED D6 includes the first and second electrodes 1160 and 1164, which face each other, and the light emitting layer 1162 therebetween.

The first electrode 1160 may be an anode, and the second electrode 1164 may be a cathode. The first electrode 1160 is a transparent electrode (a light transmitting electrode), and the second electrode 1164 is a reflecting electrode.

The light emitting layer 1162 includes a first emitting part 1210 including a first EML 1220, a second emitting part 1230 including a second EML 1240 and a third emitting part 1250 including a third EML 1260. In addition, the light emitting layer 1162 may further include a first CGL 1270 between the first and second emitting parts 1210 and 1230 and a second CGL 1280 between the first emitting part 1210 and the third emitting part 1250.

The first CGL 1270 is positioned between the first and second emitting parts 1210 and 1230, and the second CGL 1280 is positioned between the first and third emitting parts 1210 and 1250. Namely, the third emitting part 1250, the second CGL 1280, the first emitting part 1210, the first CGL 1270 and the second emitting part 1230 are sequentially stacked on the first electrode 1160. In other words, the first emitting part 1210 is positioned between the first and second CGLs 1270 and 1280, and the second emitting part 1230 is positioned between the first CGL 1270 and the second electrode 1164. The third emitting part 1250 is positioned between the second CGL 1280 and the first electrode 1160.

The first emitting part 1210 may further include a first HTL **1210*a* under the first EML 1220 and a first ETL 1210*b* over the first EML 1220. Namely, the first HTL 1210*a* may positioned between the first EML 1220 and the second CGL 1270, and the first ETL 1210*b* may be positioned between the first EML 1220 and the first CGL 1270**.

In addition, the first emitting part 1210 may further include an EBL (not shown) between the first HTL **1210*a* and the first EML 1220 and an HBL (not shown) between the first ETL 1210*b* and the first EML 1220**.

The second emitting part 1230 may further include a second HTL **1230*a* under the second EML 1240, a second ETL 1230*b* over the second EML 1240 and an EIL 1230*c* on the second ETL 1230*b*. Namely, the second HTL 1230*a* may be positioned between the second EML 1240 and the first CGL 1270, and the second ETL 1230*b* and the EIL 1230*c* may be positioned between the second EML 1240 and the second electrode 1164**.

In addition, the second emitting part 1230 may further include an EBL (not shown) between the second HTL **1230*a* and the second EML 1240 and an HBL (not shown) between the second ETL 1230*b* and the second EML 1240**.

The third emitting part 1250 may further include a third HTL **1250*b* under the third EML 1260, an HIL 1250*a* under the third HTL 1250*b* and a third ETL 1250*c* over the third EML 1260. Namely, the HIL 1250*a* and the third HTL 1250*b* may be positioned between the first electrode 1160 and the third EML 1260, and the third ETL 1250*c* may be positioned between the third EML 1260 and the second CGL 1280**.

In addition, the third emitting part 1250 may further include an EBL (not shown) between the third HTL **1250*b* and the third EML 1260 and an HBL (not shown) between the third ETL 1250*c* and the third EML 1260**.

One of the first to third EMLs 1220, 1240 and 1260 is a green EML. Another one of the first to third EMLs 1220, 1240 and 1260 may be a blue EML, and the other one of the first to third EMLs 1220, 1240 and 1260 may be a red EML.

For example, the first EML 1220 may be the green EML, the second EML 1240 may be the blue EML, and the third EML 1260 may be the red EML. Alternatively, the first EML 1220 may be the green EML, the second EML 1240 may be the red EML, and the third EML 1260 may be the blue EML.

The first EML 1220 includes the organic compound of the present disclosure in Formulas 1 to 3 as the first compound. In addition, the first EML 1220 may further include a host. The host may be the second compound in Formulas 4-1, 4-2 and 5. Moreover, the first EML 1220 may further include a delayed fluorescent compound. For example, the delayed fluorescent compound may be the third compound in Formulas 6-1, 6-2 and 7.

the first compound being the delayed fluorescent compound and the second compound being the fluorescent compound. The first EML 1220 may further include a third compound being a host. The first compound is represented by Formula 1, and the second compound is represented by Formula 3.

In the first EML 1220, the weight ratio of the third compound may be greater than that of the first compound and smaller than that of the second compound. When the weight ratio of the third compound is greater than that of the first compound, the energy transfer from the third compound into the first compound is sufficiently generated. For example, in the first EML 1220, the first compound may have a weight % of 0.1 to 5, the second compound may have a weight % of 60 to 75, and the third compound may have a weight % of 20 to 40. However, it is not limited thereto.

The second EML 1240 includes a host and a blue dopant (or a red dopant), and the third EML 1260 includes a host and a red dopant (or a blue dopant). For example, in each of the second and third EMLs 1240*a* and 1260, the dopant may include at least one of a phosphorescent compound, a fluorescent compound and a delayed fluorescent compound.

The OLED D6 in the first to third pixel regions P1 to P3 (of FIG. 11) emits the white light, and the white light passes through the color filter layer 1120 (of FIG. 11) in the first to third pixel regions P1 to P3. Accordingly, the organic light emitting display device 1100 (of FIG. 11) can provide a full-color image.

FIG. 12 is a schematic cross-sectional view of an OLED according to a tenth embodiment of the present disclosure.

As shown in FIG. 12, the OLED D7 includes the first and second electrodes 1360 and 1364, which face each other, and the light emitting layer 1362 therebetween.

The first electrode 1360 may be an anode, and the second electrode 1364 may be a cathode. The first electrode 1360 is a transparent electrode (a light transmitting electrode), and the second electrode 1364 is a reflecting electrode.

The light emitting layer 1362 includes a first emitting part 1410 including a first EML 1420, a second emitting part 1430 including a second EML 1440 and a third emitting part 1450 including a third EML 1460. In addition, the light emitting layer 1362 may further include a first CGL 1470 between the first and second emitting parts 1410 and 1430 and a second CGL 1480 between the first emitting part 1410 and the third emitting part 1450.

The first emitting part 1420 includes a lower EML 1420*a* and an upper EML 1420*b*. Namely, the lower EML 1420*a* is positioned to be closer to the first electrode 1360, and the upper EML 1420*b* is positioned to be closer to the second electrode 1364.

The first CGL 1470 is positioned between the first and second emitting parts 1410 and 1430, and the second CGL 1480 is positioned between the first and third emitting parts 1410 and 1450. Namely, the third emitting part 1450, the second CGL 1480, the first emitting part 1410, the first CGL 1470 and the second emitting part 1430 are sequentially stacked on the first electrode 1360. In other words, the first emitting part 1410 is positioned between the first and second CGLs 1470 and 1480, and the second emitting part 1430 is positioned between the first CGL 1470 and the second electrode 1364. The third emitting part 1450 is positioned between the second CGL 1480 and the first electrode 1360.

The first emitting part 1410 may further include a first HTL 1410*a* under the first EML 1420 and a first ETL 1410*b* over the first EML 1420. Namely, the first HTL 1410*a* may positioned between the first EML 1420 and the second CGL 1470, and the first ETL 1410*b* may be positioned between the first EML 1420 and the first CGL 1470.

In addition, the first emitting part 1410 may further include an EBL (not shown) between the first HTL 1410*a* and the first EML 1420 and an HBL (not shown) between the first ETL 1410*b* and the first EML 1420.

The second emitting part 1430 may further include a second HTL 1430*a* under the second EML 1440, a second ETL 1430*b* over the second EML 1440 and an EIL 1430*c* on the second ETL 1430*b*. Namely, the second HTL 1430*a* may be positioned between the second EML 1440 and the first CGL 1470, and the second ETL 1430*b* and the EIL 1430*c* may be positioned between the second EML 1440 and the second electrode 1364.

In addition, the second emitting part 1430 may further include an EBL (not shown) between the second HTL 1430*a* and the second EML 1440 and an HBL (not shown) between the second ETL 1430*b* and the second EML 1440.

The third emitting part 1450 may further include a third HTL 1450*b* under the third EML 1460, an HIL 1450*a* under the third HTL 1450*b* and a third ETL 1450*c* over the third EML 1460. Namely, the HIL 1450*a* and the third HTL 1450*b* may be positioned between the first electrode 1360 and the third EML 1460, and the third ETL 1450*c* may be positioned between the third EML 1460 and the second CGL 1480.

In addition, the third emitting part 1450 may further include an EBL (not shown) between the third HTL 1450*b* and the third EML 1460 and an HBL (not shown) between the third ETL 1450*c* and the third EML 1460.

One of the lower and upper EMLs 1420*a* and 1420*b* of the first EML 1420 is a green EML, and the other one of the lower and upper EMLs 1420*a* and 1420*b* of the first EML 1420 may be a red EML. Namely, the green EML (or the red EML) and the red EML (or the green EML) are sequentially stacked to form the first EML 1420.

For example, the upper EML 1420*b* being the green EML includes the organic compound of the present disclosure in Formulas 1 to 3 as the first compound. In addition, the upper EML 1420*b* may further include a host. The host may be the second compound in Formulas 4-1, 4-2 and 5. Moreover, the upper EML 1420*b* may further include a delayed fluorescent compound. For example, the delayed fluorescent compound may be the third compound in Formulas 6-1, 6-2 and 7.

In the upper EML 1420*b*, the weight ratio of the third compound may be greater than that of the first compound and smaller than that of the second compound. When the weight ratio of the third compound is greater than that of the first compound, the energy transfer from the third compound into the first compound is sufficiently generated. For example, in the upper EML 1420*b*, the first compound may have a weight % of 0.1 to 5, the second compound may have a weight % of 60 to 75, and the third compound may have a weight % of 20 to 40. However, it is not limited thereto.

The lower EML 1420*a* being the red EML may include a host and a red dopant.

Each of the second and third EMLs 1440 and 1460 may be a blue EML. Each of the second and third EMLs 1440 and 1460 may include a host and a blue dopant. The host and the dopant of the second EML 1440 may be same as the host and the dopant of the third EML 1460.

Alternatively, the host and the dopant of the second EML 1440 may be different from the host and the dopant of the third EML 1460. For example, the dopant in the second EML 1440 may have a difference in the emitting efficiency and/or the emitting light wavelength from the dopant in the third EML 1460.

In each of the lower EML 1420*a*, the second EML 1440 and the third EML 1460, the dopant may include at least one of a phosphorescent compound, a fluorescent compound and a delayed fluorescent compound.

The OLED D7 in the first to third pixel regions P1 to P3 (of FIG. 10) emits the white light, and the white light passes through the color filter layer 1120 (of FIG. 10) in the first to third pixel regions P1 to P3. Accordingly, the organic light emitting display device 1100 (of FIG. 10) can provide a full-color image.

In FIG. 12, the OLED D7 has a three-stack (triple-stack) structure including the second and third EMLs 1440 and

1460 being the blue EML with the first EML 1420. Alternatively, one of the second and third EMLs 1440 and 1460 may be omitted such that the OLED D7 may have a two-stack (double-stack) structure.

As shown in FIGS. 7, 11 and 12, the OLED in each pixel region includes a first EML, e.g., a green EML, including the organic compound of the present disclosure, one or more second EML and a CGL so that the OLED has a tandem structure. In this instance, one or more second EML is at least one of a red EML, a green EML and a blue EML so that the OLED provides the green emission or the white emission.

While the present disclosure has been described with reference to exemplary embodiments and examples, these embodiments and examples are not intended to limit the scope of the present disclosure. Rather, it will be apparent to those skilled in the art that various modifications and variations can be made in the present disclosure without departing from the spirit or scope of the invention. Thus, it is intended that the present disclosure cover the modifications and variations of the present disclosure provided they come within the scope of the appended claims and their equivalents.

The various embodiments described above can be combined to provide further embodiments. All of patents, patent application publications, patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An organic compound being one of compounds in Formula 3:

[Formula 3]

compound 1

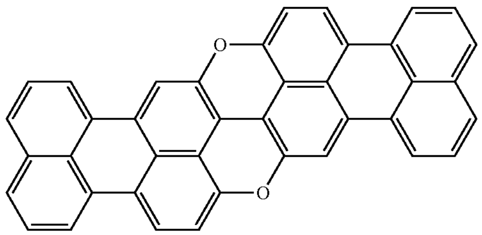

compound 2

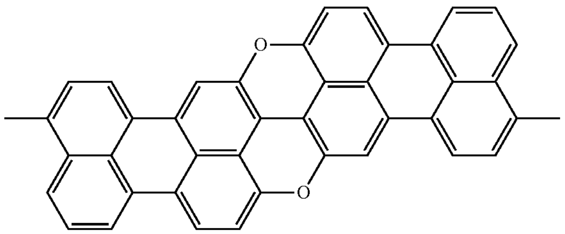

-continued compound 3

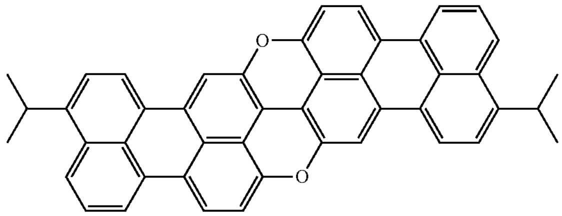

compound 4

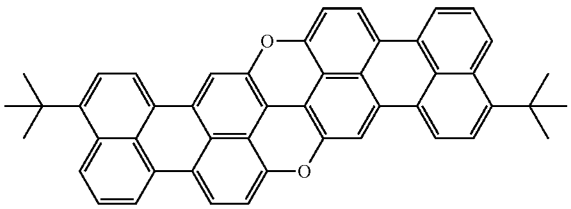

compound 5

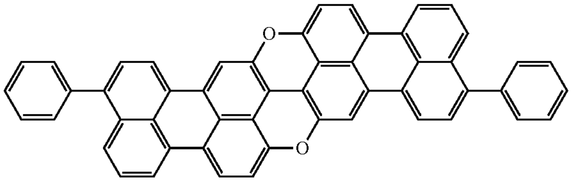

compound 6

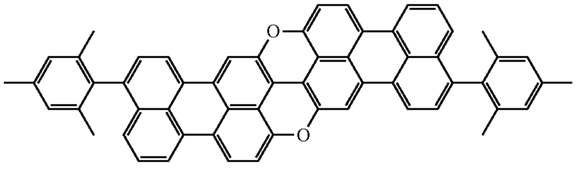

compound 7

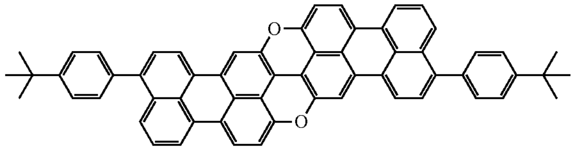

compound 8

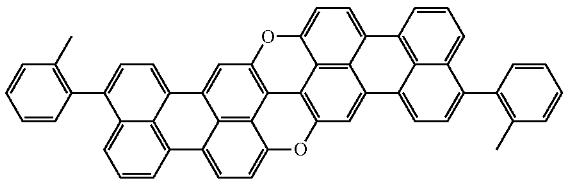

compound 9

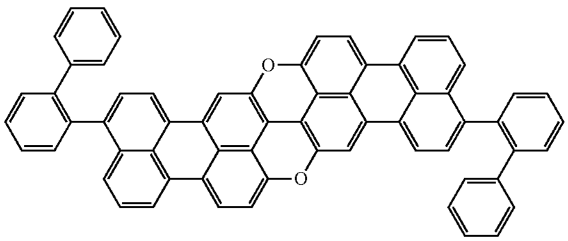

-continued
compound 10
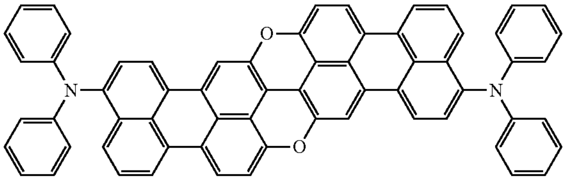
compound 11
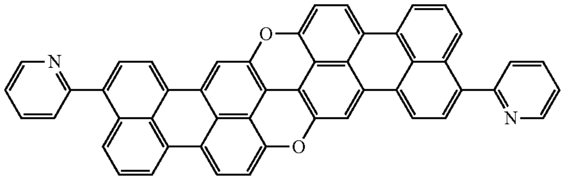
compound 12
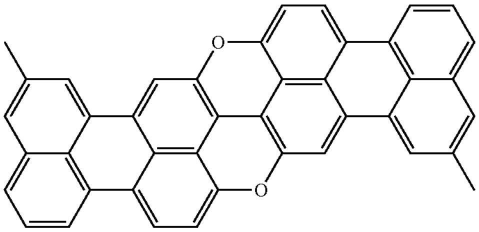
compound 13
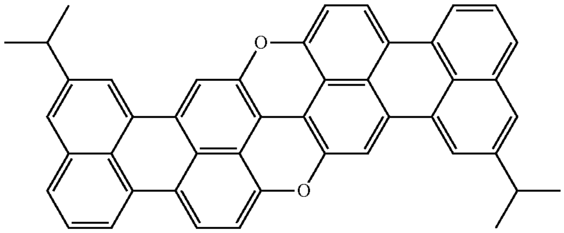
compound 14
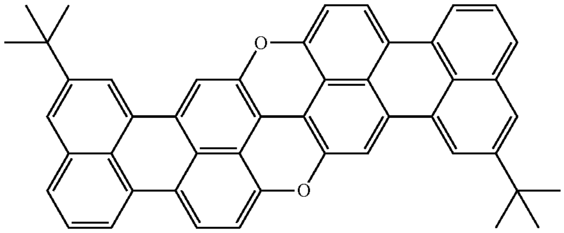
compound 15
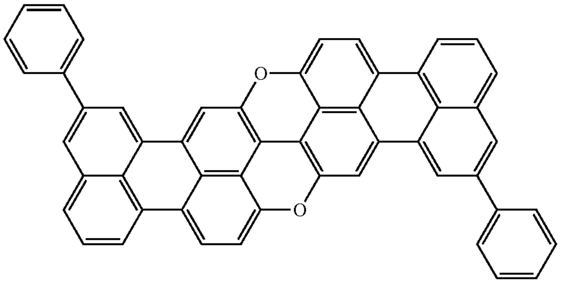
-continued
compound 16
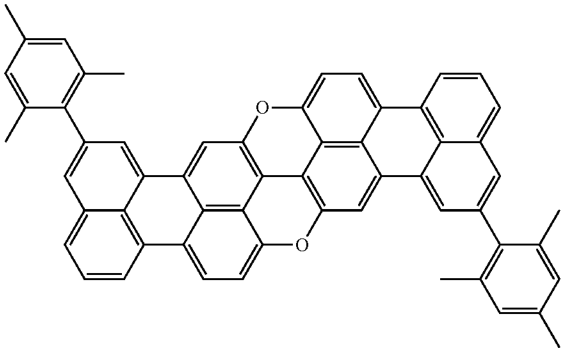
compound 17
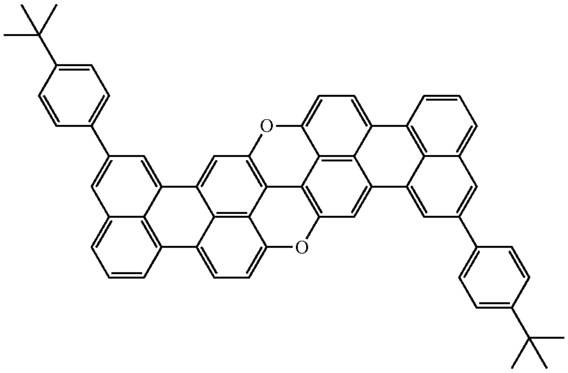
compound 18
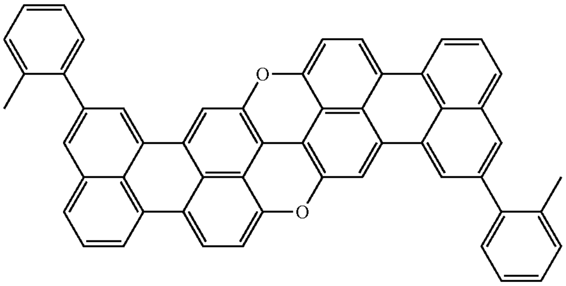
compound 19
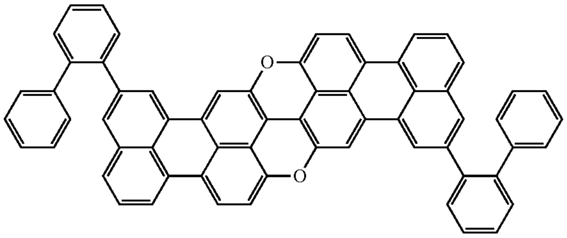

-continued compound 20

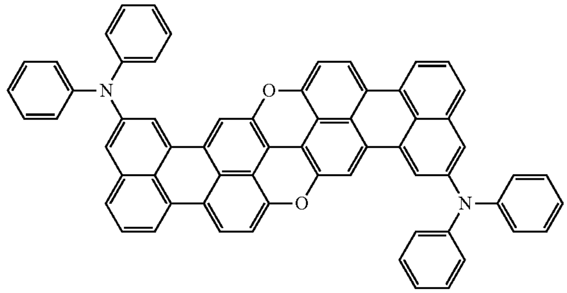

compound 21

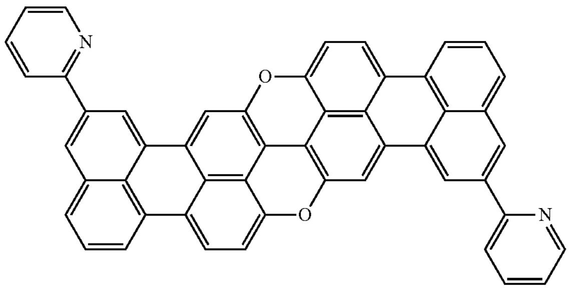

compound 22

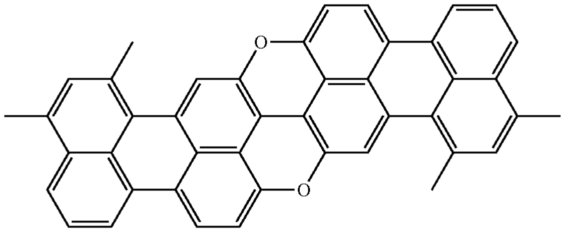

compound 23

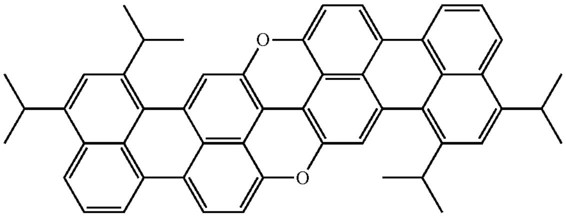

compound 24

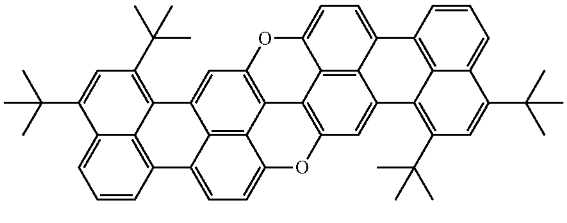

-continued compound 25

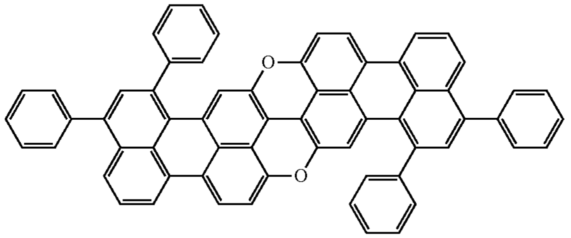

compound 26

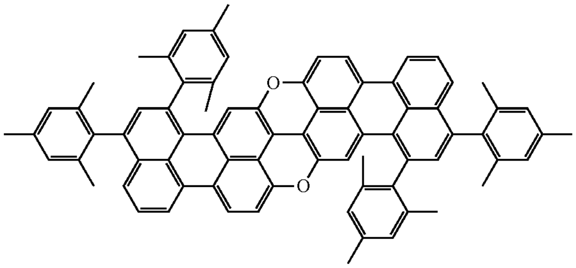

compound 27

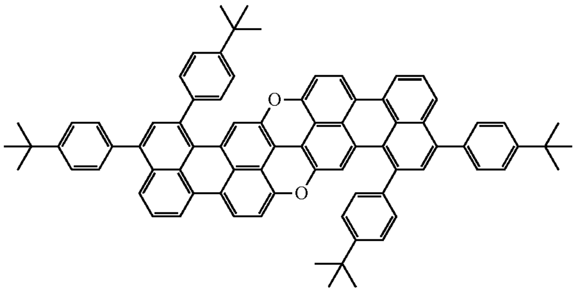

compound 28

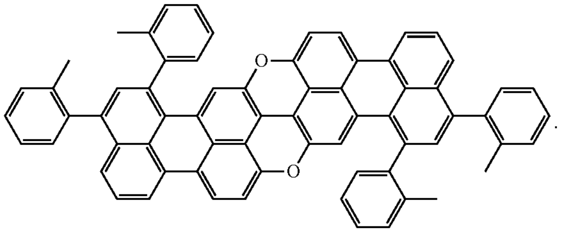

2. An organic light emitting diode, comprising:

a first electrode;

a second electrode facing the first electrode; and a first emitting material layer positioned between the first and second electrodes, wherein the first emitting material layer includes a first compound being one of compounds in Formula 3:

[Formula 3]
compound 1
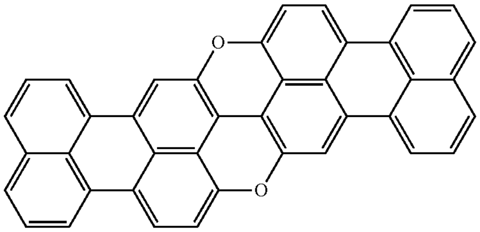
compound 2
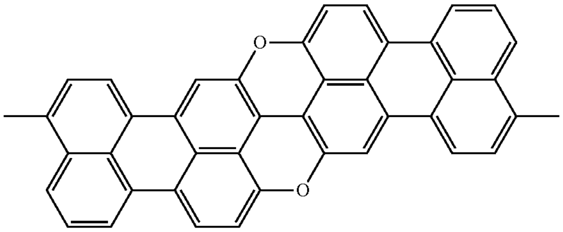
compound 3
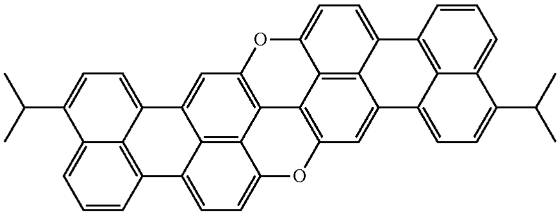
compound 4
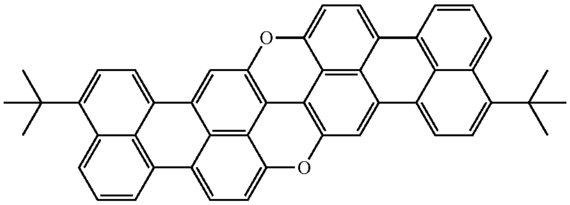
compound 5
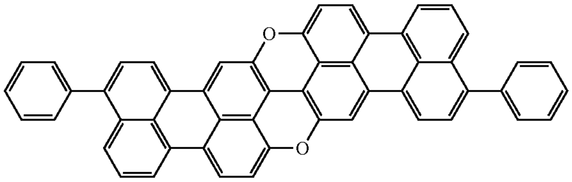
compound 6
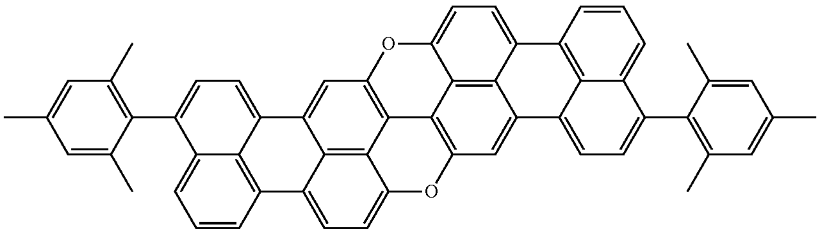
compound 7
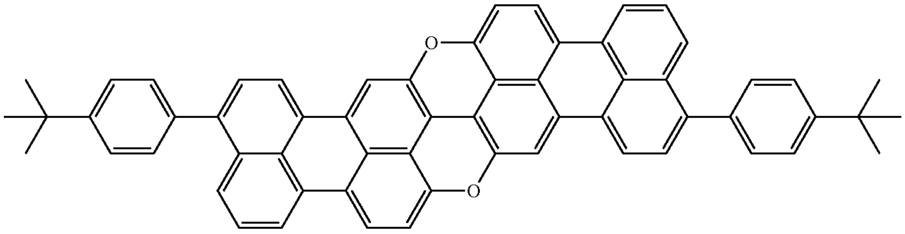
compound 8
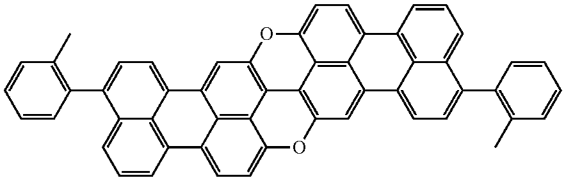
compound 9
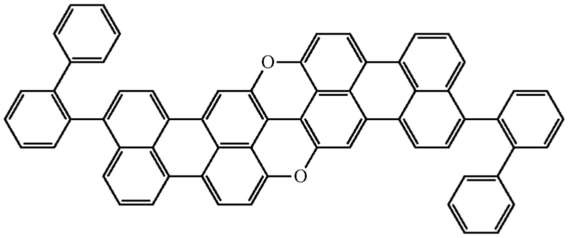

-continued
compound 10
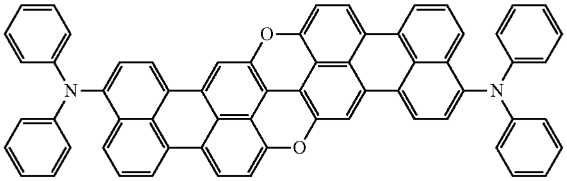
compound 11
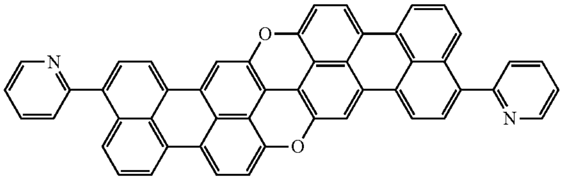
compound 12
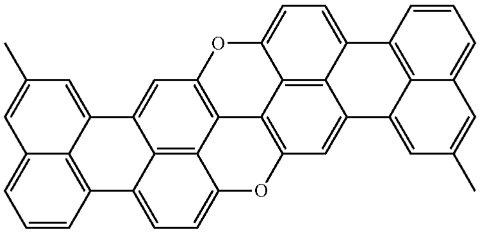
compound 13
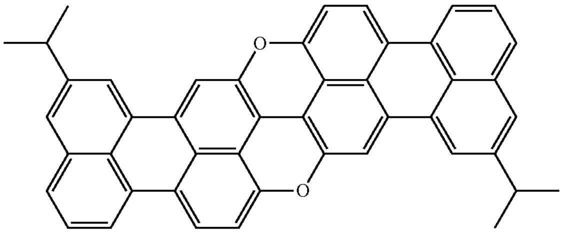
compound 14
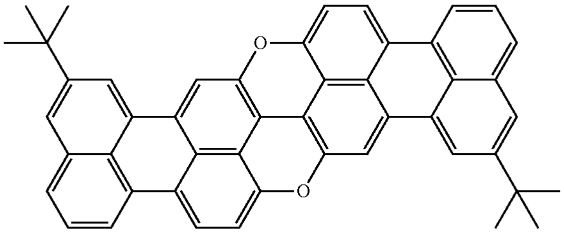
compound 15
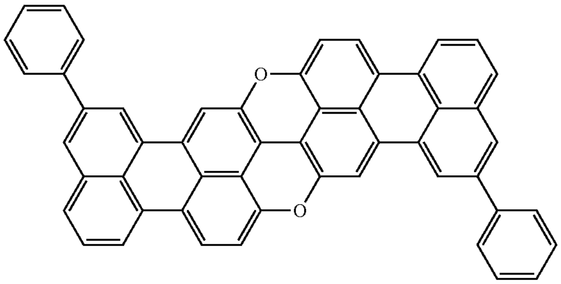
compound 16
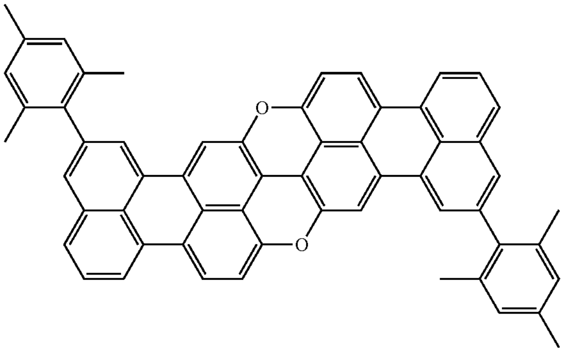
compound 17
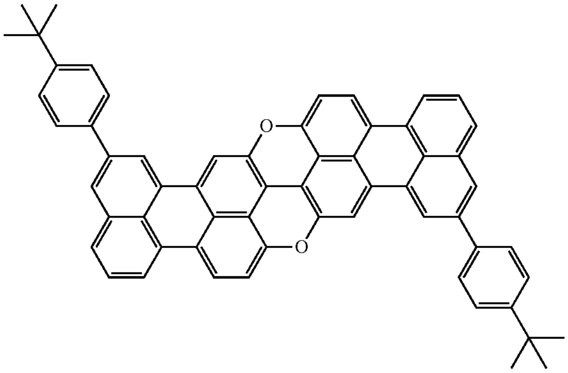
compound 18
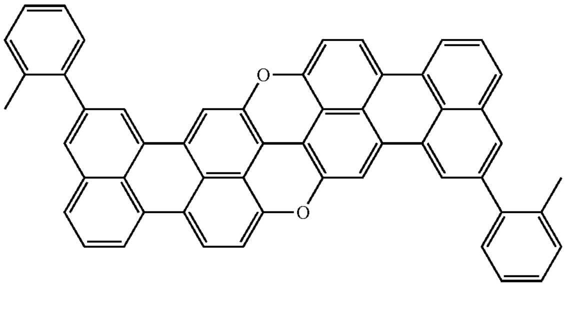
compound 19
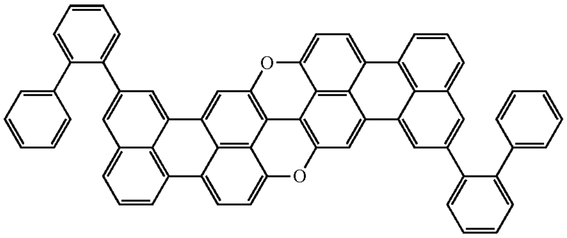

-continued
compound 20
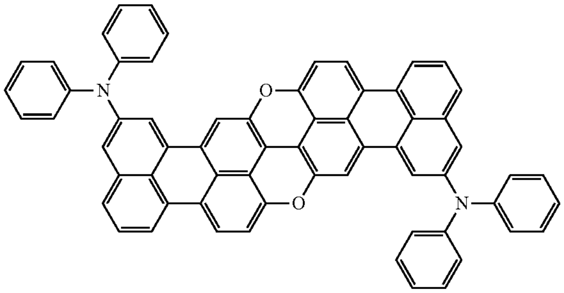
compound 21
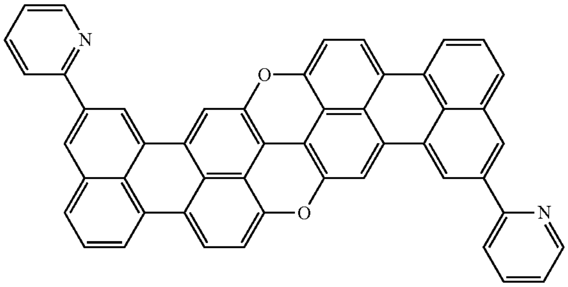
compound 22
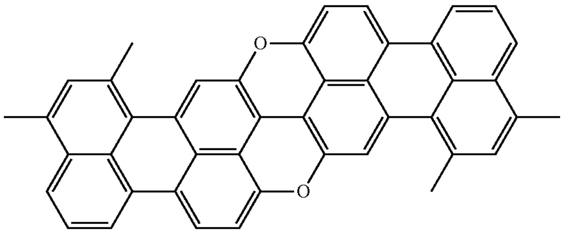
compound 23
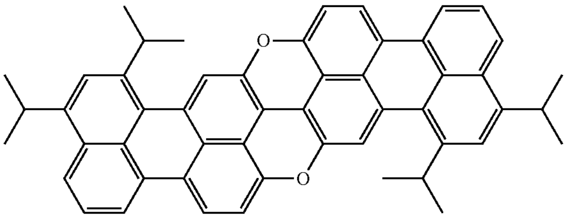
compound 24
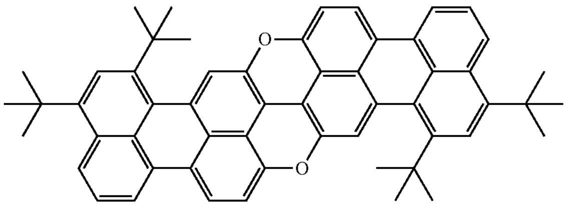
compound 25
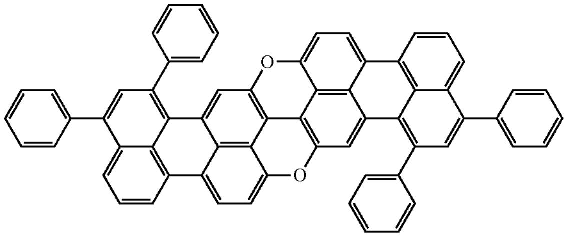
compound 26
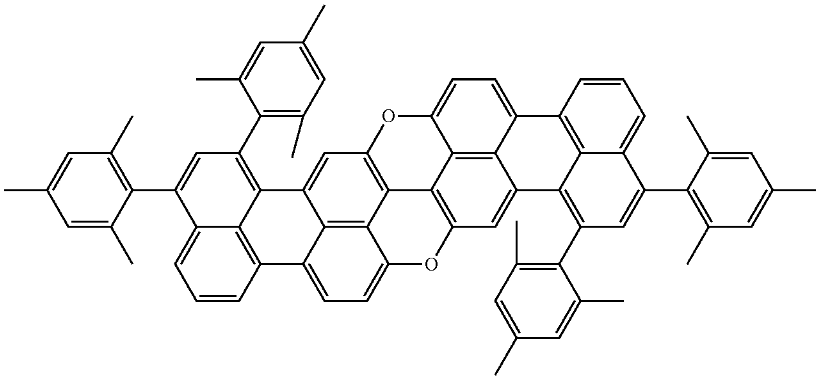

-continued compound 27

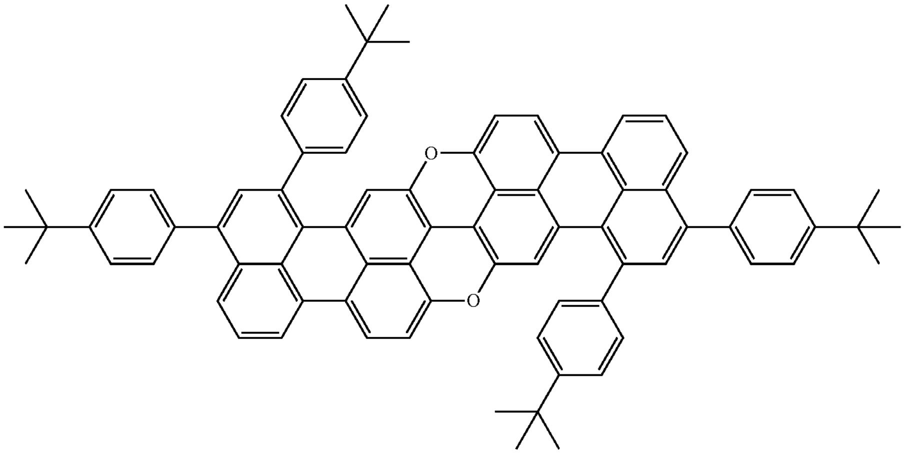

compound 28

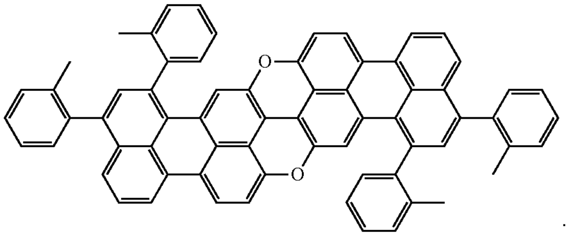

.

3. The organic light emitting diode according to claim 2, wherein the first emitting material layer further includes a second compound as a host, wherein the second compound is represented by Formula 4-1 or Formula 4-2:

[Formula 4-1]

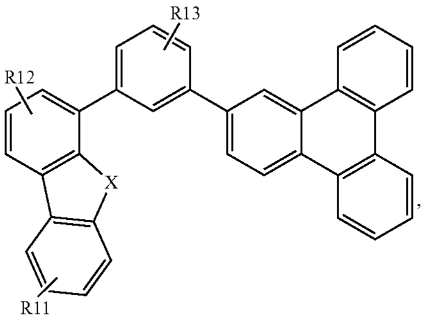

, and

[Formula 4-2]

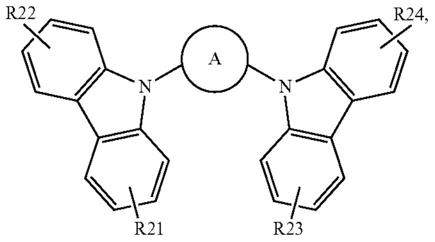

wherein in Formula 4-1, X is oxygen or sulfur, and each of R11 to R13 is independently selected from the group consisting of hydrogen, deuterium, halogen, cyano, silyl, C1 to C20 alkyl group, C6 to C30 aryl group, C5 to C30 heteroaryl group and C1 to C20 amine, and wherein in Formula 4-2, A is selected from the group consisting of C6 to C30 arylene group and C5 to C30 heteroarylene group, and each of R21 to R24 is independently selected from the group consisting of hydrogen, deuterium, halogen, cyano, silyl, C1 to C20 alkyl group, C6 to C30 aryl group, C5 to C30 heteroaryl group and C1 to C20 amine.

4. The organic light emitting diode according to claim 3, wherein the second compound is one of compounds in Formula 5:

[Formula 5]

H1

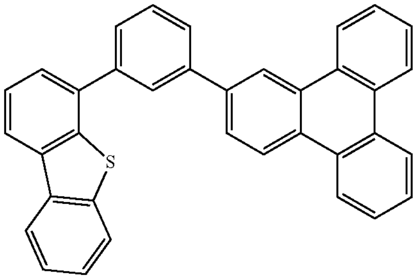

-continued

H2

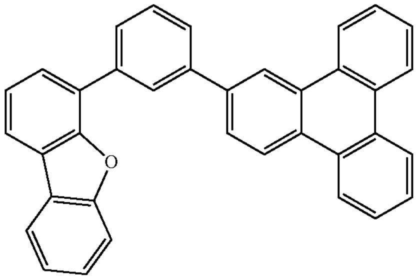

H3

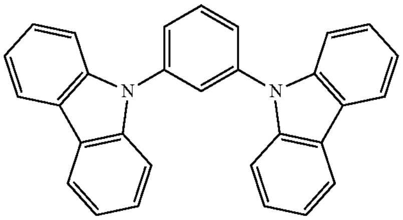

H4

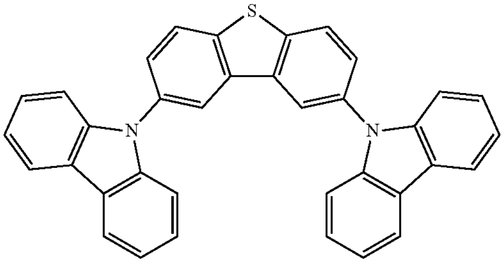

H5

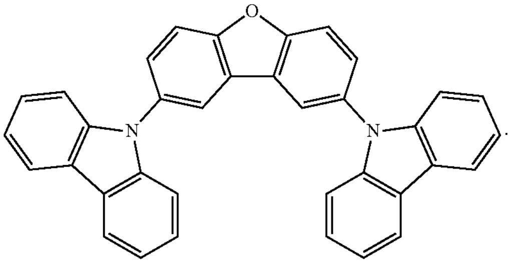

5. The organic light emitting diode according to claim 2, wherein the first emitting material layer further includes a third compound being a delayed fluorescent compound.

6. The organic light emitting diode according to claim 5, wherein the third compound is represented by Formula 6:

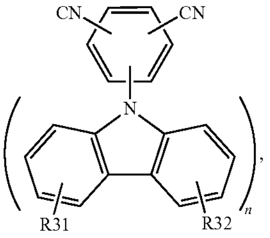

wherein in Formula 6, n is an integer of 1 to 4, and wherein each of R31 and R32 is independently selected from the group consisting of hydrogen, deuterium, tritium, a C1 to C20 alkyl group, a C6 to C30 aryl group and a C3 to C40 heteroaryl group.

7. The organic light emitting diode according to claim 5, wherein the third compound is one of compounds in Formula 7:

[Formula 7]

1-1

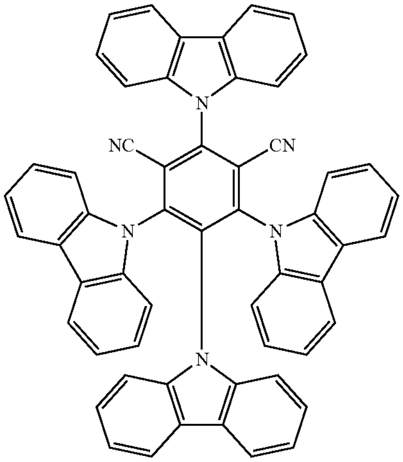

1-2

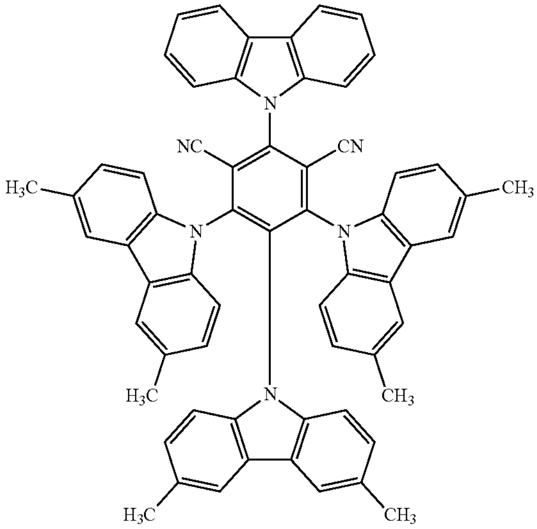

1-3

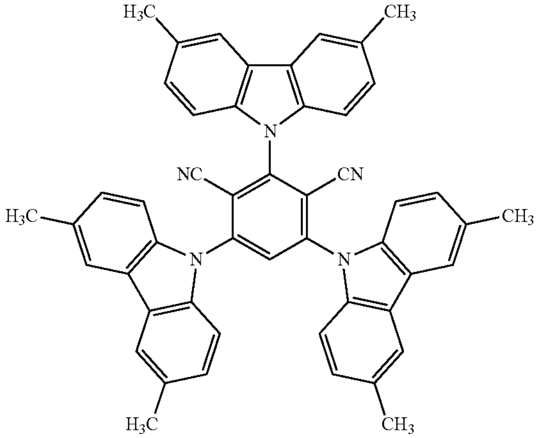

-continued
1-4
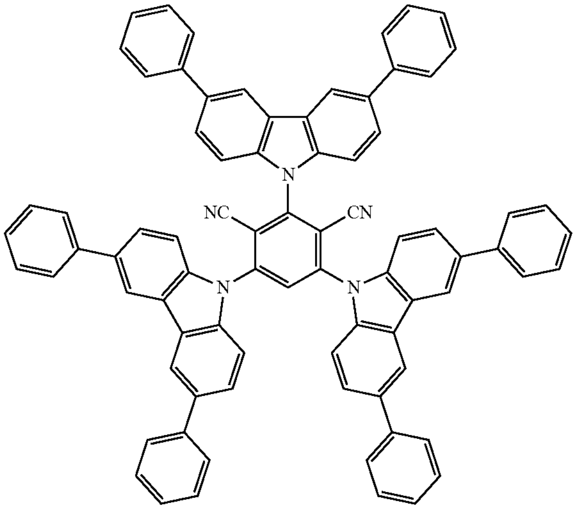
1-5
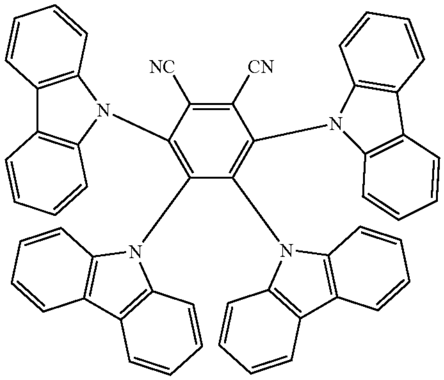
1-6
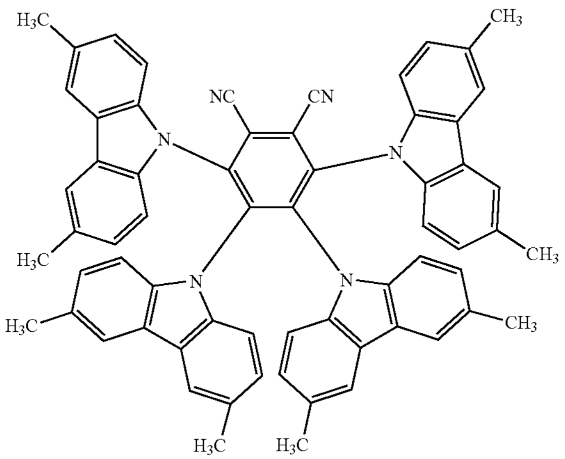
-continued
1-7
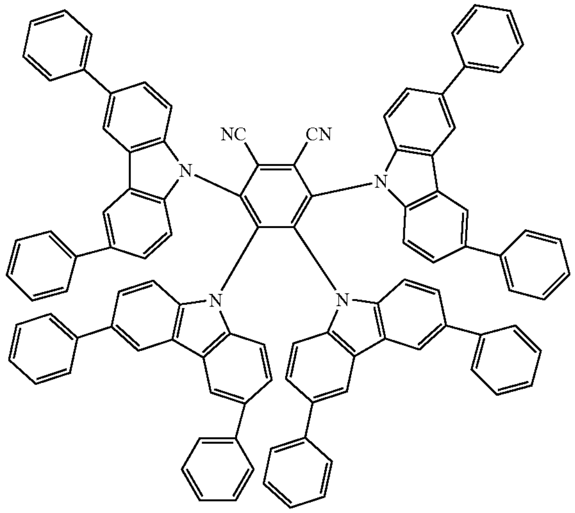
1-8
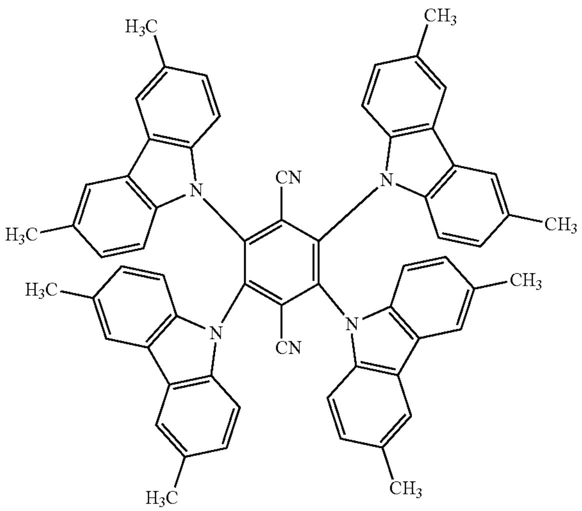
1-9
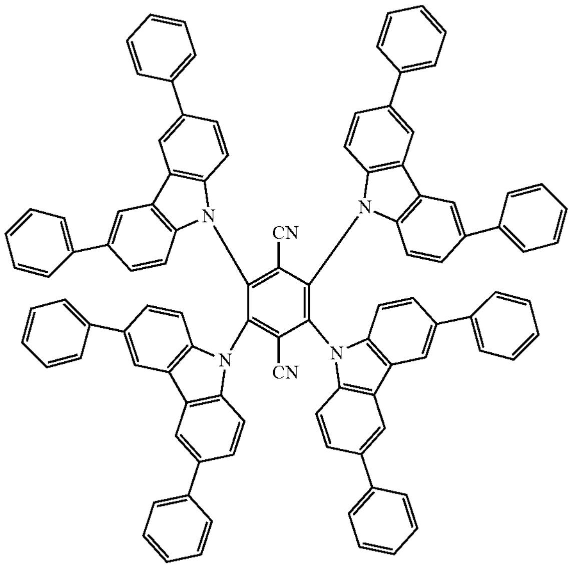

-continued 1-10

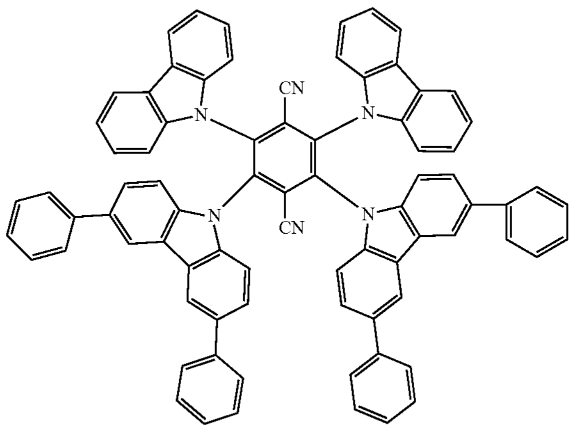

1-11

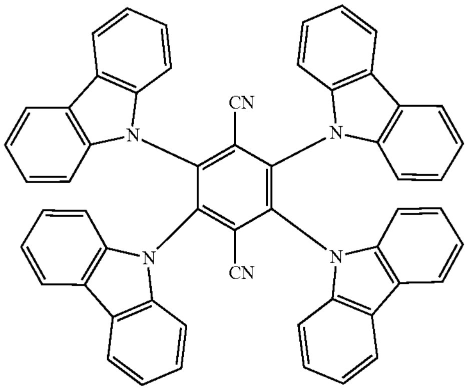

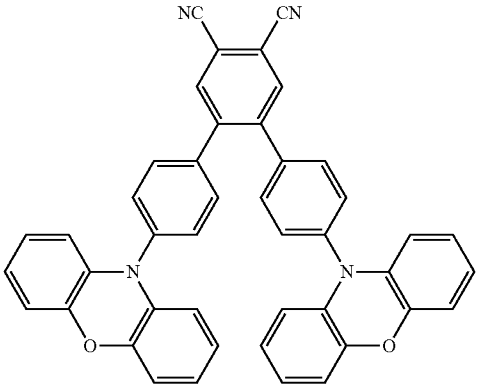

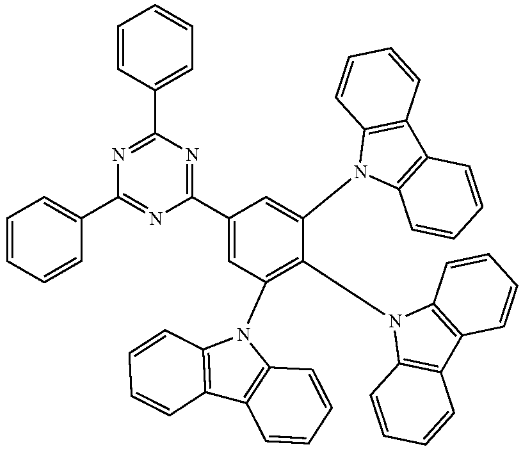

-continued

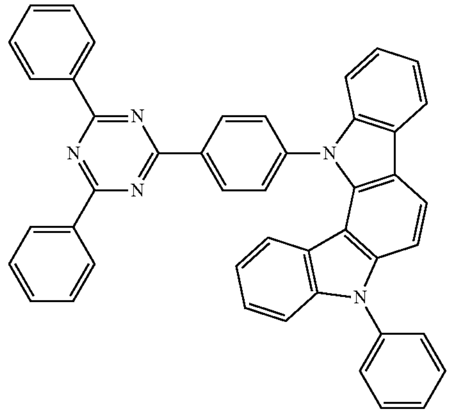

.

8. The organic light emitting diode according to claim 3, further comprising:

a second emitting material layer including a fourth compound being a delayed fluorescent compound and a second host and positioned between the first emitting material layer and the second electrode.

9. The organic light emitting diode according to claim 8, further comprising:

a third emitting material layer including a fifth compound being one of the compounds in Formula 3 and a third compound and positioned between the second emitting material layer and the second electrode.

10. An organic light emitting display device, comprising:

a substrate;

an organic light emitting diode of claim 2 over the substrate; and an encapsulation film covering the organic light emitting diode.

11. The organic light emitting display device according to claim 10, wherein the first emitting material layer further includes a second compound as a host, wherein the second compound is represented by Formula 4-1 or Formula 4-2:

[Formula 4-1]

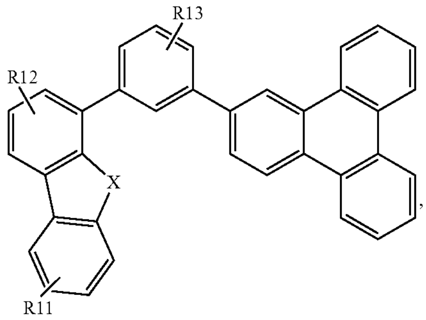

, and

-continued

[Formula 4-2]

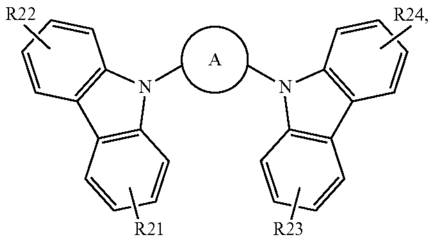

wherein in Formula 4-1, X is oxygen or sulfur, and each of R11 to R13 is independently selected from the group consisting of hydrogen, deuterium, halogen, cyano, silyl, C1 to C20 alkyl group, C6 to C30 aryl group, C5 to C30 heteroaryl group and C1 to C20 amine, and wherein in Formula 4-2, A is selected from the group consisting of C6 to C30 arylene group and C5 to C30 heteroarylene group, and each of R21 to R24 is independently selected from the group consisting of hydrogen, deuterium, halogen, cyano, silyl, C1 to C20 alkyl group, C6 to C30 aryl group, C5 to C30 heteroaryl group and C1 to C20 amine.

12. The organic light emitting display device according to claim 11, wherein the second compound is one of compounds in Formula 5:

[Formula 5]

H1

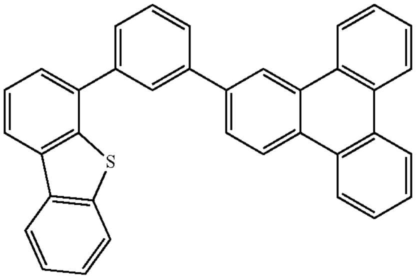

H2

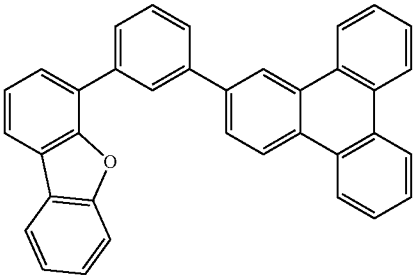

H3

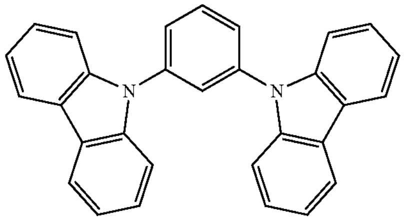

-continued

H4

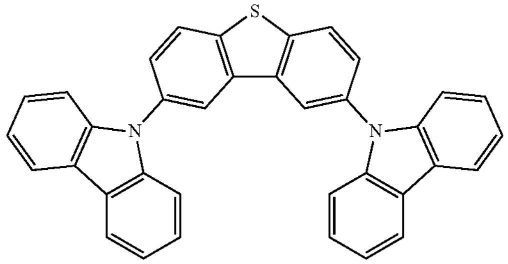

H5

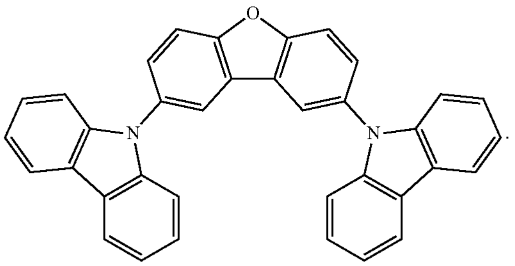

13. The organic light emitting diode according to claim 10, wherein the first emitting material layer further includes a third compound being a delayed fluorescent compound, wherein the third compound is represented by Formula 6:

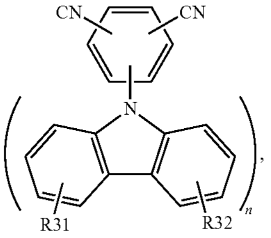

wherein in Formula 6, n is an integer of 1 to 4, and wherein each of R31 and R32 is independently selected from the group consisting of hydrogen, deuterium, tritium, a C1 to C20 alkyl group, a C6 to C30 aryl group and a C3 to C40 heteroaryl group.

14. The organic light emitting display device according to claim 10, wherein the first emitting material layer further includes a third compound being a delayed fluorescent compound, and the third compound is one of compounds in Formula 7:

[Formula 7]
1-1
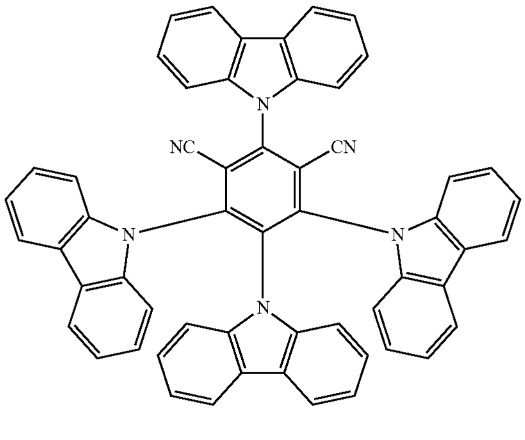
1-2
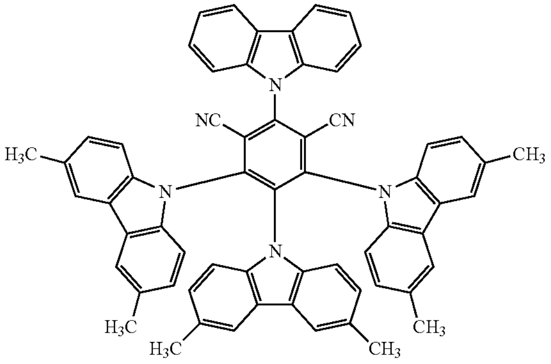
1-3
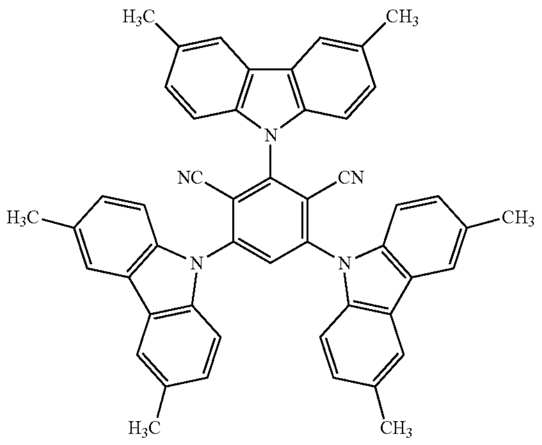
-continued
1-4
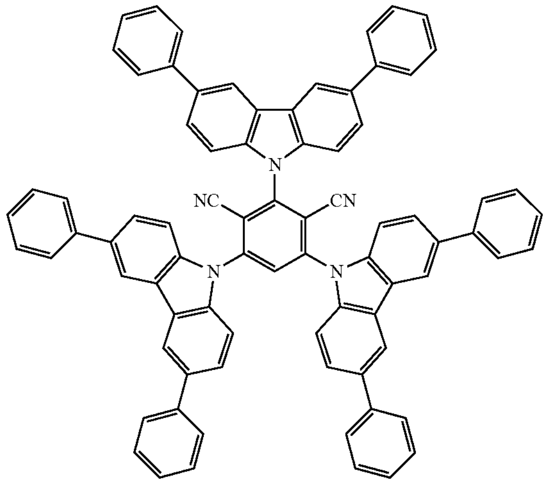
1-5
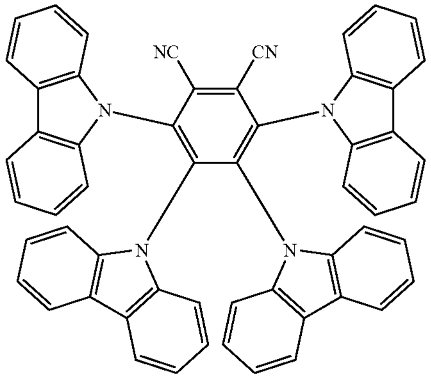
1-6
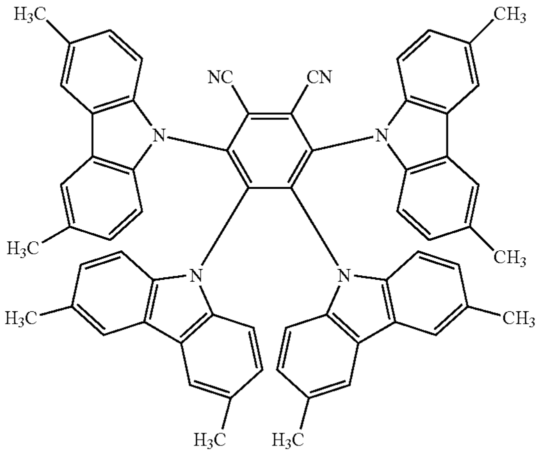

-continued
1-7
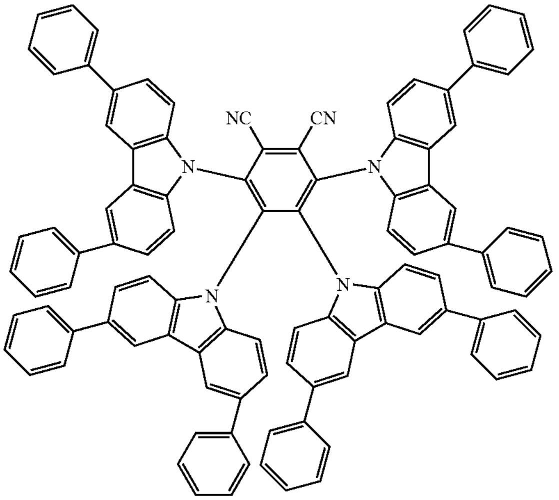
1-8
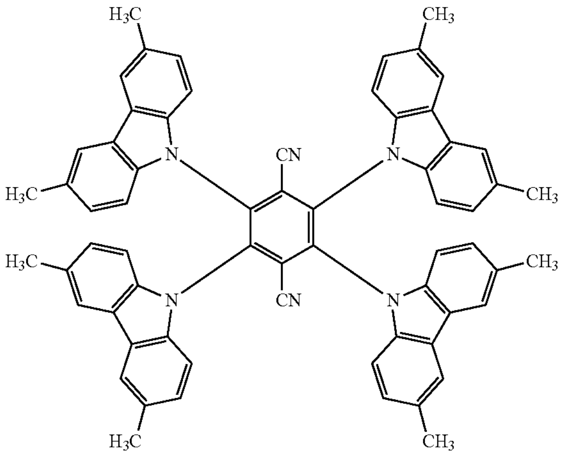
1-9
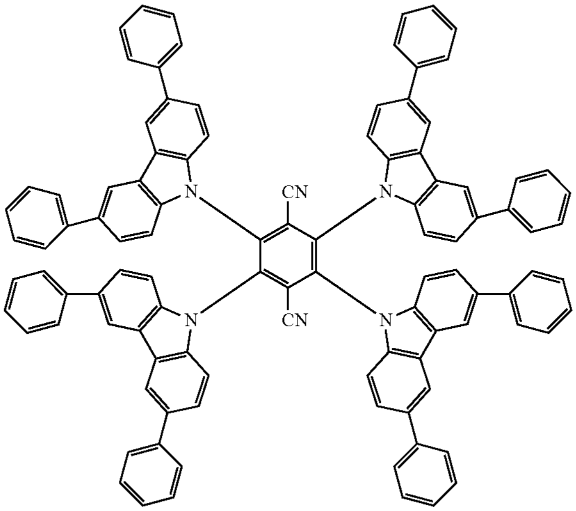
-continued
1-10
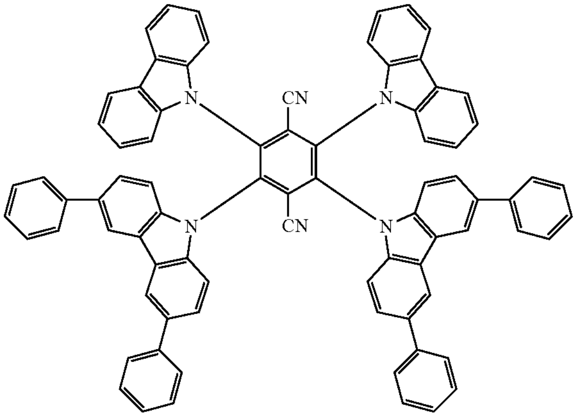
1-11
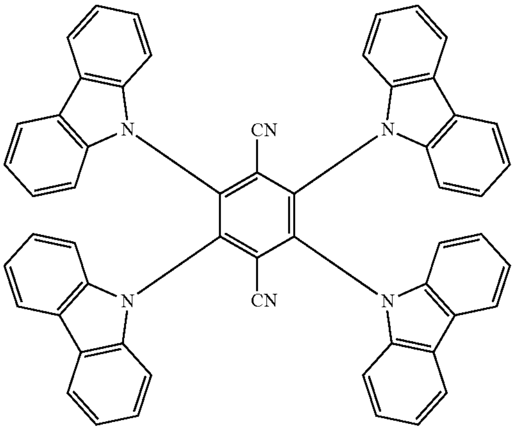
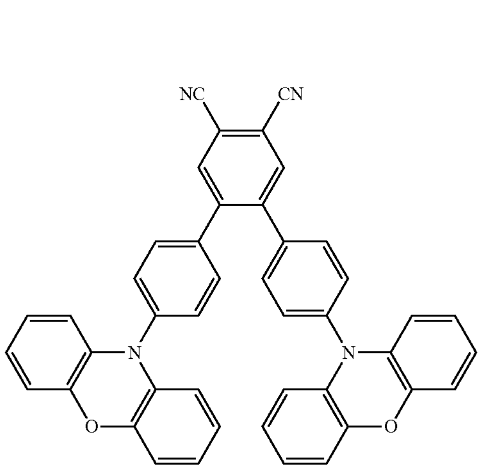

-continued
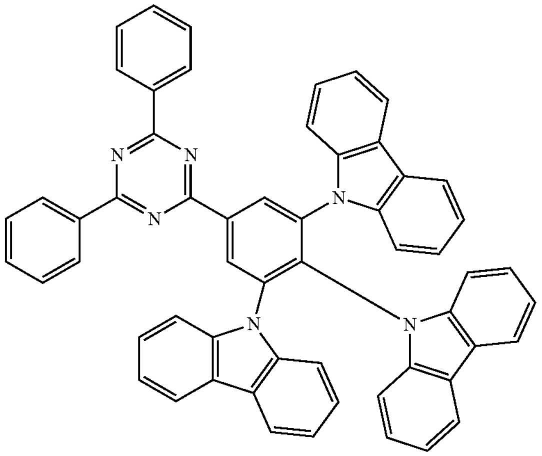
-continued
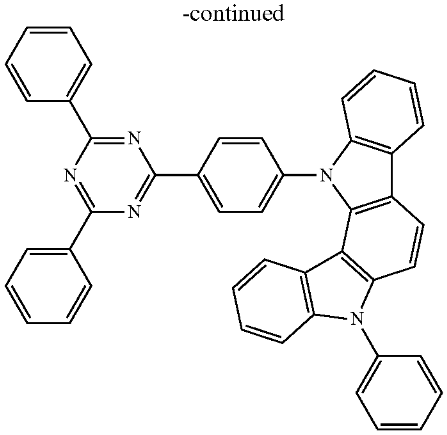
.
* * * * *